(12) United States Patent
Lassoie et al.

(10) Patent No.: US 7,638,630 B2
(45) Date of Patent: Dec. 29, 2009

(54) 2,6-QUINOLINYL AND 2,6-NAPHTHYL DERIVATIVES, PROCESSES FOR PREPARING THEM AND THEIR USES AS VLA-4 INHIBITORS

(75) Inventors: Marie-Agnès Lassoie, Braine-le-Château (BE); Laurent Knerr, Göteborg (SE); Thierry Demaude, Saint-Ghislain (BE); Françoise De Laveleye-Defais, Brussels (BE); Thierry Kogej, Göteborg (SE); Luc Quere, Dampicourt (BE); Sylvain Routier, Tigy (FR); Gerald Guillaumet, St-Jean-le-Blanc (FR)

(73) Assignee: UCB Pharma S.A., Brussels (BE)

( * ) Notice: Subject to any disclaimer, the term of this patent is extended or adjusted under 35 U.S.C. 154(b) by 697 days.

(21) Appl. No.: 10/513,347

(22) PCT Filed: Apr. 15, 2003

(86) PCT No.: PCT/EP03/03909

§ 371 (c)(1),
(2), (4) Date: Nov. 21, 2005

(87) PCT Pub. No.: WO03/093237

PCT Pub. Date: Nov. 13, 2003

(65) Prior Publication Data

US 2008/0064720 A1    Mar. 13, 2008

(30) Foreign Application Priority Data

Apr. 30, 2002    (EP) .................................. 02009746

(51) Int. Cl.
C07D 215/38    (2006.01)
(52) U.S. Cl. .................................................. 546/159
(58) Field of Classification Search ................. 546/153, 546/159
See application file for complete search history.

(56) References Cited

U.S. PATENT DOCUMENTS 6,399,599 B1 * 6/2002 Albert et al. ................. 514/218

FOREIGN PATENT DOCUMENTS

| EP | 0 798 291 A1 | 10/1997 |
|---|---|---|
| JP | 9-87291 | 3/1997 |
| WO | 98/34115 | 8/1998 |
| WO | WO 99/10312 A1 | 3/1999 |
| WO | WO 00/15612 A1 | 3/2000 |
| WO | WO 00/66572 A1 | 11/2000 |
| WO | WO 2006/131200 | 12/2006 |

OTHER PUBLICATIONS

Vela, Marco A. et al.; "Syntheses of 1- and 2-Naphthol Analogues of $_{DL}$-Tyrosine. Potential Fluorescent Probes of Peptide Structure and Dynamics in Complex Environments"; *J. Org. Chem*; 1990; vol. 55; No. 9; pp. 2913-2918.
Elovaara, I. et al., *Arch. Neurol.*, vol. 57, pp. 546 to 551 (2000).
Henderson, W. et al., *J. Clin. Invest.*, vol. 100, No. 12, pp. 3083 to 3092 (1997).
Koch, K. et al., *J. Org. Chem.*, vol. 59, pp. 1216 to 1218 (1994).
Arcadi, A. et al., *Tetrahedron*, vol. 46, No. 20, pp. 7151 to 7164 (1990).
Ali, N., *Tetrahedron*, vol. 48, No. 37, pp. 8117 to 8126 (1992).
Conti, S. et al., *Tetrahedron*, vol. 50, No. 47, pp. 13493-13500 (1994).
Sahali, Y. et al., *J. Org. Chem.*, vol. 55, No. 2918 to 2920 (1990).
Tomita, K. et al., *Clinical and Experimental Allergy*, vol. 27, pp. 664 to 671 (1997).
Rabb, H. et al., *Am. J. Respir. Crit. Care Med*, vol. 149, pp. 1186 to 1191 (1994).
Zangrilli, J. et al., *Am. J. Respir. Crit. Care Med.*, vol. 151, pp. 1346 to 1353 (1995).
Cannella, B. et al., *Annals of Neurology*, vol. 37, No. 4, pp. 424 to 435 (1995).
Keszthelyi, E. et al., *Neurology*, vol. 47, pp. 1053 to 1059 (1996).
Luján, S. et al., *Multiple Sclerosis*, vol. 4, pp. 239 to 242 (1998).
Goodall, K. et al., *J. Chem. Research (S)*, pp. 54 to 55 (2000).
Fernández, M. et al., *Heterocycles*, vol. 38, No. 12, pp. 2615 to 2620 (1994).
Sfikakis, P. P., *Clinical Rheumatology*, vol. 18, pp. 317 to 327 (1999).
Fukuda, T. et al., *Am. J. Respir. Cell Mol. Biol.*, vol. 14, pp. 84 to 94 (1996).
Finkenauer, V. et al., *Microcirculation*, vol. 6, pp. 141 to 152 (1999).
Ianaro, A. et al., *Laboratory Investigation*, vol. 80, No. 1, pp. 73 to 80 ( 2000).
Sagara, H. et al., *International Archives of Allergy and Immunology*, vol. 112, pp. 287 to 294 (1997).
Gosset, P. et al., *International Archives of Allergy and Immunology*, vol. 106, pp. 69 to 77 (1995).
Kitayama, J. et al., *The Journal of Immunology*, vol. 159, pp. 3929 to 3939 (1997).
Bochner, B. S. et al., *Immunological Reviews*, vol. 179, pp. 5 to 15 (2001).

(Continued)

*Primary Examiner*—D. Margaret Seaman
(74) *Attorney, Agent, or Firm*—Hoxie & Associates LLC

(57) ABSTRACT

The present invention concerns 2,6-quinolinyl and 2,6-naphthyl derivatives of formula (I), processes for preparing them, pharmaceutical compositions containing them and their use as pharmaceuticals for the treatment of VLA-4 dependent inflammatory diseases such as for example asthma, allergic rhinitis, sinusitis, conjunctivitis, food allergy, psoriasis, urticaria, pruritus, eczema, rheumatoid arthritis, inflammatory bowel disease, multiple sclerosis and atherosclerosis. Formula (I): wherein X is N or CH.

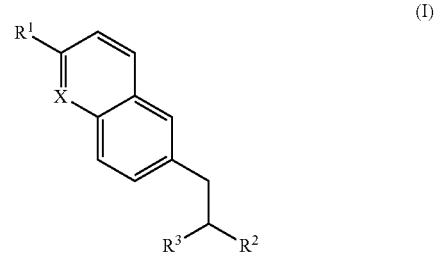

(I)

14 Claims, No Drawings

OTHER PUBLICATIONS

Tagawa, Y. et al., *Heterocycles*, vol. 48, No. 11, pp. 2379 to 2387 (1998).
Akeson, A. et al., *Journal of Immunological Methods*, vol. 163, pp. 181 to 185 (1993).
Pretolani, M. et al., *J. Exp. Med.*, vol. 180, pp. 795 to 805 (1994).
Anwar, A. et al., *J. Exp. Med.*, vol. 177, pp. 839 to 843 (1993).
Bocchino, V. et al., *J. Allergy Clin. Immunol.*, vol. 105, No. 1, pp. 65 to 70 (2000).
Lobb, R. et al., *J. Clin. Invest.*, vol. 94, pp. 1722 to 1728 (1994).
Abraham, W. M. et al., *J. Clin. Invest.*, vol. 93, pp. 776 to 787 (1994).
Podolsky, D. K., *J. Clin. Invest.*, vol. 92, pp. 372 to 380 (1993).

* cited by examiner

2,6-QUINOLINYL AND 2,6-NAPHTHYL DERIVATIVES, PROCESSES FOR PREPARING THEM AND THEIR USES AS VLA-4 INHIBITORS

This application is a National Stage of International Application No. PCT/EP03/03909, filed Apr. 15, 2003.

The present invention concerns 2,6-quinolinyl and 2,6-naphthyl derivatives, processes for preparing them, pharmaceutical compositions containing them and their use as pharmaceuticals.

During the inflammatory process white blood cells infiltrate the extravascular tissue.

This recruitment into areas of inflammation involves the binding of leukocytes to endothelium followed by their transmigration into the tissue. Each step of this process is mediated by specific interactions between adhesion molecules present on the leukocyte cell surface and their counter-ligands expressed on vascular endothelium, epithelium and matrix proteins (B. S. Bochner in Allergy Principles and Practice, E. Middleton et al, Eds. St Louis Mosby, 1998, 94-107).

Adhesion molecules expressed on leukocytes can be subdivided into different groups according to their structures. The two principal groups are the selectin family or their ligands and the integrin family. The different patterns and levels of the expression of these molecules on different leukocyte subsets may explain, to some extent, the differential pattern of leukocyte recruitment in inflamed tissues (B. S. Bochner et al., Immunological Reviews (2001), 179, 5-15).

During the initial step of migration from the blood, leukocytes undergo tethering and rolling, which are principally mediated by the interaction of selectins with their carbohydrated counter-ligands. It has been reported that for some leukocytes, especially eosinophils, the interaction of the α4β1 integrin with its endothelial ligand stabilizes rolling and enhances the cell's arrest (J. Kitayama, J. Immunol. (1997), 159, 3929-3939).

The following firm adhesion to endothelium and cell spreading are mediated by leukocyte integrin interaction with immunoglobulin super-family molecules expressed on the activated endothelium. This step requires leukocyte activation by chemo-attractants or other factors produced in close proximity to the endothelium or by direct interaction with it. Such activation leads to an increase in affinity and/or expression of the integrin resulting in an increased binding to endothelial counter-ligands. Rapid and reversible up-regulation of these molecules allows cells to adhere, detach and migrate.

Leukocytes subsequently transmigrate to the tissue, a process which is also influenced by the interaction of integrins with their endothelial ligands.

Once in the extravascular compartment cells may remain tissue resident, a process maintained by integrin interaction with matrix proteins. Cells may also undergo apoptosis, a process that may be inhibited by integrin/matrix protein interaction ARE. Anwar et al, J. Exp. Med. (1993), 177, 839-843).

Integrins are hetero-dimeric membrane glycoproteins composed of non-covalently associated α and β subunits in combinations that determine ligand specificity. So far 15 α and 8 β chains have been identified and 13 different integrins are expressed on leukocytes. Sub-families β1, β2 and β7 are involved in cell adhesion to endothelium.

The integrin α4β1 (also termed VLA-4 or Very Late Antigen-4 and designated CD49d/CD29) is predominantly expressed on eosinophils, lymphocytes, monocytes and basophils. It binds primarily to the vascular cell surface adhesion molecule VCAM-1 that is expressed on endothelium in response to inflammatory cytokines (TNF-α, IL-1 and selectively IL-4 and IL-13) and to the extracellular matrix protein fibronectin.

Because VLA-4 is not expressed on circulating neutrophils, which are the first defense against infection, it is an attractive target for the pharmacological control of inflammatory diseases.

Several studies have shown that VLA-4 is involved in allergic diseases such asthma and that blocking its function is beneficial.

Asthma is characterized by the accumulation of eosinophils and lymphocytes in bronchial tissue. Immuno-histological analysis of bronchial sub-mucosa obtained from asthmatic patients revealed that VLA-4 is strongly expressed in infiltrated eosinophils and T lymphocytes (V. Bocchino et al, Allergy Clin. Immunol. (2000), 105, 65-70; K. Tomita, Clin. Exp. Allergy (1997), 27, 664-671; Y. Okhawara, Am. J. Respir. Cell Mol. Biol. (1995), 12, 4-12). Over-expression of VCAM-1 was reported in bronchial biopsies from allergic asthmatics compared to normals (P. Gosset et al, Int. Arch. Allergy Immunol. (1995), 106, 69-77). Allergen challenge experiments have shown that several adhesion molecules, including VCAM-1, are up-regulated following the exposure and that this increased expression is correlated with eosinophil infiltration into the tissue space (J. Zangrilli et al, Am. J. Respir. Crit. Care Med. (1995), 151, 1346-1353; T. Fukuda, Am. J. Respir. Cell Mol. Biol. (1996), 14, 84-94).

In several animal models of allergic asthma, blockade of VLA-4 with monoclonal antibody has been shown to reduce the numbers of eosinophils and lymphocytes in the bronchoalveolar fluid (BAL). Some experiments have shown that, in guinea pigs and rats, treatment with a VLA-4 monoclonal antibody inhibits either the late phase response or the airway hyperreactivity seen in these models with a concomitant decrease in eosinophil accumulation in the bronchial tissue (M. Protelani, J. Exp. Med. (1994), 180, 795-805; H. A. Rabb et al, Am. J. Respir. Crit. Care Med. (1994), 149, 1186-1191; H. Sagara, Int. Arch. Allergy Immunol. (1997), 112, 287-294). In a sheep model, VLA-4 monoclonal antibody inhibited the late phase response with a modest reduction in the number of BAL eosinophils (W. M. Abraham et al, J. Clin. Invest. (1994), 93, 776-787). In a mouse model of allergic asthma, intrapulmonary blockade of VLA-4 decreased hyperresponsiveness and Th2 cytokine release whereas VLA-4 blockade on circulating leukocytes decreased the number of eosinophils in BAL fluid (W. R. Henderson et al, J. Clin. Invest. (1997), 100, 3083-3092).

Consistent with these observations, VCAM deficient mice failed to develop pulmonary eosinophilia following ovalbumin challenge (J.-A. Gonzalo et al, J. Clin. Invest. (1996), 10, 2332-2345).

Several in vitro and in vivo studies have indicated an important role of VLA-4 in other cell adhesion-mediated inflamatory pathologies including multiple sclerosis (MS), rheumatoid arthritis (RA), atherosclerosis or inflammatory bowel disease.

Inhibition of VLA-4 function using monoclonal antibodies in a variety of inflammation animal models has proved to be beneficial (R. R. Lobb, J. Clin. Invest. (1994), 94, 1722-1728).

Migration of T lymphocytes into the central nervous system is an important event in the pathogenesis of multiple sclerosis. The VCAM-1/VLA-4 adhesion pathway appears to be of key importance (B. Cannella et al, Ann-Neurol. (1995), 37, 424-435; I. Elovaara et al, Arch-Neurol. (2000), 57, 546-551; S. Lujan et al, Mult-Scler. (1998), 4, 239-242). In a model of experimental allergic encephalomyelitis, which mimics MS, treatment with a monoclonal antibody against VLA-4 decreased both clinical and histopathological parameters (E. Keszthelyi et al, Neurology (1996), 47, 1053-1059).

Rheumatoid arthritis is characterized by infiltration of mononuclear cells into the synovial tissue. Interaction of VLA-4 with VCAM-1 and with the alternative spliced fibronectin containing the CS1 region is thought to mediate the recruitment, the retention and the activation of VLA-4-bearing cells in the inflamed Joints (P. P. Sfikakis, Clin. Rheumatol. (1999), 18, 317-327). Treatment with a monoclonal antibody against VLA-4 significantly reduced oedema formation in an animal model of polyarthritis (which shares features with RA (A. Inaro, Lab. Invest. (2000), 80, 73-80)) and inflammatory cell tissue infiltration in the inflamed rat knee joint capsule (V. Finkenauer, Microcirculation (1999), 6, 141-152).

Treatment with a anti-α4 monoclonal antibody has a beneficial effect in cotton top tamarin model of colitis (D. K. Podolsky, J. Clin. Invest. (1993), 92, 372-380).

Specific inhibitors of the VLA-4 interaction with its ligands VCAM-1 or fibronectin may be effective in the treatment of asthma and other inflammatory disorders.

The international patent application WO0015612-A1 teaches compounds having a general formula

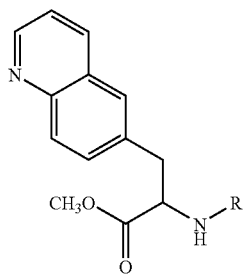

wherein R represents some substituents such as hydrogen, —COOH, —COOalkyl. These compounds can be used as intermediate compounds in a preparation of pharmaceutical compounds, but no pharmaceutical utility for them as such is sought.

It has now surprisingly been found that some analogs of these compounds demonstrate therapeutic properties.

In one aspect, the invention therefore provides a compound having the formula I or a pharmaceutically acceptable salt thereof,

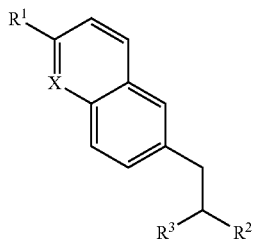

wherein
X is N or CH;
R$^1$ is cycloalkyl, aryl, heterocycle, aralkyl, heterocycle-alkyl, or an oxy derivative, or a group of formula:

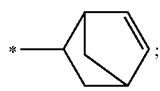

R$^2$ is —NR$^4$R$^5$, —OR$^4$ or —C(=O)NR$^5$R$^6$;
R$^3$ is tetrazole, —CN, —CH$_2$OH or —CO—R$^7$;
R$^4$ is H, —G$^1$—R$^8$, or a group of formula:

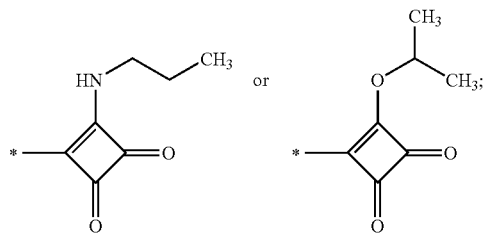

R$^5$ is H, C1-4-alkyl; or —NR$^4$R$^5$ represents an heterocycle or —N=CR$^9$R$^{10}$;
R$^6$ is aryl, heterocycle, cycloalkyl or aralkyl;
R$^7$ is hydroxy, amino, hydroxylamino, an oxy derivative or an amino derivative;
G$^1$ is CO, CH$_2$, SO$_2$;
R$^8$ is aryl, heterocycle, cycloalkyl, aralkyl or —NH-aryl;
R$^9$ is aryl; and
R$^{10}$ is ether;
with the proviso that when X is CH, then R$^1$ is cycloalkyl, aryl, heterocycle, aralkyl, heterocycle-alkyl or a group of formula:

 ; and with the proviso that, when X is CH, R$^1$ is cycloalkyl, R$^2$ is —NR$^4$R$^5$, R$^3$ is —CO—R$^7$, R$^4$ is H or —G$^1$—R$^8$, R$^5$ is H, C1-4-alkyl, G$^1$ is CO, CH$_2$, SO$_2$, R$^8$ is an optionally substituted phenyl, cycloalkyl or —NH-phenyl (an optionally substituted), then R$^7$ is neither an oxy derivative of formula —O—CHR$^b$R$^c$ wherein R$^b$ is H, C1-6-alkyl or an optionally substituted phenyl and R$^c$ is an optionally substituted phenyl, nor an amino derivative of formula —NR$^d$—CHR$^b$R$^c$ wherein R$^b$ and R$^c$ have the same definitions as described above, and R$^d$ is H or C1-6-alkyl.

In the definitions set forth below, unless otherwise stated, the term "alkyl", as used herein, is defined as including saturated, monovalent hydrocarbon radicals having straight, branched or cyclic moieties or combinations thereof and containing 1-20 carbon atoms, preferably 1-6 carbon atoms for non-cyclic alkyl and 3-8 carbon atoms for cycloalkyl (in these two preferred cases, unless otherwise specified, "lower alkyl") and includes alkyl moieties substituted by 1 to 5 substituents independently selected from the group consisting of halogen, hydroxy, thiol, amino, nitro, cyano, acyl derivative, sulfonyl derivative, sulfinyl derivative, alkylamino, carboxy, ester, ether, amido, azido, cycloalkyl, sulfonic acid, sulfonamide, thio derivative, esteroxy, amidooxy, heterocycle, vinyl, C1-6-alkoxy, C6-10-aryloxy and C6-10-aryl.

Preferred alkyl groups are methyl, ethyl, propyl, isopropyl, butyl, iso- or tert-butyl, and 2,2-dimethylpropyl each optionally substituted by at least one substituent selected from the group consisting of halogen, hydroxy, thiol, amino, nitro and cyano, such as trifluoromethyl, trichloromethyl, 2,2,2-trichloroethyl, 1,1-dimethyl-2,2-dibromoethyl, 1,1-dimethyl-2,2,2-trichloroethyl.

The term "cycloalkyl", as used herein, refers to a monovalent group of 3 to 18 carbons derived from a saturated cyclic or polycyclic hydrocarbon such as adamantyl, which can optionally be substituted with any suitable group, including but not limited to one or more moieties selected from lower alkyl or other groups as described above for the alkyl groups. Non-limiting examples are cyclopropyl, cyclobutyl, cyclopentyl, cyclohexyl, cycloheptanyl, cyclooctanyl, bicyclo[3.2.1]cyclooctanyl or adamantyl.

The term "alkenyl" as used herein, is defined as including branched, unbranched and cyclic unsaturated hydrocarbon radicals having at least one double bond such as ethenyl (=vinyl), 1-methyl-1-ethenyl, 2-methyl-1-propenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl, and the like and being optionally substituted by at least one substituent selected from the group consisting of halogen, hydroxy, thiol, amino, nitro, cyano, aryl and heterocycle such as mono- and di-halo vinyl where halo is fluoro, chloro or bromo.

The term "alkynyl" as used herein, is defined as including monovalent branched, unbranched and cyclic hydrocarbon radicals containing at least one carbon-carbon triple bond, for example ethynyl, 2-propynyl (=propargyl), and the like and being optionally substituted by at least one substituent selected from the group consisting of halogen, hydroxy, thiol, amino, nitro, cyano, aryl and heterocycle, such as haloethynyl.

When present as bridging groups, alkyl, alkenyl and alkynyl represent straight or branched chains, C1-12-, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g. "n-propyl", "sec-butyl") are in the n-form unless otherwise stated.

The term "aryl" as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, thiol, amino, nitro, cyano, acyl derivative, sulfonyl derivative, sulfinyl derivative, alkylamino, carboxy, ester, ether, amido, azido, C1-6-alkyl, C1-6-haloalkyl, C3-8-cycloalkyl, sulfonic acid, sulfonamide, thio derivative, esteroxy, amidooxy, heterocycle, vinyl, C1-6-alkoxy, C6-10-aryloxy or C6-10 aryl, where two or more substituents may form a ring attached to the aryl moiety. Preferred aryl groups are phenyl and naphthyl each optionally substituted by 1 to 5 substituents independently selected from halogen, nitro, amino, azido, C1-6-alkoxy, C1-6-alkylthio, C1-6-alkyl, C1-6-haloalkyl and phenyl.

The term "aralkyl", as used herein, represents a group of the formula —$R^{13}$-aryl in which $R^{13}$ is C1-12-straight, branched or cyclic alkylene, or C2-12-straight or branched alkenylene or alkynylene groups. Non-limiting examples are benzyl, halobenzyl, cyanobenzyl, methoxybenzyl, nitrobenzyl, 2-phenylethyl, diphenylmethyl, (4-methoxyphenyl) diphenylmethyl, anthracenylmethyl.

The term "halogen", as used herein, includes a Cl, Br, F or I atom.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "amino", as used herein, represents a group of the formula —$NH_2$.

The term "hydroxylamino", as used herein, represents a group of the formula —NHOH.

The term "azido", as used herein, represents a group of the formula —$N_3$.

The term "carboxy", as used herein, represents a group of the formula —COOH.

The term "sulfonic acid", as used herein, represents a group of the formula —$SO_3H$.

The term "sulfonamide", as used herein, represents a group of the formula —$SO_2NH_2$.

In the definitions set forth below, unless otherwise stated, $R^{11}$ and $R^{12}$ are the same or different and each is independently amido, alkyl, alkenyl, alkynyl, acyl, ester, ether, aryl, aralkyl, heterocycle, heterocycle-alkyl, or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described above as substituents for alkyl.

The term "ester" as used herein is defined as including a group of formula —COO—$R^{11a}$ wherein $R^{11a}$ is as defined above for $R^{11}$ except for "oxy derivative", "thio derivative" or "amino derivative".

The term "ether" is defined as including a group selected from C1-50-straight or branched alkyl, or C2-50-straight or branched alkenyl or alkynyl groups or a combination of the same, interrupted by one or more oxygen atoms.

The term "amido" is defined as including a group of formula —$CONH_2$ or —$CONHR^{11b}$ or —$CONR^{11b}R^{12a}$ wherein $R^{11b}$ and $R^{12a}$ are as defined above for $R^{11}$ and $R^{12}$.

The term "oxy derivative", as used herein is defined as including —O—$R^{11c}$ groups wherein $R^{11c}$ is as defined above for $R^{11}$ except for "oxy derivative", "thio derivative" and "amino derivative". Non-limiting examples are alkoxy, alkenyloxy, alkyloxy, acyloxy, esteroxy, amidooxy, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate.

The term "thio derivative", as used herein, is defined as including —S—$R^{11d}$ groups wherein $R^{11d}$ is as defined above for $R^{11}$ except for "thio derivative", "oxy derivative" and "amino derivative". Non-limiting examples are alkylthio, alkenylthio, alkynylthio and arylthio.

The term "acyl derivative", as used herein, represents a radical derived from carboxylic acid and thus is defined as including groups of the formula $R^{11e}$—CO—, wherein $R^{11e}$ is as defined above for $R^{11}$ and may also be hydrogen. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "amino derivative" as used herein, is defined as including —$NHR^{11f}$ or —$NR^{11f}R^{12b}$ groups wherein $R^{11f}$ and $R^{12b}$ are as defined above for $R^{11}$ and $R^{12}$. Non-limiting examples are mono- or di-alkyl-, alkenyl-, alkynyl- and arylamino or mixed amino.

The term "sulfonyl derivative", as used herein, is defined as including a group of the formula —$SO_2$—$R^{11g}$, wherein $R^{11g}$ is as defined above for $R^{11}$ except for "sulfonyl derivative". Non-limiting examples are alkylsulfinyl, alkenylsulfinyl, alkynylsulfinyl and arylsulfinyl.

The term "sulfinyl derivative", as used herein, is defined as including a group of the formula —SO—$R^{11h}$, wherein $R^{11h}$ is as defined above for $R^{11}$ except for "sulfinyl derivative". Non-limiting examples are alkylsulfinyl, alkenylsulfinyl, alkynylsulfinyl and arylsulfinyl.

The term "heterocycle", as used herein, is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl. In heterocycles comprising a S atom, the S atom may be replaced by a sulfoxide or a sulfone. Non-limiting examples of aromatic heterocycles are pyridyl, furyl, pyrrolyl, thienyl, isothiazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thieno(2,3-b)furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, phenanthridinyl, acridinyl, perimidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted by alkyl or as described above for the alkyl groups. Non-limiting examples of non aromatic heterocycles are tetrahydrofuranyl, tetrahydropyranyl, piperidinyl, piperidyl, piperazinyl, imidazolidinyl, morpholino, morpholinyl, 1-oxaspiro(4.5)dec-2-yl, pyrrolidinyl, 2-oxo-pyrrolidinyl, 1,1-dioxido-1,3-thiazolidin-4-yl, sugar moieties (i.e. glucose, pentose, hexose, ribose, fructose, which may also be substituted) or the same which can optionally be substituted with any suitable group, including but not limited to one or more moieties selected from lower alkyl, or other groups as described above for the alkyl groups. The term "heterocycle" also includes bicyclic, tricyclic and tetracyclic, spiro groups in which any of the above heterocyclic rings is fused to one or two rings independently selected from an aryl ring, a cycloalkyl ring, a cycloalkenyl ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl, 8-azabicyclo(3.2.1)octanyl.

The term "heterocycle-alkyl", as used herein, represents a group of the formula —$R^{14}$-heterocycle in which $R^{14}$ is C1-12-straight, branched or cyclic alkylene, or C2-12-straight or branched alkenylene or alkynylene groups. Non-limiting examples are thiophenemethyl, thiophenethyl, pyridylmethyl and pyridylethyl.

The asterisk (*) indicates the point of attachment of the substituents.

Usually, $R^1$ is cycloalkyl, aryl, heterocycle, aralkyl, heterocycle-alkyl, or an oxy derivative, or a group of formula:

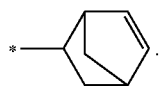

Usually, $R^2$ is —$NR^4R^5$, —$OR^4$ or —C(=O)$NR^5R^6$; $R^4$ is H, —$G^1$—$R^8$, or a group of formula:

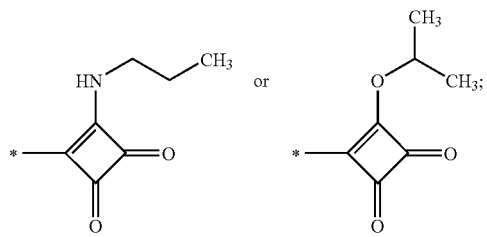

$R^8$ is aryl, heterocycle, cycloalkyl, aralkyl or —NH-aryl; and $G^1$ is CO, $CH_2$, $SO_2$; $R^5$ is H, C1-4-alkyl; or —$NR^4R^5$ represents an heterocycle or —N=$CR^9R^{10}$; $R^9$ is aryl and $R^{10}$ is ether; $R^6$ is aryl, heterocycle, cycloalkyl or aralkyl.

Usually, $R^3$ is tetrazole, —CN, —$CH_2OH$ or —CO—$R^7$; and $R^7$ is hydroxy, amino, hydroxylamine, an oxy derivative or an amino derivative.

Preferably $R^1$ is cycloalkyl, aryl, aromatic heterocycle or aralkyl.

Preferably $R^2$ is —$NR^4R^5$, wherein $R^4$ and $R^5$ are as defined above.

Preferably $R^3$ is —CO—$R^7$, wherein $R^7$ is as defined above.

Preferably $R^4$ is —$G^1$—$R^8$, wherein $G^1$ and $R^8$ are as defined above.

Preferably $R^7$ is hydroxy, amino, hydroxylamino or an oxy derivative.

Preferably $G^1$ is CO.

Preferably $R^8$ is aryl, heterocycle, cycloalkyl or —NH-aryl.

Especially preferred $R^1$ is 2,6-dichlorophenyl, 2,4-dichlorophenyl, 2,6-dimethoxyphenyl, 2-nitrophenyl, 2-(trifluoromethyl)phenyl, 2-bromophenyl, 2-(1,3-benzodioxol-5-yl)-1-methylethyl, 2-methoxyphenyl, 4-(methylsulfonyl)phenyl, 5-chloro-1-methyl-3-(trifluoromethyl)-1H-pyrazol-4-yl, 2,6-dimethylphenyl, 2-chloro-6-nitrophenyl, 3,5-dichloro-4-pyridinyl, 2-chloro-6-fluorophenyl, 2-methoxy-1-naphthyl, 2-mesityl.

Especially preferred $R^2$ is —$NHR^4$, wherein $R^4$ is as defined above.

Especially $R^4$ is —$G^1$—$R^8$, wherein $G^1$ and $R^8$ are as defined above.

Especially preferred $R^7$ is hydroxy, amino or C1-4-alkyloxy.

Especially preferred $R^8$ is 2,6-dichlorophenyl, 1-carboxy-1,2,2-trimethyl-3-cyclopentyl, 1-((4-methylphenyl)sulfonyl)-2-piperidinyl, 1-[(4-methylphenyl)sulfonyl]octahydro-1H-indol-2-yl, 1-(4-chlorophenyl)cyclopentyl, 2-chloro-4-(methylsulfonyl)phenyl, 2-chloro-6-methylphenyl, 3-acetyl-1,3-thiazolidin-4-yl, 2,6-dimethoxyphenyl, 2,6-dimethylphenyl, 2,6-difluorophenyl, 2-chloro-4-(methylsulfonyl)phenyl, 1-(methylsulfonyl)-2-piperidinyl, 2-methyltetrahydro-2-furanyl, 1-acetyl-2-pyrrolidinyl, 1-(phenylsulfonyl)-2-pyrrolidinyl, 2,4-dichloro-6-methyl-3-pyridinyl, 1-benzyl-5-oxo-2-pyrrolidinyl, 3-acetyl-1,1-dioxido-1,3-thiazolidin-4-yl, 1-[2-(diethylamino)ethyl]cyclopentyl.

Best $R^1$ is 2,6-dichlorophenyl, 2,6-dimethoxyphenyl, 3,5-dichloro-4-pyridinyl, 2-nitrophenyl, 2-chloro-6-fluorophenyl, 2-methoxy-1-naphthyl, 2-chloro-6-nitrophenyl.

Best $R^2$ is —NH—C(=O)—$R^8$, wherein $R^8$ is as defined above.

Best R⁷ is hydroxy or C1-4-alkyloxy.

Best R⁸ is 2,6-dichlorophenyl, 1-carboxy-1,2,2-trimethyl-3-cyclopentyl, 1-((4-methylphenyl)sulfonyl)-2-piperidinyl, 1-[(4-methylphenyl)sulfonyl]octahydro-1H-indol-2-yl, 1-(4-chlorophenyl)cyclopentyl, 2-chloro-4-(methylsulfonyl)phenyl, 2-chloro-6-methylphenyl, 1-(phenylsulfonyl)-2-pyrrolidinyl, 2,4-dichloro-6-methyl-3-pyridinyl, 1-benzyl-5-oxo-2-pyrrolidinyl.

Combinations of one or more of these preferred compound groups are especially preferred.

More preferred compounds are: methyl (2S)-2-[(2,6-dichlorobenzoyl)amino]-3-[2-(2,6-dichlorophenyl)-6-quinolinyl]propanoate; 2-[(2,6-dichlorobenzoyl)amino]-3-[2-(2,6-dichlorophenyl)-6-quinolinyl]propanoic acid; (2S)-2-[(2,6-dichlorobenzoyl)amino]-3-[2-(2,6-dichlorophenyl)-6-quinolinyl]propanoic acid; 2-({[(4R)-3-acetyl-1,3-thiazolidin-4-yl]carbonyl}amino)-3-[2-(2,6-dichlorophenyl)-6-quinolinyl]propanoic acid; 2-[(2,6-dichlorobenzoyl)amino]-3-[2-(2,6-dimethoxyphenyl)-6-quinolinyl]propanoic acid; 3-[2-(2,6-dichlorophenyl)-6-quinolinyl]-2-[(2,6-dimethoxybenzoyl)amino]propanoic acid; 3-[2-(2,6-dichlorophenyl)-6-quinolinyl]-2-[(2,6-dimethylbenzoyl)amino]propanoic acid; 2-[(2,6-dichlorobenzoyl)amino]-3-[2-(4-pyridinyl)-6-quinolinyl]propanoic acid; 2-[(2,6-dichlorobenzoyl)amino]-3-[2-(3,5-dichloro-4-pyridinyl)-6-quinolinyl]propanoic acid; methyl 2-[(2,6-dichlorobenzoyl)amino]-3-[2-(3,5-dichloro-4-pyridinyl)-6-quinolinyl]propanoate; 3-[2-(2,6-dichlorophenyl)-6-quinolinyl]-2-[(2,6-difluorobenzoyl)amino]propanoic acid; methyl (2S)-2-{[2-chloro-4-(methylsulfonyl)benzoyl]amino}-3-[2-(2,6-dichlorophenyl)-6-quinolinyl]propanoate; (2S)-2-[(2-chloro-6-methylbenzoyl)amino]-3-[2-(2,6-dichlorophenyl)-6-quinolinyl]propanoic acid; (2S)-2-{[2-chloro-4-(methylsulfonyl)benzoyl]amino}-3-[2-(2,6-dichlorophenyl)-6-quinolinyl]propanoic acid; 2-({[(2,6-dichlorophenyl)amino]carbonyl}amino)-3-[2-(2,6-dichlorophenyl)-6-quinolinyl]propanoic acid; (2S)-2-({[1-(4-chlorophenyl)cyclopentyl]carbonyl}amino)-3-[2-(2,6-dichlorophenyl)-6-quinolinyl]propanoic acid; 3-[2-(2,6-dichlorophenyl)-6-quinolinyl]-2-[({(2S)-1-[(4-methylphenyl)sulfonyl]piperidinyl}carbonyl)amino] propanoic acid; (1R,3S)-3-[({1-carboxy-2-[2-(2,6-dichlorophenyl)-6-quinolinyl]ethyl}amino)carbonyl]-1,2,2-trimethylcyclopentanecarboxylic acid; (2S)-2-[(2,6-difluorobenzoyl)amino]-3-[2-(2-nitrophenyl)-6-quinolinyl] propanoic acid; (2S)-3-[2-(2-chloro-6-fluorophenyl)-6-quinolinyl]-2-[(2,6-difluorobenzoyl)amino]propanoic acid; (2S)-2-[(2,6-difluorobenzoyl)amino]-3-[2-(2-methoxy-1-naphthyl)-6-quinolinyl]propanoic acid; (2S)-2[(2,6-dichlorobenzoyl)amino]-3-[2-(2-nitrophenyl)-6-quinolinyl]propanoic acid; (2S)-2-[(2,6-dichlorobenzoyl)amino]-3-{2-[2-(trifluoromethyl)phenyl]-6-quinolinyl}propanoic acid; (2S)-3-[2-(2-chloro-6-fluorophenyl)-6-quinolinyl]-2-[(2,6-dichlorobenzoyl)amino]propanoic acid; (2S)-2-[(2,6-dichlorobenzoyl)amino]-3-[2-(2-methoxy-1-naphthyl)-6-quinolinyl]propanoic acid; (2S)-2-[(2-chloro-6-methylbenzoyl)amino]-3-[2-(2-nitrophenyl)-6-quinolinyl] propanoic acid; (2S)-2-[(2-chloro-6-methylbenzoyl)amino]-3-{2-[2-(trifluoromethyl)phenyl]-6-quinolinyl}propanoic acid; (2S)-3-[2-(2-chloro-6-fluorophenyl)-6-quinolinyl]-2-[(2-chloro-6-methylbenzoyl)amino]propanoic acid; (2S)-2-[(2-chloro-6-methylbenzoyl)amino]-3-[2-(2-methoxy-1-naphthyl)-6-quinolinyl]propanoic acid; (2S)-2-{[2-chloro-4-(methylsulfonyl)benzoyl]amino}-3-{2-[2-nitrophenyl]-6-quinolinyl}propanoic acid; (2S)-2-1-[2-chloro-4-(methylsulfonyl)benzoyl]amino}₃-{2-[2-(trifluoromethyl)phenyl]-6-quinolinyl}propanoic acid; (2S)-3-[2-(2-chloro-6-fluorophenyl)-6-quinolinyl]-2-{[2-chloro-4-(methylsulfonyl)benzoyl]amino}propanoic acid; (2S)-2-{[2-chloro-4-(methylsulfonyl)benzoyl]amino}-3-[2-(2-methoxy-1-naphthyl)-6-quinolinyl]propanoic acid; (2S)-2-({[(4R)-3-acetyl-1,3-thiazolidin-4-yl]carbonyl}amino)-3-[2-(2,6-dimethoxyphenyl)-6-quinolinyl]propanoic acid; 2-[({(2S,3aS,7aS)-1-[(4-methylphenyl)sulfonyl]octahydro-1H-indol-2-yl}carbonyl)amino]-3-[2-(2,6-dichlorophenyl)-6-quinolinyl]propanoic acid; methyl (2S)-3-[2-(2,6-dichlorophenyl)-6-quinolinyl]-2-({[(2R)-2-methyltetrahydro-2-furanyl]carbonyl}amino)propanoate; (2S)-3-[2-(2,6-dichlorophenyl)-6-quinolinyl]-2-({[(2S)-2-methyltetrahydro-2-furanyl]carbonyl}amino)propanoic acid; (2S)-3-[2-(2,6-dichlorophenyl)-6-quinolinyl]-2-({[(2R)-2-methyltetrahydro-2-furanyl]carbonyl}amino)propanoic acid; 2,6-dichloro-N-[1-{[2-(2,6-dichlorophenyl)-6-quinolinyl]methyl}-2-(hydroxyamino)-2-oxoethyl]benzamide; N-(2-amino-1-{[2-(2,6-dichlorophenyl)-6-quinolinyl]methyl}-2-oxoethyl)-2,6-dichlorobenzamide; methyl (2S)-3-[2-(2,6-dichlorophenyl)-6-quinolinyl]-2-({[(2S)1-(methylsulfonyl)piperidinyl]carbonyl}amino)propanoate; (2S)-3-[2-(2,6-dichlorophenyl)-6-quinolinyl]-2-({[(2S)-1-(methylsulfonyl)piperidinyl]carbonyl}amino)propanoic acid; ({2-[(2,6-dichlorobenzoyl)amino]-3-[2-(2,6-dichlorophenyl)-6-quinolinyl]propanoyl}oxy)methyl pivalate; 2-[({(2S,3aS,7aS)-1-[(4-methylphenyl)sulfonyl]octahydro-1H-indol-2-yl}carbonyl)amino]-3-[2-(2-chlorophenyl)-6-quinolinyl]propanoic acid; 3-[2-(2-bromophenyl)-6-quinolinyl]-2-[(2,6-dichlorobenzoyl)amino]propanoic acid; 3-[2-(2-bromophenyl)-6-quinolinyl]-2-[({(2S)-1-[(4-methylphenyl)sulfonyl]piperidinyl}carbonyl)amino] propanoic acid; 2-[({(2S,3aS,7aS)-1-[(4-methylphenyl)sulfonyl]octahydro-1H-indol-2-yl}carbonyl)amino]-3-[2-(2-bromophenyl)-6-quinolinyl]propanoic acid; 3-{2-[2-chloro-5-(trifluoromethyl)phenyl]-6-quinolinyl}-2-[(2,6-dichlorobenzoyl)amino]propanoic acid; 2-[(2-chloro-6-methylbenzoyl)amino]-3-{2-[2-chloro-5-(trifluoromethyl)phenyl]-6-quinolinyl}propanoic acid; 2-{[2-chloro-4-(methylsulfonyl)benzoyl]amino}-3-{2-[2-chloro-5-(trifluoromethyl)phenyl]-6-quinolinyl}propanoic acid; 3-{2-[2-chloro-5-(trifluoromethyl)phenyl]-6-quinolinyl}-2-[({(2S)-1-[(4-methylphenyl)sulfonyl]piperidinyl}carbonyl) amino]propanoic acid; 2-[({(2S,3aS,7aS)-1-[(4-methylphenyl)sulfonyl]octahydro-1H-indol-2-yl}carbonyl)amino]-3-{2-[2-chloro-5-(trifluoromethyl)phenyl]-6-quinolinyl}propanoic acid; 2-({[1-(4-chlorophenyl)cyclopentyl]carbonyl}amino)-3-[2-(2-nitrophenyl)-6-quinolinyl]propanoic acid; 2-[(2,6-dimethoxybenzoyl)amino]-3-[2-(2-nitrophenyl)-6-quinolinyl]propanoic acid; 2-[(2-chloro-6-methylbenzoyl)amino]-3-(2-cyclohexyl-6-quinolinyl)propanoic acid; 3-{2-[2-(1,3-benzodioxol-5-yl)-1-methylethyl]-6-quinolinyl}-2-[(2-chloro-6-methylbenzoyl)amino]propanoic acid; 3-{2-[2-(1,3-benzodioxol-5-yl)-1-methylethyl]-6-quinolinyl}-2-{([2-chloro-4-(methylsulfonyl)benzoyl]amino}propanoic acid; 2-({[1-(4-chlorophenyl)cyclopentyl]carbonylamino)-3-[2-(2-methoxyphenyl)-6-quinolinyl]propanoic acid; 2-({1-(4-chlorophenyl)cyclopentyl]carbonyl}amino)-3-[2-(2,6-dimethoxyphenyl)-6-quinolinyl]propanoic acid; 2-[(2-chloro-6-methylbenzoyl)amino]-3-[2-(2-methoxyphenyl)-6-quinolinyl]propanoic acid; 2-[(2-chloro-6-methylbenzoyl)amino]-3-[2-(2,3-dimethoxyphenyl)-6-quinolinyl]propanoic acid; 2-{[2-chloro-4-(methylsulfonyl)benzoyl]amino}-3-[2-(2-methoxyphenyl)-6-quinolinyl]propanoic acid; 2-{[2-chloro-4-(methylsulfonyl)benzoyl]amino}-3-[2-(2,3-dimethoxyphenyl)-6-quinolinyl]propanoic acid; 2-{[2-chloro-4-(methylsulfonyl)benzoyl]amino}-3-[2-(2,6- dimethoxyphenyl)-6-quinolinyl]propanoic acid; 2-[(2,6-dichlorobenzoyl)amino]-3-[2-(2,4-dichlorophenyl)-6-quinolinyl]propanoic acid; 2-[(2,6-dichlorobenzoyl)amino]-3-{2-[4-(methylsulfonyl)phenyl]-6-quinolinyl}propanoic acid; 3-[2-(2-chloro-6-fluorophenyl)-6-quinolinyl]-2-({[1-(4-chlorophenyl)cyclopentyl]carbonyl}amino)propanoic acid; 2-({[1-(4-chlorophenyl)cyclopentyl]carbonyl}amino)-3-{2-[2-(trifluoromethyl)phenyl]-6-quinolinyl}propanoic acid; 3-[2-(2,4-dichlorophenyl)-6-quinolinyl]-2-[(2,6-dimethoxybenzoyl)amino]propanoic acid; 2-[(2,6-dimethoxybenzoyl)amino]-3-{2-[2-(trifluoromethyl)phenyl]-6-quinolinyl}propanoic acid; 2-[(2,6-difluorobenzoyl)amino]-3-{2-[4-(methylsulfonyl)phenyl]-6-quinolinyl}propanoic acid; 2-[(2-chloro-6-methylbenzoyl)amino]-3-(2-mesityl-6-quinolinyl)propanoic acid; 2-[(2-chloro-6-methylbenzoyl)amino]-3-[2-(2,4-dichlorophenyl)-6-quinolinyl]propanoic acid; 2-{[2-chloro-4-(methylsulfonyl)benzoyl]amino}-3-(2-mesityl-6-quinolinyl)propanoic acid; 2-{[2-chloro-4-(methylsulfonyl)benzoyl]amino}-3-[2-(2,4-dichlorophenyl)-6-quinolinyl]propanoic acid; 2-{[(1-acetyl-2-pyrrolidinyl)carbonyl]amino}-3-[2-(2,4-dichlorophenyl)-6-quinolinyl]propanoic acid; (2S)-2-[(2,6-dichlorobenzoyl)amino]-3-[2-(2,6-dimethylphenyl)-6-quinolinyl]propanoic acid; 2-({[1-(4-chlorophenyl)cyclopentyl]carbonyl}amino)-3-[2-(2,3-difluorophenyl)-6-quinolinyl]propanoic acid; 2-[(2,6-dimethoxybenzoyl)amino]-3-[2-(2-methoxy-1-naphthyl)-6-quinolinyl]propanoic acid; 2-[(2-chloro-6-methylbenzoyl)amino]-3-{2-[5-chloro-1-methyl-3-(trifluoromethyl)-1H-pyrazol-4-yl]-6-quinolinyl}propanoic acid; 2-{[2-chloro-4-(methylsulfonyl)benzoyl]amino}-3-{2-[5-chloro-1-methyl-3-(trifluoromethyl)-1H-pyrazol-4-yl]-6-quinolinyl}propanoic acid; (2S)-2-[2-chloro-4-(methylsulfonyl)benzoyl]amino}-3-[2-(2,6-dimethylphenyl)-6-quinolinyl]propanoic acid; 2-[(2,6-dichlorobenzoyl)amino]-3-[2-(2,6-difluorophenyl)-6-quinolinyl]propanoic acid; 3-[2-(2-chloro-6-nitrophenyl)-6-quinolinyl]-2-[(2,6-dichlorobenzoyl)amino]propanoic acid; 3-[2-(2-chloro-6-nitrophenyl)-6-quinolinyl]-2-[(2,6-dimethoxybenzoyl)amino]propanoic acid; 2-[(2-chloro-6-methylbenzoyl)amino]-3-[2-(2,6-difluorophenyl)-6-quinolinyl]propanoic acid; 2-[(2-chloro-6-methylbenzoyl)amino]-3-[2-(2-chloro-6-nitrophenyl)-6-quinolinyl]propanoic acid; 2-[(2,6-dichlorobenzoyl)amino]-3-[6-(2,6-dimethoxyphenyl)-2-naphthyl]propanoic acid; (−)-methyl 2-[(2,6-dichlorobenzoyl)amino]-3-[6-(2,6-dimethoxyphenyl)-2-naphthyl]propanoate; (−)-2-[(2,6-dichlorobenzoyl)amino]-3-[6-(2,6-dimethoxyphenyl)-2-naphthyl]propanoic acid; (+)-2-[(2,6-dichlorobenzoyl)amino]-3-[6-(2,6-dimethoxyphenyl)-2-naphthyl]propanoic acid; 3-[6-(2,6-dimethoxyphenyl)-2-naphthyl]-2-({[(2S)-1-(phenylsulfonyl)pyrrolidinyl]carbonyl}amino)propanoic acid; methyl 3-[6-(2,6-dimethoxyphenyl)-2-naphthyl]-2-({[(2S)-1-(phenylsulfonyl)pyrrolidinyl]carbonyl}amino)propanoate; methyl (2S)-2-{[(2,4-dichloro-6-methyl-3-pyridinyl)carbonyl]amino}-3-[2-(2,6-dichlorophenyl)-6-quinolinyl]propanoate; (1R,3S)-3-{[((1S)-1-{[2-(2,6-dichlorophenyl)-6-quinolinyl]methyl}-2-methoxy-2-oxoethyl)amino]carbonyl}-1,2,2-trimethylcyclopentanecarboxylic acid; methyl 2-[(2,6-dichlorobenzoyl)amino]-3-[2-(2,6-dimethoxyphenyl)-6-quinolinyl]propanoate; (1R,3S)-3-[({(1S)-1-carboxy-2-[2-(2,6-dichlorophenyl)-6-quinolinyl]ethyl}amino)carbonyl]-1,2,2-trimethylcyclopentanecarboxylic acid; (2S)-2-({[(4R)-3-acetyl-1,1-dioxido-1,3-thiazolidin-4-yl]carbonyl}amino)-3-[2-(2,6-dichlorophenyl)-6-quinolinyl]propanoic acid; (2S)-2-{[(2,4-dichloro-6-methyl-3-pyridinyl)carbonyl]amino}-3-[2-(2,6-dichlorophenyl)-6-quinolinyl]propanoic acid; methyl (2S)-2-[(2,6-dichlorobenzoyl)amino]-3-[2-(2,6-dimethoxyphenyl)-6-quinolinyl]propanoate; methyl (2S)-2-[(2,6-dichlorobenzoyl)amino]-3-[2-(2,6-dimethylphenyl)-6-quinolinyl]propanoate; (2S)-2-[(2,6-dichlorobenzoyl)amino]-3-[2-(2,6-dimethoxyphenyl)-6-quinolinyl]propanoic acid; (2R)-2-[(2,6-dichlorobenzoyl)amino]-3-[2-(2,6-dimethoxyphenyl)-6-quinolinyl]propanoic acid; (2S)-3-[2-(2,6-dimethoxyphenyl)-6-quinolinyl]-2-({[(2R)-2-methyltetrahydro-2-furanyl]carbonyl}amino)propanoic acid; 2-{[(1-aminocyclopentyl)carbonyl]amino}-3-[2-(2,6-dichlorophenyl)-6-quinolinyl]propanoic acid; (2S)-3-[2-(2,6-dichlorophenyl)-6-quinolinyl]-2-[({1-[2-(diethylamino)ethyl]cyclopentyl}carbonyl)amino]propanoic acid; (2S)-2-[(2,6-dichlorobenzoyl)amino]-3-[2-(3,5-dichloro-4-pyridinyl)-6-quinolinyl]propanoic acid; (2S)-3-[2-(3,5-dichloro-4-pyridinyl)-6-quinolinyl]-2-({[(2R)-2-methyltetrahydro-2-furanyl]carbonyl}amino)propanoic acid; methyl 3-[2-(2,6-dichlorophenyl)-6-quinolinyl]-2-({[(2S)-1-(phenylsulfonyl)pyrrolidinyl]carbonyl}amino)propanoate; methyl (2S)-2-({[1-(4-chlorophenyl)cyclopentyl]carbonyl}amino)-3-[2-(3,5-dichloro-4-pyridinyl)-6-quinolinyl]propanoate; (2S)-2-({[1-(4-chlorophenyl)cyclopentyl]carbonyl}amino)-3-[2-(3,5-dichloro-4-pyridinyl)-6-quinolinyl]propanoic acid; (2S)-2-({[(2S)-1-benzyl-5-oxopyrrolidinyl]carbonyl}amino)-3-[2-(2,6-dichlorophenyl)-6-quinolinyl]propanoic acid and 3-[2-(2,6-dichlorophenyl)-6-quinolinyl]-2-({[(2S)-1-(phenylsulfonyl)pyrrolidinyl]carbonyl}amino)propanoic acid, and pharmaceutically acceptable salts thereof.

Most preferred compounds are: methyl (2S)-2-[(2,6-dichlorobenzoyl)amino]-3-[2-(2,6-dichlorophenyl)-6-quinolinyl]propanoate; 2-[(2,6-dichlorobenzoyl)amino]-3-[2-(2,6-dichlorophenyl)-6-quinolinyl]propanoic acid; (2S)-2-[(2,6-dichlorobenzoyl)amino]-3-[2-(2,6-dichlorophenyl)-6-quinolinyl]propanoic acid; 2-({[(4R)-3-acetyl-1,3-thiazolidin-4-yl]carbonyl}amino)-3-[2-(2,6-dichlorophenyl)-6-quinolinyl]propanoic acid; 2-[(2,6-dichlorobenzoyl)amino]-3-[2-(2,6-dimethoxyphenyl)-6-quinolinyl]propanoic acid; 3-[2-(2,6-dichlorophenyl)-6-quinolinyl]-2-[(2,6-dimethoxybenzoyl)amino]propanoic acid; 3-[2-(2,6-dichlorophenyl)-6-quinolinyl]-2-[(2,6-dimethylbenzoyl)amino]propanoic acid; 2-[(2,6-dichlorobenzoyl)amino]-3-[2-(3,5-dichloro-4-pyridinyl)-6-quinolinyl]propanoic acid; methyl 2-[(2,6-dichlorobenzoyl)amino]-3-[2-(3,5-dichloro-4-pyridinyl)-6-quinolinyl]propanoate; methyl (2S)-2-{[2-chloro-4-(methylsulfonyl)benzoyl]amino}-3-[2-(2,6-dichlorophenyl)-6-quinolinyl]propanoate; (2S)-2-[(2-chloro-6-methylbenzoyl)amino]-3-[2-(2,6-dichlorophenyl)-6-quinolinyl]propanoic acid; (2S)-2-{[2-chloro-4-(methylsulfonyl)benzoyl]amino}-3-[2-(2,6-dichlorophenyl)-6-quinolinyl]propanoic acid; (2S)-2-({[1-(4-chlorophenyl)cyclopentyl]carbonyl}amino)-3-[2-(2,6-dichlorophenyl)-6-quinolinyl]propanoic acid; 3-[2-(2,6-dichlorophenyl)-6-quinolinyl]-2-[({(2S) 1-[(4-methylphenyl)sulfonyl]piperidinyl}carbonyl)amino]propanoic acid; (1R,3S)-3-[({1-carboxy-2-[2-(2,6-dichlorophenyl)-6-quinolinyl]ethyl}amino)carbonyl]-1,2,2-trimethylcyclopentanecarboxylic acid; (2S)-2-[(2,6-difluorobenzoyl)amino]-3-[2-(2-nitrophenyl)-6-quinolinyl]propanoic acid; (2S)-2-[(2,6-dichlorobenzoyl)amino]-3-[2-(2-nitrophenyl)-6-quinolinyl]propanoic acid; (2S)-2-[(2,6-dichlorobenzoyl)amino]-3-{2-[2-(trifluoromethyl)phenyl]-6-quinolinyl}propanoic acid; (2S)-3-[2-(2-chloro-6-fluorophenyl)-6-quinolinyl]-2-[(2,6-dichlorobenzoyl)amino]propanoic acid; (2S)-2-[(2,6-dichlorobenzoyl)amino]-3-[2-(2-methoxy-1-naphthyl)-6-quinolinyl]propanoic acid; (2S)-2-[(2-chloro-6-methylbenzoyl)amino]-

3-[2-(2-nitrophenyl)-6-quinolinyl]propanoic acid; (2S)-3-[2-(2-chloro-6-fluorophenyl)-6-quinolinyl]-2-[(2-chloro-6-methylbenzoyl)amino]propanoic acid; (2S)-2-[(2-chloro-6-methylbenzoyl)amino]-3-[2-(2-methoxy-1-naphthyl)-6-quinolinyl]propanoic acid; (2S)-2-{[2-chloro-4-(methylsulfonyl)benzoyl]amino}-3-{2-[2-nitrophenyl]-6-quinolinyl}propanoic acid; (2S)-2-{[2-chloro-4-(methylsulfonyl)benzoyl]amino}-3-{2-[2-(trifluoromethyl)phenyl]-6-quinolinyl}propanoic acid; (2S)-3-[2-(2-chloro-6-fluorophenyl)-6-quinolinyl]-2-{[2-chloro-4-(methylsulfonyl)benzoyl]amino}propanoic acid; (2S)-2-{[2-chloro-4-(methylsulfonyl)benzoyl]amino}-3-[2-(2-methoxy-1-naphthyl)-6-quinolinyl]propanoic acid; (2S)-2-({[(4R)-3-acetyl-1,3-thiazolidin-4-yl]carbonyl}amino)-3-[2-(2,6-dimethoxyphenyl)-6-quinolinyl]propanoic acid; 2-[({(2S,3aS,7aS)-1-[(4-methylphenyl)sulfonyl]octahydro-1H-indol-2-yl}carbonyl)amino]-3-[2-(2,6-dichlorophenyl)-6-quinolinyl]propanoic acid; methyl (2S)-3-[2-(2,6-dichlorophenyl)-6-quinolinyl]-2-({[(2R)-2-methyltetrahydro-2-furanyl]carbonyl}amino)propanoate; (2S)-3-[2-(2,6-dichlorophenyl)-6-quinolinyl]-2-({[(2R)-2-methyltetrahydro-2-furanyl]carbonyl}amino)propanoic acid; N-(2-amino-1-{[2-(2,6-dichlorophenyl)-6-quinolinyl]methyl}-2-oxoethyl)-2,6-dichlorobenzamide; (2S)-3-[2-(2,6-dichlorophenyl)-6-quinolinyl]-2-({[(2S)-1-(methylsulfonyl)piperidinyl]carbonyl}amino)propanoic acid; 2-[({(2S,3aS,7aS)-1-[(4-methylphenyl)sulfonyl]octahydro-1H-indol-2-yl}carbonyl)amino]-3-[2-(2-bromophenyl)-6-quinolinyl]propanoic acid; 2-({[1-(4-chlorophenyl)cyclopentyl]carbonyl}amino)-3-[2-(2-nitrophenyl)-6-quinolinyl]propanoic acid; 2-[(2,6-dimethoxybenzoyl)amino]-3-[2-(2-nitrophenyl)-6-quinolinyl]propanoic acid; 3-{2-[2-(1,3-benzodioxol-5-yl)-1-methylethyl]-6-quinolinyl}-2-{[2-chloro-4-(methylsulfonyl)benzoyl]amino}propanoic acid; 2-{[2-chloro-4-(methylsulfonyl)benzoyl]amino}-3-[2-(2-methoxyphenyl)-6-quinolinyl]propanoic acid; 2-{[2-chloro-4-(methylsulfonyl)benzoyl]amino}-3-[2-(2,6-dimethoxyphenyl)-6-quinolinyl]propanoic acid; 2-[(2,6-dimethoxybenzoyl)amino]-3-{2-[2-(trifluoromethyl)phenyl]-6-quinolinyl}propanoic acid; 2-[(2,6-difluorobenzoyl)amino]-3-{2-[4-(methylsulfonyl)phenyl]-6-quinolinyl}propanoic acid; 2-[(2-chloro-6-methylbenzoyl)amino]-3-(2-mesityl-6-quinolinyl)propanoic acid; 2-{[2-chloro-4-(methylsulfonyl)benzoyl]amino}-3-(2-mesityl-6-quinolinyl)propanoic acid; 2-{[2-chloro-4-(methylsulfonyl)benzoyl]amino}-3-[2-(2,4-dichlorophenyl)-6-quinolinyl]propanoic acid; 2{[(1-acetyl-2-pyrrolidinyl)carbonyl]amino}-3-[2-(2,4-dichlorophenyl)-6-quinolinyl]propanoic acid; 2-[(2-chloro-6-methylbenzoyl)amino]-3-{2-[5-chloro-1-methyl-3-(trifluoromethyl)-1H-pyrazol-4-yl]-6-quinolinyl}propanoic acid; 2-{[2-chloro-4-(methylsulfonyl)benzoyl]amino}-3-{2-[5-chloro-1-methyl-3-(trifluoromethyl)-1H-pyrazol-4-yl]-6-quinolinyl}propanoic acid; (2S)-2-{[2-chloro-4-(methylsulfonyl)benzoyl]amino}-3-[2-(2,6-dimethylphenyl)-6-quinolinyl]propanoic acid; 3-[2-(2-chloro-6-nitrophenyl)-6-quinolinyl]-2-[(2,6-dichlorobenzoyl)amino]propanoic acid; 2-[(2-chloro-6-methylbenzoyl)amino]-3-[2-(2-chloro-6-nitrophenyl)-6-quinolinyl]propanoic acid; 2-[(2,6-dichlorobenzoyl)amino]-3-[6-(2,6-dimethoxyphenyl)-2-naphthyl]propanoic acid; (−)-methyl 2-[(2,6-dichlorobenzoyl)amino]-3-[6-(2,6-dimethoxyphenyl)-2-naphthyl]propanoate; (−)-2-[(2,6-dichlorobenzoyl)amino]-3-[6-(2,6-dimethoxyphenyl)-2-naphthyl]propanoic acid; 3-[6-(2,6-dimethoxyphenyl)-2-naphthyl]-2-({[(2S)-1-(phenylsulfonyl)pyrrolidinyl]carbonyl}amino)propanoic acid; methyl 3-[6-(2,6-dimethoxyphenyl)-2-naphthyl]-2-({[(2S)-1-(phenylsulfonyl)pyrrolidinyl]carbonyl}amino) propanoate; methyl (2S)-2-{[(2,4-dichloro-6-methyl-3-pyridinyl)carbonyl]amino}-3-[2-(2,6-dichlorophenyl)-6-quinolinyl]propanoate; methyl 2-[(2,6-dichlorobenzoyl)amino]-3-[2-(2,6-dimethoxyphenyl)-6-quinolinyl] propanoate; (1R,3S)-3-[({(1S)-1-carboxy-2-[2-(2,6-dichlorophenyl)-6-quinolinyl]ethyl}amino)carbonyl]-1,2,2-trimethylcyclopentanecarboxylic acid; (2S)-2-({[(4R)-3-acetyl-1,1-dioxido-1,3-thiazolidin-4-yl]carbonyl}amino)-3-[2-(2,6-dichlorophenyl)-6-quinolinyl]propanoic acid; (2S)-2-{[(2,4-dichloro-6-methyl-3-pyridinyl)carbonyl]amino}-3-[2-(2,6-dichlorophenyl)-6-quinolinyl]propanoic acid; methyl (2S)-2-[(2,6-dichlorobenzoyl)amino]-3-[2-(2,6-dimethoxyphenyl)-6-quinolinyl]propanoate; (2S)-2-[(2,6-dichlorobenzoyl)amino]-3-[2-(2,6-dimethoxyphenyl)-6-quinolinyl]propanoic acid; (2S)-3-[2-(2,6-dichlorophenyl)-6-quinolinyl]-2-[({1-[2-(diethylamino)ethyl]cyclopentyl}carbonyl)amino]propanoic acid; (2S)-2-[(2,6-dichlorobenzoyl)amino]-3-[2-(3,5-dichloro-4-pyridinyl)-6-quinolinyl]propanoic acid; (2S)-3-[2-(3,5-dichloro-4-pyridinyl)-6-quinolinyl]-2-({[(2R)-2-methyltetrahydro-2-furanyl]carbonyl}amino)propanoic acid; methyl 3-[2-(2,6-dichlorophenyl)-6-quinolinyl]-2-({[(2S)-1-(phenylsulfonyl)pyrrolidinyl]carbonyl}amino)propanoate; methyl (2S)-2-({[1-(4-chlorophenyl)cyclopentyl]carbonyl}amino)-3-[2-(3,5-dichloro-4-pyridinyl)-6-quinolinyl]propanoate; (2S)-2-({[1-(4-chlorophenyl)cyclopentyl]carbonyl}amino)-3-[2-(3,5-dichloro-4-pyridinyl)-6-quinolinyl]propanoic acid; (2S)-2-({[(2S)-1-benzyl-5-oxopyrrolidinyl]carbonyl}amino)-3-[2-(2,6-dichlorophenyl)-6-quinolinyl]propanoic acid and 3-[2-(2,6-dichlorophenyl)-6-quinolinyl]-2-({[(2S)-1-(phenylsulfonyl)pyrrolidinyl]carbonyl}amino)propanoic acid, and pharmaceutically acceptable salts thereof.

Best compounds are: methyl (2S)-2-[(2,6-dichlorobenzoyl)amino]-3-[2-(2,6-dichlorophenyl)-6-quinolinyl]propanoate; 2-[(2,6-dichlorobenzoyl)amino]-3-[2-(2,6-dichlorophenyl)-6-quinolinyl]propanoic acid; (2S)-2-[(2,6-dichlorobenzoyl)amino]-3-[2-(2,6-dichlorophenyl)-6-quinolinyl]propanoic acid; 2-[(2,6-dichlorobenzoyl)amino]-3-[2-(2,6-dimethoxyphenyl)-6-quinolinyl]propanoic acid; 2-[(2,6-dichlorobenzoyl)amino]-3-[2-(3,5-dichloro-4-pyridinyl)-6-quinolinyl]propanoic acid; methyl 2-[(2,6-dichlorobenzoyl)amino]-3-[2-(3,5-dichloro-4-pyridinyl)-6-quinolinyl]propanoate; methyl (2S)-2-{[2-chloro-4-(methylsulfonyl)benzoyl]amino}-3-[2-(2,6-dichlorophenyl)-6-quinolinyl]propanoate; (2S)-2-[(2-chloro-6-methylbenzoyl)amino]-3-[2-(2,6-dichlorophenyl)-6-quinolinyl]propanoic acid; (2S)-2-{[2-chloro-4-(methylsulfonyl)benzoyl]amino}-3-[2-(2,6-dichlorophenyl)-6-quinolinyl]propanoic acid; (2S)-2-({[1-(4-chlorophenyl)cyclopentyl]carbonyl}amino)-3-[2-(2,6-dichlorophenyl)-6-quinolinyl]propanoic acid; 3-[2-(2,6-dichlorophenyl)-6-quinolinyl]-2-[({(2S)-1-[(4-methylphenyl)sulfonyl]piperidinyl}carbonyl)amino]propanoic acid; (1R,3S)-3-[({1-carboxy-2-[2-(2,6-dichlorophenyl)-6-quinolinyl]ethyl}amino)carbonyl]-1,2,2-trimethylcyclopentanecarboxylic acid; (2S)-2-[(2,6-dichlorobenzoyl)amino]-3-[2-(2-nitrophenyl)-6-quinolinyl]propanoic acid; (2S)-3-[2-(2-chloro-6-fluorophenyl)-6-quinolinyl]-2-[(2,6-dichlorobenzoyl)amino]propanoic acid; (2S)-2-[(2,6-dichlorobenzoyl)amino]-3-[2-(2-methoxy-1-naphthyl)-6-quinolinyl]propanoic acid; (2S)-3-[2-(2-chloro-6-fluorophenyl)-6-quinolinyl]-2-[(2-chloro-6-methylbenzoyl)amino]propanoic acid; (2S)-2-[(2-chloro-6-methylbenzoyl)amino]-3-[2-(2-methoxy-1-naphthyl)-6-quinolinyl]propanoic acid; (2S)-2-{[2-chloro-4-(methylsulfonyl)benzoyl]amino}-3-{2-[2-nitrophenyl]-6-quinolinyl}propanoic acid; (2S)-3-[2-(2-chloro-6- fluorophenyl)-6-quinolinyl]-2-{[2-chloro-4-(methylsulfonyl)benzoyl]amino}propanoic acid; (2S)-2-{[2-chloro-4-(methylsulfonyl)benzoyl]amino}-3-[2-(2-methoxy-1-naphthyl)-6-quinolinyl]propanoic acid; 2-[({(2S,3aS,7aS)-1-[(4-methylphenyl)sulfonyl]octahydro-1H-indol-2-yl}carbonyl)amino]-3-[2-(2,6-dichlorophenyl)-6-quinolinyl]propanoic acid; 3-[2-(2-chloro-6-nitrophenyl)-6-quinolinyl]-2-[(2,6-dichlorobenzoyl)amino]propanoic acid; 2-[(2,6-dichlorobenzoyl)amino]-3-[6-(2,6-dimethoxyphenyl)-2-naphthyl]propanoic acid; (−)-2-[(2,6-dichlorobenzoyl)amino]-3-[6-(2,6-dimethoxyphenyl)-2-naphthyl]propanoic acid; 3-[6-(2,6-dimethoxyphenyl)-2-naphthyl]-2-({[(2S)-1-(phenylsulfonyl)pyrrolidinyl]carbonyl}amino)propanoic acid; methyl (2S)-2-{[(2,4-dichloro-6-methyl-3-pyridinyl)carbonyl]amino}-3-[2-(2,6-dichlorophenyl)-6-quinolinyl]propanoate; methyl 2-[(2,6-dichlorobenzoyl)amino]-3-[2-(2,6-dimethoxyphenyl)-6-quinolinyl]propanoate; (1R,3S)-3-[({(1S)-1-carboxy-2-[2-(2,6-dichlorophenyl)-6-quinolinyl]ethyl}amino)carbonyl]-1,2,2-trimethylcyclopentanecarboxylic acid; (2S)-2-{[(2,4-dichloro-6-methyl-3-pyridinyl)carbonyl]amino}-3-[2-(2,6-dichlorophenyl)-6-quinolinyl]propanoic acid; (2S)-2-[(2,6-dichlorobenzoyl)amino]-3-[2-(2,6-dimethoxyphenyl)-6-quinolinyl]propanoic acid; (2S)-2-[(2,6-dichlorobenzoyl)amino]-3-[2-(3,5-dichloro-4-pyridinyl)-6-quinolinyl] propanoic acid; (2S)-2-([1-(4-chlorophenyl)cyclopentyl]carbonyl)amino)-3-[2-(3,5-dichloro-4-pyridinyl)-6-quinolinyl]propanoic acid; (2S)-2-({[(2S)-1-benzyl-5-oxopyrrolidinyl]carbonyl}amino)-3-[2-(2,6-dichlorophenyl)-6-quinolinyl]propanoic acid and 3-[2-(2,6-dichlorophenyl)-6-quinolinyl]-2-({[(2S)-1-(phenylsulfonyl)pyrrolidinyl]carbonyl}amino)propanoic acid and pharmaceutically acceptable salts thereof.

The best results have been obtained with the following compounds: (2S)-2-[(2,6-dichlorobenzoyl)amino]-3-[2-(2,6-dichlorophenyl)-6-quinolinyl]propanoic acid; (2S)-2-({[(2S)-1-benzyl-5-oxopyrrolidinyl]carbonyl}amino)-3-[2-(2,6-dichlorophenyl)-6-quinolinyl]propanoic acid and (−)-2-[(2,6-dichlorobenzoyl)amino]-3-[6-(2,6-dimethoxyphenyl)-2-naphthyl]propanoic acid.

Many of the compounds of formula I and some of their intermediates have at least one stereogenic center in their structure. This stereogenic center may be present in a R or a S configuration, said R and S notation is used in correspondence with the rules described in Pure Appl. Chem. (1976), 45, 11-30.

In all the above-mentioned scopes, when the carbon atom to which $R^2$ and $R^3$ are attached is asymmetric, it is preferably in the "S"-configuration.

The "pharmaceutically acceptable salts" according to the invention include therapeutically active, non-toxic base and acid salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like (Handbook of Pharmaceutical Salts, P. Heinrich Stahl & Camille G. Wermuth (Eds), Verlag Helvetica Chimica Acta—Zürich, 2002, 329-345).

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like (Handbook of Pharmaceutical Salts, P. Heinrich Stahl & Camille G. Wermuth (Eds), Verlag Helvetica Chimica Acta—Zürich, 2002, 329-345).

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

The invention also relates to all stereoisomeric forms such as enantiomeric and diastereoisomeric forms of the compounds of formula I or mixtures thereof (including all possible mixtures of stereoisomers).

Furthermore certain compounds of formula I which contain alkenyl groups may exist as Z (zusammen) or E (entgegen) isomers. In each instance, the invention includes both mixture and separate individual isomers.

Some of the compounds of formula I may also exist in tautomeric forms. Such forms although not explicitly indicated in the above formula are intended to be included within the scope of the present invention.

With respect to the present invention reference to a compound or compounds is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The invention also includes within its scope pro-drug forms of the compounds of formula I and Its various sub-scopes and sub-groups.

The term "prodrug" as used herein includes compound forms, which are rapidly transformed in vivo to the parent compound according to the invention, for example, by hydrolysis in blood. Prodrugs are compounds bearing groups that are removed by biotransformation prior to exhibiting their pharmacological action. Such groups include moieties that are readily cleaved in vivo from the compound bearing it, which compound after cleavage remains or becomes pharmacologically active. Metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialkylsilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group (T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987).

The protecting group P may be any suitable amine protecting group such as, for example, esters, sulfenyl derivatives, sulfonyl derivatives, alkyl and aryl. Non-limiting examples are methoxycarbonyl, ethoxycarbonyl, tert-butoxycarbonyl (Boc), 9-fluorenylmethoxycarbonyl (Fmoc), 9-(2-sulfo)fluorenylmethoxycarbonyl, 9-(2,7-dibromo)fluorenylmethoxycarbonyl, 2,2,2-trichloroethoxycarbonyl (Troc), 2-phenylethoxycarbonyl, 2-chloroethoxycarbonyl, benzyloxycarbonyl, p-methoxybenzyloxycarbonyl, benzenesulfenyl, 2-nitrobenzenesulfenyl, tosyl, benzenesulfonyl, methyl, tert-butyl, allyl, benzyl, bis(4-methoxyphenyl)methyl or 2,4-dinitrophenyl. For more details concerning deprotection methods, see "Protective Groups in Organic Chemistry", Chapter 2, J. F. W. Omie, Plenum Press, London and New York, 1973 and "Protective Groups in Organic Synthesis", Chapter 7, Th. W. Greene, John Wiley & Sons, 1999.

The present invention concerns also processes for preparing the compounds of formula I.

The compounds of formula I according to their invention can be prepared analogously to conventional methods as understood by the person skilled in the art of synthetic organic chemistry.

The following process description sets forth certain synthesis routes in an illustrative manner. Other alternative and/or analogous methods will be readily apparent to those skilled in this art. As used herein in connection with substituent meanings, "=" means "is" and "≠" means "is other than".

Compounds of formula I may be prepared according to one of the following procedures.

Compounds of formula I wherein X=N, $R^1$≠oxy derivative, $R^2$=—$NHR^4$, wherein $R^4$ has the same definition as described above for compounds of general formula I, and $R^3$=—$COR^7$, with $R^7$=OH or an oxy derivative, may be prepared by oxidation and aromatisation of a derivative of formula II according to the equation:

Oxidation may be carried out with $NaIO_4$ in dioxane/$H_2O$ or in a mixture alcohol/$H_2O$, with $H_2O_2$ in methanol, with tert-butyl hydroperoxide (TBHP) in toluene or alcohol or with meta-chloro-perbenzoic acid (mCPBA) in an inert solvent such as dichloromethane. The following elimination is carried out in a mixture dioxane/$H_2O$, at a temperature between 40 and 80° C.

Compounds of formula IV wherein X=N, $R^1$≠oxy derivative, $R^2$=—$NHR^4$, wherein $R^4$ is P, P being a protecting group, and $R^3$=—$COR^7$, with $R^7$=OH or an oxy derivative, may be prepared according to the same procedure:

Compounds of formula I wherein $R^2$=OH and $R^3$=—$COR^7$, with $R^7$=OH or an oxy derivative, may be prepared by reduction of a compound of formula III according to equation:

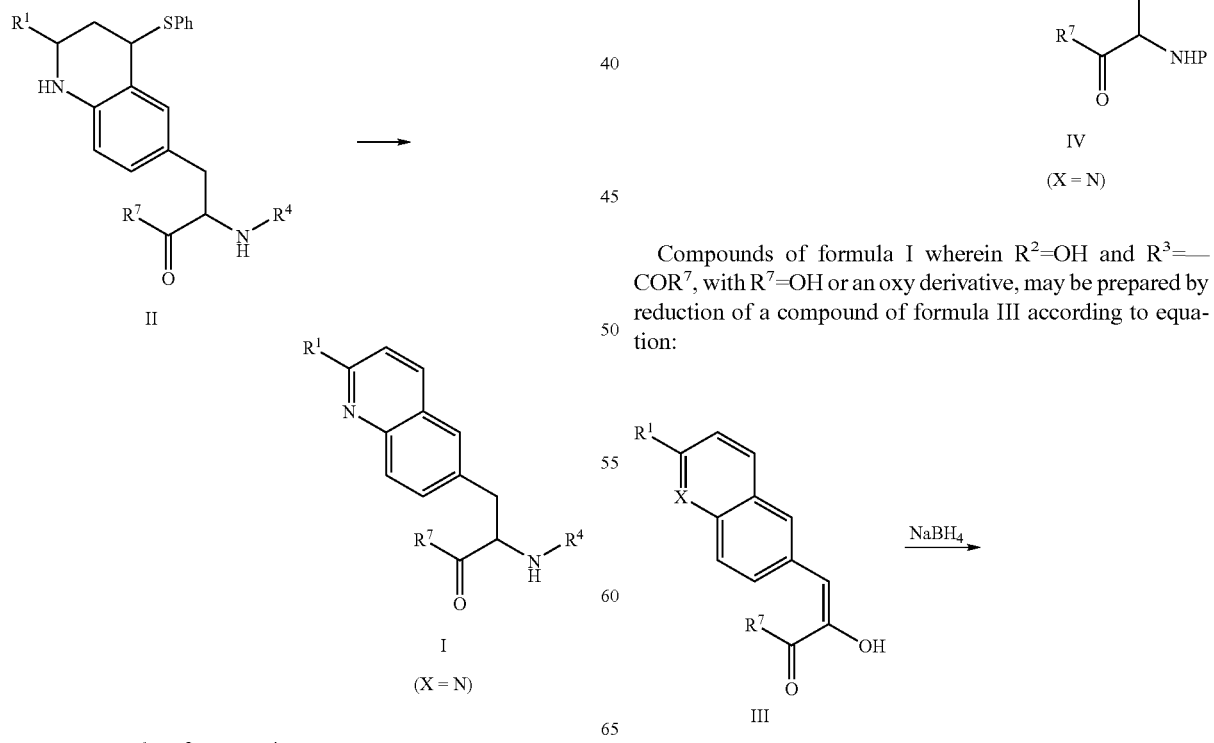

wherein $R^1$, $R^2$ and $R^4$ have the same definitions as described above and Ph represents a phenyl group.

-continued

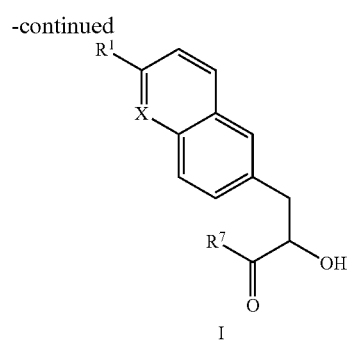

I

This reaction may be carried out according to any procedure known to the person skilled in the art.

Compounds of formula I wherein $R^2=$—$NH_2$ and $R^3=$—$COR^7$, $R^7$ being hydroxy or an oxy derivative, may be obtained by deprotection of compounds of formula IV wherein $R^2=$NHP, P being a protecting group, according to the equation:

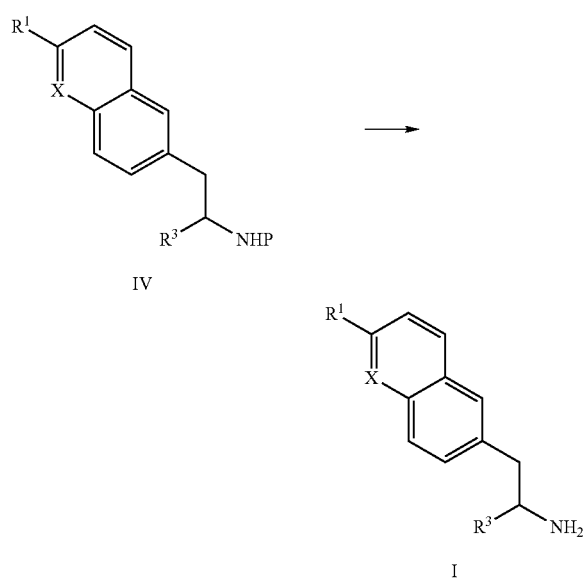

This transformation may be carried out according to any procedure known to the person skilled in the art.

Compounds of formula I wherein $R^3=$—COOH may be prepared by hydrolysis of the corresponding compound of formula I wherein $R^3=$—$COR^7$, $R^7$ being amino, an oxy derivative or an amino derivative.

This transformation may be carried out according to any procedure known to the person skilled in the art.

Compounds of formula I wherein $R^3=$—$COR^7$ with $R^7=$amino derivative may be prepared by reaction of the corresponding compound of formula I wherein $R^3=$—COOH with an amine:

This transformation may be carried out according to any procedure known to the person skilled in the art, or according to the procedure described in S. Conti, Tetrahedron (1994), 50 (47), 13493-13500.

Compounds of formula I wherein $R^3=$—CN may be prepared from the corresponding compound of formula I wherein $R^3=$—$CONH_2$.

This reaction may be carried out according to the procedure described in S. Conti, Tetrahedron (1994), 50 (47), 13493-13500.

Compounds of formula I wherein $R^3=$tetrazole may be prepared from the corresponding compound of formula I wherein $R^3=$cyano according to the equation:

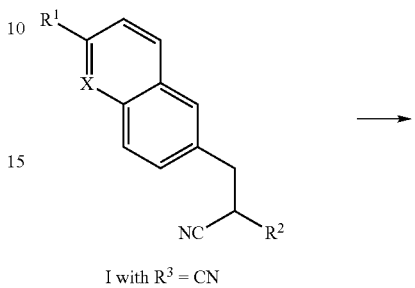

I with $R^3$ = CN

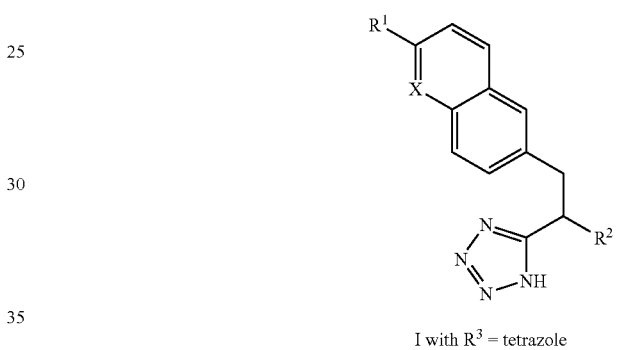

I with $R^3$ = tetrazole

This reaction may be carried out according to the procedure described in J. G. Buchanan, J. Chem. Soc., Perkin Trans. 1 (1992), 20, 2593-2601.

Compounds of formula I wherein $R^3=$—$CH_2OH$ may be prepared by reduction of the corresponding compound of formula I wherein $R^3=$—$COR^7$, $R^7$ being an oxy derivative. This transformation may be carried out according to any procedure known to the person skilled in the art.

Compounds of formula I wherein $R^2=$—$NR^4R^5$, $R^5$ being a C1-4 alkyl, and $R^3=$—$COR^7$, $R^7$ being an oxy derivative, may be prepared by alkylation of the corresponding compound of formula I wherein $R^5=$H. This transformation may be carried out according to any procedure known to the person skilled in the art.

Compounds of formula I wherein $R^2=$—$NHR^4$ and $R^3=$—$COR^7$, $R^7$ being an oxy derivative, may be prepared by acylation, sulfonylation or alkylation of the corresponding compound of formula I wherein $R^2=NH_2$. This transformation may be carried out according to any procedure known to the person skilled in the art.

Compounds of formula I wherein $R^2=$—$OR^4$ and $R^3=$—$COR^7$, $R^7$ being an oxy derivative, may be prepared by alkylation or acylation of the corresponding compound of formula I wherein $R^2=$OH. This transformation may be carried out according to any procedure known to the person skilled in the art.

Compounds of formula II may be prepared by reaction of a compound of formula V with an aldehyde, phenyl vinyl sulfide and an ytterbium triflate derivative according to equation:

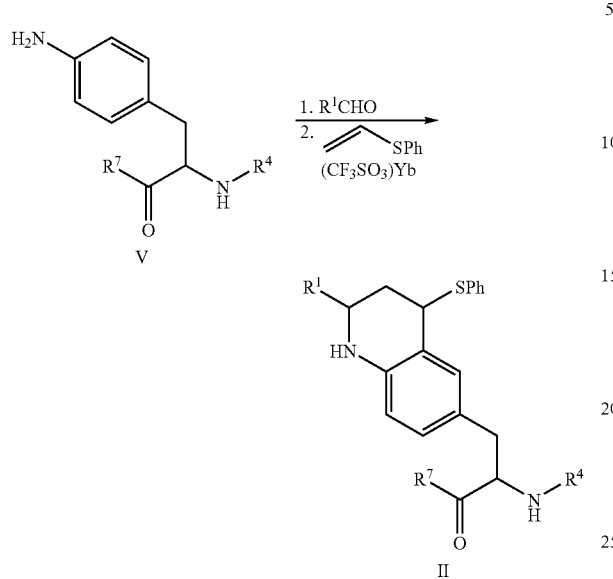

This reaction may be carried out according to the procedure described in S. Kobayashi et al., Synthesis (1995), 1195-1202.

Compounds of formula III may be prepared by deprotection and hydrolysis of a compound of formula VI according to equation:

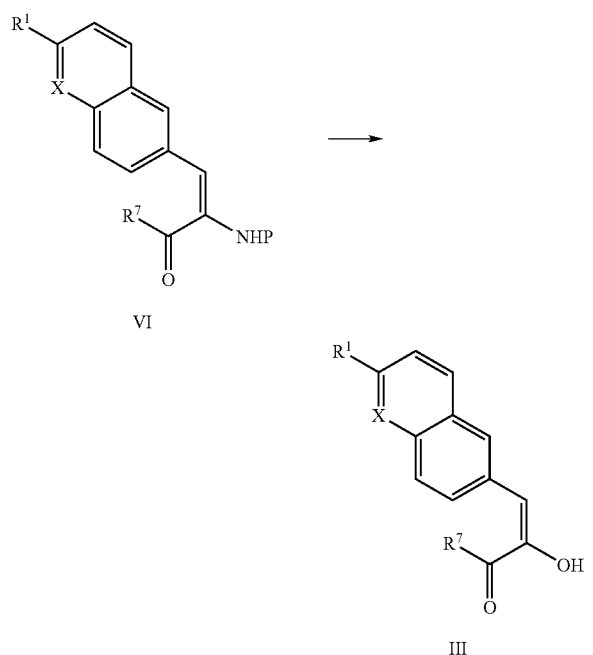

This deprotection followed by hydrolysis of the resulting enamine may be carried out according to procedure described in "Protective Groups in Organic Synthesis", Chapter 4, Th. W. Greene, John Wiley & Sons, 1999.

Compounds of formula IV may be prepared by hydrogenation of a compound of formula VI according to equation:

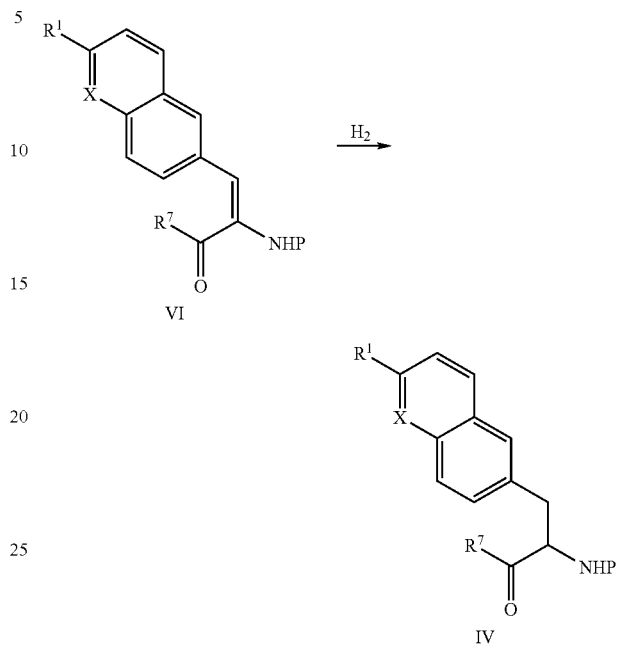

This reaction may be carried out according to the procedure described in M. A. Vela et al., J. Org. Chem. (1990), 55, 2913-2918.

Compounds of formula VI may be prepared by reaction of a compound of formula VII with a derivative of formula VIII according to equation:

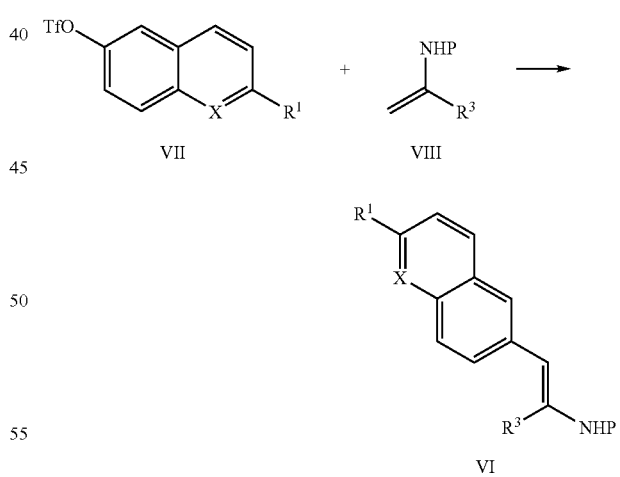

This reaction may be carried out according to the procedure described in A. Arcadi et al, Tetrahedron (1990), 46 (20), 7151-7164.

Compounds of formula VIII are commercially available or, when $R^3$=—$COR^7$, may be prepared by dehydration of 2-amino-protected 3-hydroxypropanoate ester derivatives, for example according to the procedure described in K. Goodall et al., J. Chem. Res. Synop. (2000), 2, 54-55.

Compounds of formula VII may be prepared by modification of a compound of formula IX according to equation:

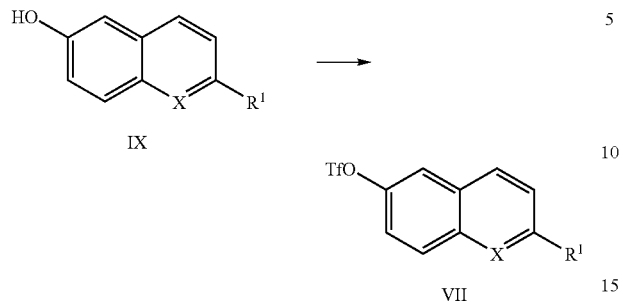

This reaction may be carried out for example according to the procedures described in H. Kosuki et al., Synthesis (1990), 12, 1145-1147; K. Koch, J. Org. Chem. 1994, 59, 1216-1218 or V. Drachsler et al., Synlett (1998), 11, 1207-1208.

For the synthesis of derivatives of formula IX, a derivative of formula X may be deprotected either by catalytic hydrogenation (when $R^1$=oxy derivative) or by treatment with $BBr_3$ (when $R^1 \neq$ oxy derivative) according to equation:

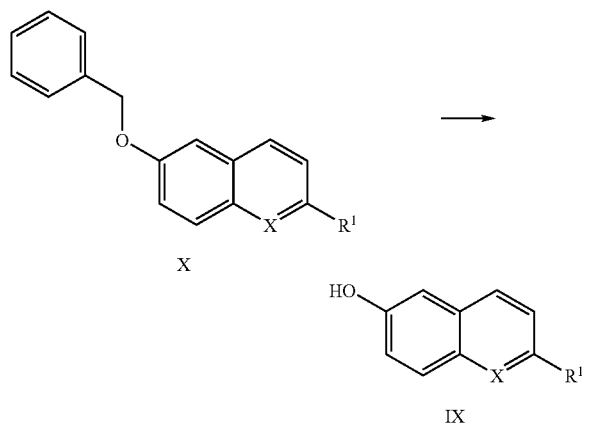

This reaction may be carried out according to procedures described in "Protective Groups in Organic Synthesis", Th. W. Greene, John Wiley & Sons, 1999.

For the synthesis of derivatives of formula X, a derivative of formula XI wherein Hal=Cl or Br is modified either with boronic derivatives ($R^1 \neq$ oxy derivative) or by reaction with alcohol ($R^1$=oxy derivative) according to equation:

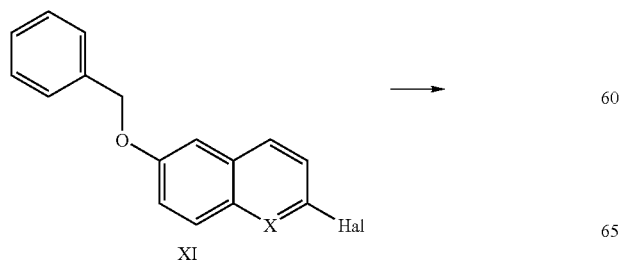

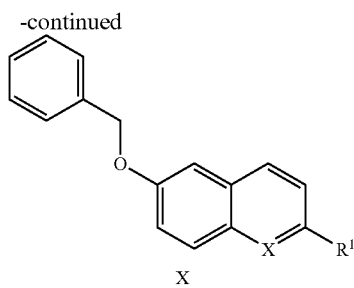

This reaction may be carried out according to the procedure described in N. M. Ali et al., Tetrahedron (1992), 48, 8117-8126.

For the synthesis of derivatives of formula A, the hydroxy group of a derivative of formula XII is protected according to equation:

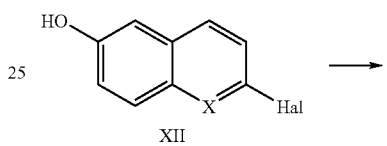

This reaction may be carried out according to procedures described in "Protective Groups in Organic Synthesis", Chapter 2, Th. W. Greene, John Wiley & Sons, 1999.

For the synthesis of derivatives of formula XII wherein X=N, a derivative of formula XIII reacts with $PO(Hal)_3$, for example $POCl_3$ or $POBr_3$, according to equation:

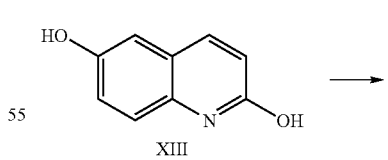

This reaction may be carried out according to the procedure described in Y. Tagawa et al., Heterocycles (1998), 48, 2379-2387 or in M. Fernandez et al., Heterocycles (1994), 38, 2615-2620.

For the synthesis of derivatives of formula XII wherein X=CH, a derivative of formula XIIIa may be deprotected, for example by treatment with $BBr_3$, according to equation:

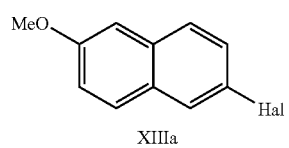

This reaction may be carried out according to procedures described in "Protective Groups in Organic Synthesis", Chapter 2, Th. W. Greene, John Wiley & Sons, 1999.

Compounds of formula V may be prepared by reduction of a compound of formula XIV either by catalytic hydrogenation ($R^7 \neq$ O-Wang Resin) or by treatment with $SnCl_2$ ($R^7$=O-Wang Resin) according to the equation:

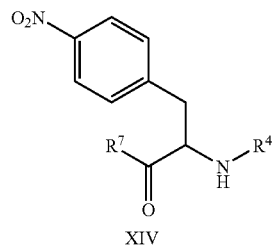

This reaction may be carried out according to any procedure known to the person skilled in the art or to the procedure described in PCT patent application WO9834115-A1 for compounds attached to the Wang Resin.

Compounds of formula XIV may be prepared according to one of the following procedures:

When in formula XIV, $R^7$=oxy derivative, the corresponding compound of formula XIV wherein $R^4$=H is alkylated, acylated or sulfonylated according to equation:

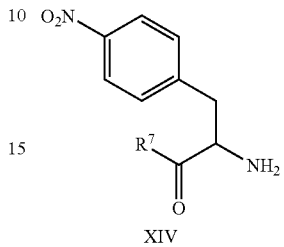

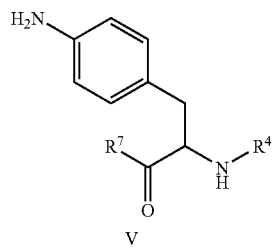

This transformation may be carried out according to any procedure known to the person skilled in the art.

When in formula XIV, $R^2$=$NH_2$ and $R^3$=—$COR^7$, with $R^7$=oxy derivative, the corresponding compound of formula XIV wherein $R^7$=hydroxy is esterified. This transformation may be carried out according to any procedure known to the person skilled in the art.

Compound of formula XIV wherein $R^2$=$NH_2$ and $R^3$=—$COR^7$, with $R^7$=O-Wang Resin may be obtained by deprotection of the corresponding compound of formula XIV wherein $R^2$=NHP, P being a protecting group, and $R^7$=O-Wang Resin. This transformation may be carried out according to any procedure known to the person skilled in the art.

When compounds of formula I present one or several stereogenic centres, and that non-stereoselective methods of synthesis are used, resolution of the mixture of stereoisomers can best be effected in one or several steps, involving generally sequential separation of mixtures of diastereomers into their constituting racemates, using preferably chromatographic separations on achiral or chiral phase in reversed or preferably in direct mode, followed by at least one ultimate step of resolution of each racemate into its enantiomers, using most preferably chromatographic separation on chiral phase in reversed or preferably in direct mode. Alternatively, when partly stereoselective methods of synthesis are used, the ultimate step may be a separation of diastereomers using preferably chromatographic separations on achiral or chiral phase in reversed or preferably in direct mode.

In another embodiment, the present invention concerns also the synthesis intermediates of formula II

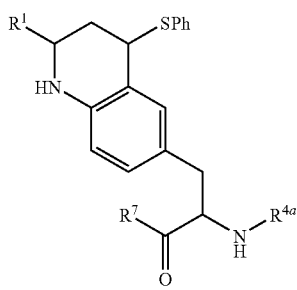

wherein
$R^{4a}$ is $R^4$ or P, $R^4$ being as defined above for compounds of formula I,
$R^1$ is cycloalkyl, aryl, heterocycle, aralkyl, heterocycle-alkyl, or a group of formula:

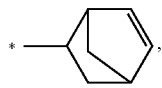

$R^7$ is hydroxy or an oxy derivative,
and P is an amine protecting group.

Preferably, the synthesis intermediates of formula II are selected from the group consisting of methyl 2-[(tert-butoxycarbonyl)amino]-3-[2-(2,6-dichlorophenyl)-4-(phenylsulfanyl)-1,2,3,4-tetrahydro-6-quinolinyl]propanoate; methyl 2-[(tert-butoxycarbonyl)amino]-3-[2-phenyl-4-(phenylsulfanyl)-1,2,3,4-tetrahydro-6-quinolinyl]propanoate; methyl 2-[(tert-butoxycarbonyl)amino]-3-[2-(2,6-dimethoxyphenyl)-4-(phenylsulfanyl)-1,2,3,4-tetrahydro-6-quinolinyl]propanoate; methyl 2-[(2,6-dichlorobenzoyl)amino]-3-[2-(2,6-dichlorophenyl)-4-(phenylsulfanyl)-1,2,3,4-tetrahydro-6-quinolinyl]propanoate; methyl 2-(benzoylamino)-3-[2-(2,6-dichlorophenyl)-4-(phenylsulfanyl)-1,2,3,4-tetrahydro-6-quinolinyl]propanoate; methyl 2-[(2,6-dichlorobenzyl)amino]-3-[2-(2,6-dichlorophenyl)-4-(phenylsulfanyl)-1,2,3,4-tetrahydro-6-quinolinyl]propanoate; methyl 2-[(2,6-dichlorobenzoyl)amino]-3-[2-(2,6-dimethoxyphenyl)-4-(phenylsulfanyl)-1,2,3,4-tetrahydro-6-quinolinyl]propanoate; methyl 2-[(2,6-dichlorobenzoyl)amino]-3-[4-(phenylsulfanyl)-2-(1,3-thiazol-2-yl)-1,2,3,4-tetrahydro-6-quinolinyl]propanoate; methyl 2-[(2,6-dichlorobenzoyl)amino]-3-[2-(3,5-dichloro-4-pyridinyl)-4-(phenylsulfanyl)-1,2,3,4-tetrahydro-6-quinolinyl]propanoate; methyl 2-[(2,6-dichlorobenzoyl)amino]-3-[4-(phenylsulfanyl)-2-(4-pyridinyl)-1,2,3,4-tetrahydro-6-quinolinyl]propanoate; methyl (2S)-2-[(2,6-dichlorobenzoyl)amino]-3-[2-(2,6-dichlorophenyl)-4-(phenylsulfanyl)-1,2,3,4-tetrahydro-6-quinolinyl]propanoate; methyl (2R)-2-[(2,6-dichlorobenzoyl)amino]-3-[2-(2,6-dichlorophenyl)-4-(phenylsulfanyl)-1,2,3,4-tetrahydro-6-quinolinyl]propanoate; methyl (2S)-2-[(tert-butoxycarbonyl)amino]-3-[2-(2,6-dichlorophenyl)-4-(phenylsulfanyl)-1,2,3,4-tetrahydro-6-quinolinyl]propanoate; methyl (2R)-2-[(tert-butoxycarbonyl)amino]-3-[2-(2,6-dichlorophenyl)-4-(phenylsulfanyl)-1,2,3,4-tetrahydro-6-quinolinyl]propanoate; methyl (2S)-2-[(tert-butoxycarbonyl)amino]-3-[2-(2,6-dimethoxyphenyl)-4-(phenylsulfanyl)-1,2,3,4-tetrahydro-6-quinolinyl]propanoate; methyl (2R)-2-[(tert-butoxycarbonyl)amino]-3-[2-(2,6-dimethoxyphenyl)-4-(phenylsulfanyl)-1,2,3,4-tetrahydro-6-quinolinyl]propanoate; methyl (2S)-2-[(tert-butoxycarbonyl)amino]-3-[2-(2,6-dimethylphenyl)-4-(phenylsulfanyl)-1,2,3,4-tetrahydro-6-quinolinyl]propanoate and methyl (2S)-2-[(tert-butoxycarbonyl)amino]-3-[2-(3,5-dichloro-4-pyridinyl)-4-(phenylsulfanyl)-1,2,3,4-tetrahydro-6-quinolinyl]propanoate.

In another embodiment, the present invention concerns also the synthesis intermediates of formula III

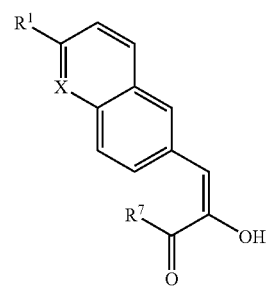

wherein X and $R^1$ are as defined above for compounds of formula I and $R^7$ is hydroxy or an oxy derivative, with the proviso that when X is CH, then $R^1$ is cycloalkyl, aryl, heterocycle, aralkyl, heterocycle-alkyl or a group of formula:

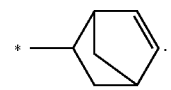

Preferably, the synthesis intermediate of formula III is methyl 3-[2-(2,6-dichlorophenyl)-6-quinolinyl]-2-hydroxy-2-propenoate.

In another embodiment, the present invention concerns also the synthesis intermediates of formula IV

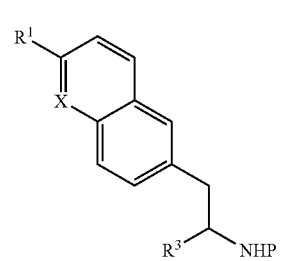

wherein X and $R^1$ are as defined above for compounds of formula I,
$R^3$ is —CO—$R^7$,
$R^7$ is hydroxy or an oxy derivative,
and P is an amine protecting group,
with the proviso that when X is CH, then $R^1$ is cycloalkyl, aryl, heterocycle, aralkyl, heterocycle-alkyl or a group of formula:

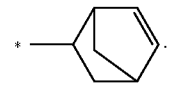

Preferably, the synthesis intermediates of formula IV are selected from the group consisting of methyl 2-[(tert-butoxycarbonyl)amino]-3-[2-(2,6-dichlorophenyl)-6-quinolinyl]propanoate; methyl 2-[(tert-butoxycarbonyl)amino]-3-(2-phenyl-6-quinolinyl)propanoate; methyl 2-[(tert-butoxycarbonyl)amino]-3-[2-(2,6-dimethoxyphenyl)-6-quinolinyl]propanoate; methyl 2-[(tert-butoxycarbonyl)amino]-3-(2-phenoxy-6-quinolinyl)propanoate; methyl 2-[(tert-butoxycarbonyl)amino]-3-[2-(4-chlorophenoxy)-6-quinolinyl]propanoate; methyl 2-[(tert-butoxycarbonyl)amino]-3-(2-methoxy-6-quinolinyl)propanoate; methyl 2-[(tert-butoxycarbonyl)amino]-3-[2-(2-methoxyphenoxy)-6-quinolinyl]propanoate; methyl 2-[(tert-butoxycarbonyl)amino]-3-[2-(2,6-dimethoxyphenoxy)-6-quinolinyl]propanoate; methyl 2-[(tert-butoxycarbonyl)amino]-3-[2-(2,6-dichlorophenoxy)-6-quinolinyl]propanoate; methyl (2S)-2-[(tert-butoxycarbonyl)amino]-3-[2-(2,6-dichlorophenyl)-6-quinolinyl]propanoate; methyl (2R)-2-[(tert-butoxycarbonyl)amino]-3-[2-(2,6-dichlorophenyl)-6-quinolinyl]propanoate; methyl (2S)-2-[(tert-butoxycarbonyl)amino]-3-[2-(2,6-dimethoxyphenyl)-6-quinolinyl]propanoate; methyl (2R)-2-[(tert-butoxycarbonyl)amino]-3-[2-(2,6-dimethoxyphenyl)-6-quinolinyl]propanoate; methyl (2S)-2-[(tert-butoxycarbonyl)amino]-3-[2-(2,6-dimethylphenyl)-6-quinolinyl]propanoate; methyl (2S)-2-[(tert-butoxycarbonyl)amino]-3-[2-(3,5-dichloro-4-pyridinyl)-6-quinolinyl]propanoate; methyl 2-(acetylamino)-3-[6-(2,6-dimethoxyphenyl)-2-naphthyl]propanoate and ethyl 2-(acetylamino)-3-[6-(2,6-dichlorophenyl)-2-naphthyl]propanoate.

In another embodiment, the present invention concerns also the synthesis intermediates of formula VI

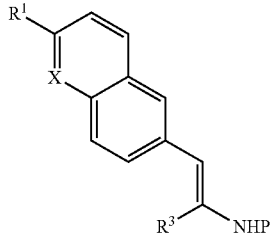

VI wherein X and $R^1$ are as defined above for compounds of formula I,
$R^3$ is —CO—$R^7$.
$R^7$ is hydroxy or an oxy derivative,
and P is an amine protecting group,
with the proviso that when X is CH, then $R^1$ is cycloalkyl, aryl, heterocycle, aralkyl, heterocycle-alkyl or a group of formula:

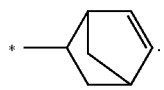

Preferably, the synthesis intermediates of formula VI are selected from the group consisting of methyl 2-[(tert-butoxycarbonyl)amino]-3-(2-phenoxy-6-quinolinyl)-2-propenoate; methyl 2-[(tert-butoxycarbonyl)amino]-3-[2-(4-chlorophenoxy)-6-quinolinyl]-2-propenoate; methyl 2-[(tert-butoxycarbonyl)amino]-3-(2-methoxy-6-quinolinyl)-2-propenoate; methyl 2-[(tert-butoxycarbonyl)amino]-3-[2-(2-methoxyphenoxy)-6-quinolinyl]-2-propenoate; methyl 2-[(tert-butoxycarbonyl)amino]-3-[2-(2,6-dimethoxyphenoxy)-6-quinolinyl]-2-propenoate; methyl 2-[(tert-butoxycarbonyl)amino]-3-[2-(2,6-dichlorophenoxy)-6-quinolinyl]-2-propenoate; methyl 2-[(tert-butoxycarbonyl)amino]-3-[2-(2,6-dichlorophenyl)-6-quinolinyl]-2-propenoate and methyl (2-(acetylamino)-3-[6-(2,6-dimethoxyphenyl)-2-naphthyl]-2-propenoate.

In another embodiment, the present invention concerns also the synthesis intermediates selected from the group consisting of methyl 2-[(2,6-dichlorobenzoyl)amino]-3-(4-nitrophenyl)propanoate; methyl 2-[(2,6-dichlorobenzyl)amino]-3-(4-nitrophenyl)propanoate; methyl 3-(4-aminophenyl)-2-[(2,6-dichlorobenzoyl)amino]propanoate; methyl 3-(4-aminophenyl)-2-[(2,6-dichlorobenzyl)amino]propanoate; 6-(benzyloxy)-2-chloroquinoline; 6-(benzyloxy)-2-phenoxyquinoline; 6-(benzyloxy)-2-(4-chlorophenoxy)quinoline; 6-(benzyloxy)-2-methoxyquinoline; 6-(benzyloxy)-2-(2-methoxyphenoxy)quinoline; 6-(benzyloxy)-2-(2,6-dimethoxyphenoxy)quinoline; 6-(benzyloxy)-2-(2,6-dichlorophenoxy)quinoline; 2-phenoxy-6-quinolinol; 2-(4-chlorophenoxy)-6-quinolinol; 2-methoxy-6-quinolinol; 2-(2-methoxyphenoxy)-6-quinolinol; 2-(2,6-dimethoxyphenoxy)-6-quinolinol; 2-(2,6-dichlorophenoxy)-6-quinolinol; 2-phenoxy-6-quinolinyl trifluoromethanesulfonate; 2-(4-chlorophenoxy)-6-quinolinyl trifluoromethanesulfonate; 2-methoxy-6-quinolinyl trifluoromethanesulfonate; 2-(2-methoxyphenoxy)-6-quinolinyl trifluoromethanesulfonate; 2-(2,6-dimethoxyphenoxy)-6-quinolinyl trifluoromethanesulfonate; 2-(2,6-dichlorophenoxy)-6-quinolinyl trifluoromethanesulfonate; 6-(benzyloxy)-2-(2,6-dichlorophenyl)quinoline; 2-(2,6-dichlorophenyl)-6-quinolinol; 2-(2,6-dichlorophenyl)-6-quinolinyl trifluoromethanesulfonate; 2-(benzyloxy)-6-(2,6-dimethoxyphenyl)naphthalene; 6-(2,6-dimethoxyphenyl)-2-naphthol and 6-(2,6-dimethoxyphenyl)-2-naphthyl trifluoromethanesulfonate.

It has now been found that compounds of formula I and their pharmaceutically acceptable salts are useful in a variety of pharmaceutical indications.

For example, the compounds according to the invention are useful for the treatment of asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, and atherosclerosis.

Thus, the present invention, in a further aspect, concerns the use of a compound of formula I or a pharmaceutically acceptable salt thereof for the manufacture of a medicament for the treatment of disorders such as mentioned above.

In particular, the present invention concerns the use of a compound of formula I or a pharmaceutically acceptable salt thereof, for the manufacture of a medicament for the treatment of VLA-4 dependent inflammatory diseases such as for example asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, and atherosclerosis.

The compounds of the invention are useful for treating conditions in which there is an influx of leukocytes in the tissues. These conditions include preferably asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, and atherosclerosis. The compounds exhibit this biological activity by inhibiting the VCAM/VLA-4 interaction.

Subjects in need of treatment for a VLA-4 dependent inflammatory condition, preferably asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, and atherosclerosis, can be treated by administering to the patient an effective amount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, intramuscularly or topically, in liquid, cream, gel or solid form, via a buccal or nasal spray, or aerosol.

The invention further concerns the use of the compounds of formula I for the manufacture of a medicament for therapeutic application. In particular, the invention concerns the use of the compounds of formula I for the manufacture of a medicament useful for treating conditions in which there is likely to be a VLA-4 dependent inflammatory component. The invention concerns the use of the compound of formula I for the manufacture of a medicament useful for treating asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, and atherosclerosis.

The invention further concerns the compounds of formula I for use as medicaments. The invention concerns the compounds of formula I for use as a medicament for treating asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, and atherosclerosis.

The activity and properties of the active compounds, oral availability and stability in vitro or in vivo can vary significantly among the optical isomers of the disclosed compounds.

In a preferred embodiment, the active compound is administered in an enantiomerically enriched form, i.e., substantially in the form of one isomer.

The present invention also concerns a method for treating VLA-4 dependent inflammatory condition (preferably asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, and atherosclerosis) in a mammal in need of such treatment, comprising administering a therapeutic dose of at least one compound of formula I or a pharmaceutically acceptable salt thereof to a patient.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 0.01 to 1000 mg, preferably 0.05 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The activity of the compounds of formula I, or their pharmaceutically acceptable salts, as VLA-4 antagonists can be determined in a cell adhesion assay. The objective of this test is to evaluate the anti-VLA-4 potential of a compound by measuring its inhibitory effect on the adhesion of a VLA-4 expressing cell line to human recombinant VCAM (adapted from A. L. Akeson et al., J. Immunol. Methods (1993), 163, 181-185).

Results obtained with compounds of formula I are indicative of a strong pharmacological effect.

For treating diseases, compounds of formula I or their pharmaceutically acceptable salts, may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof, is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, or parenteral.

Pharmaceutical compositions comprising compounds according to the invention can, for example, be administered orally or parenterally, i.e., intravenously, intramuscularly, subcutaneously or intrathecally.

Pharmaceutical compositions suitable for oral administration can be solids or liquids and can, for example, be in the form of tablets, pills, dragees, gelatine capsules, solutions, syrups, and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

For the preferred oral compositions, the daily dosage is in the range 0.01 to 1000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 0.01 mg to 1000 mg of compounds of formula I.

The daily dose can fall within a wide range of dosage units of compound of formula I and is generally in the range 0.01 to 1000 mg. However, it should be understood that the specific doses could be adapted to particular cases depending on the individual requirements, at the physician's discretion.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in DMSO-$d_6$ (or CDCl$_3$) solution at a probe temperature of 313 K or 300 K and at a concentration of 20 mg/ml. The instrument is locked on the deuterium signal of DMSO-$d_6$ (or CDCl$_3$). Chemical shifts are given in ppm downfield from TMS taken as internal standard.

HPLC analyses are performed using one of the following systems:
- an Agilent 1100 series HPLC system mounted with an INERTSIL ODS 3 C18, DP 5 μm, 250×4.6 mm column. The gradient ran from 100% solvent A (acetonitrile, water, H$_3$PO$_4$ (5/95/0.001, v/v/v)) to 100% solvent B (acetonitrile, water, H$_3$PO$_4$ (95/5/0.001, v/v/v)) in 6 min with a hold at 100% B of 4 min. The flow rate is set at 2.5 ml/min. The chromatography is carried out at 35° C.
- a HP 1090 series HPLC system mounted with a HPLC Waters Symmetry C18, 250×4.6 mm column. The gradient ran from 100% solvent A (MeOH, water, H$_3$PO$_4$ (15/85/0.001M, v/v/M)) to 100% solvent B (MeOH, water, H$_3$PO$_4$ (85/15/0.001 M, v/v/M)) in 10 min with a hold at 100% B of 10 min. The flow rate is set at 1 ml/min. The chromatography is carried out at 40° C.

Mass spectrometric measurements in LC/MS mode are performed as follows:

HPLC Conditions

Analyses are performed using a WATERS Alliance HPLC system mounted with an INERTSIL ODS 3, DP 5 μm, 250×4.6 mm column.

The gradient ran from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μgr/ml. API spectra (+ or −) are performed using a FINNIGAN (San Jose, Calif., USA) LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Specific rotation is recorded on a Perkin-Elmer 341 polarimeter. The angle of rotation is recorded at 25° C. on 1% solutions in MeOH. For some molecules, the solvent is CH$_2$Cl$_2$ or DMSO, due to solubility problems.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 μm, 100*500 mm column using an in-house build instrument with various mixtures of lower alcohols and C5 to C8 linear, branched or cyclic alkanes at t 350 ml/min. Solvent mixtures as described in individual procedures.

The following abbreviations are used in the examples:
aa Amino acid
Ac —C(=O)CH$_3$
AcOEt Ethyl acetate
AcOH Acetic acid
Boc tert-butoxycarbonyl
CH$_3$CN Acetonitrile
ClCOOEt or ClCO$_2$Et Ethyl chloroformate
DIPEA Diisopropylethylamine
DMF N,N-Dimethylformamide
Equ. Equivalent
Et$_3$N Triethylamine
HATU O-7-azabenzotriazol-1-yl-N,N,N',N'tetramethyluronium hexafluoro-phosphate
HOBT 1-hydroxybenzotriazole
mCPBA meta-chloro-perbenzoic acid
PrepLC Preparative Liquid Chromatography
RT Room temperature
TBTU O-benzotriazol-1-yl-N,N,N',N'-tetramethyluronium tetrafluoroborate
Tf— Trifluoromethylsulfonyl group
Tf$_2$O Trifluoromethanesulfonic anhydride
TFA Trifluoroacetic acid
THF Tetrahydrofuran

EXAMPLE 1
Quinolinyl Derivatives: Racemic Synthesis
1.1 Synthesis of 2-[(2,6-dichlorobenzoyl)amino]-3-[2-(2,6-dichlorophenyl)-6-quinolinyl]propanoic acid 38
Scheme 1:
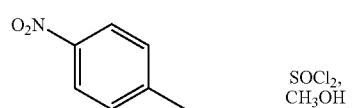
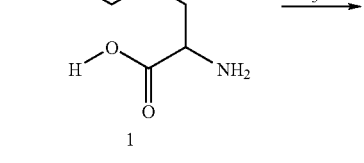
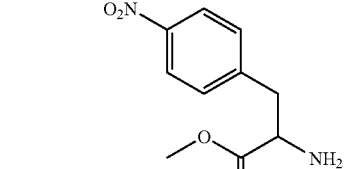
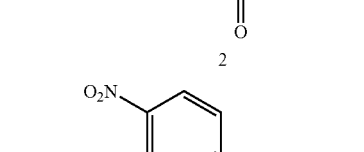
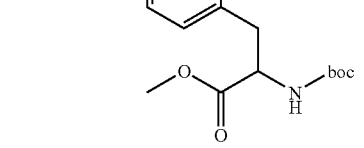
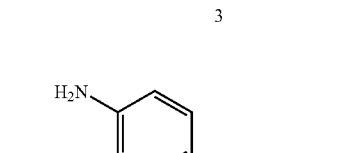
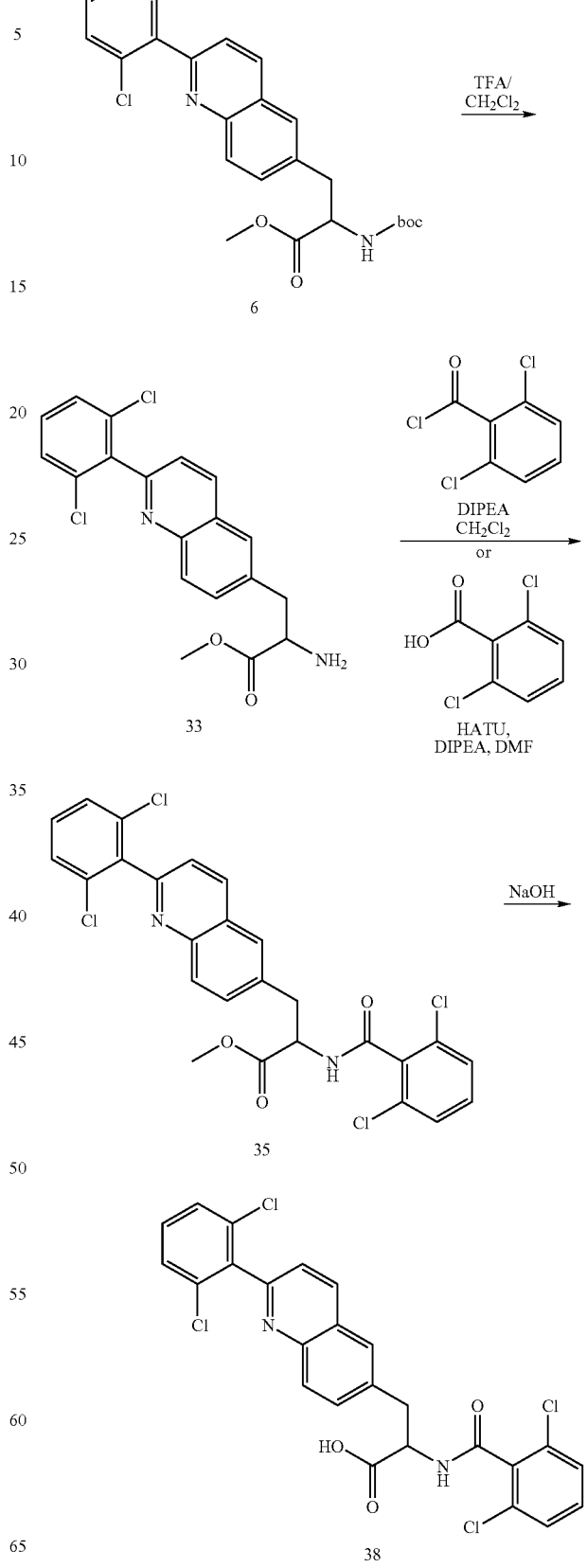

1.1.1 Synthesis of methyl 2-amino-3-(4-nitrophenyl)propanoate 2

To a suspension of 4-nitrophenylalanine 1 (25 g) in methanol (10 ml/g) at 0° C. is added $SOCl_2$ (2 equ.). After 30 minutes, the reaction is stirred at room temperature for 1 night. Volatiles are then evaporated and the residue is diluted in water. The solution is alkalinized with NaOH 2N and extracted with $CH_2Cl_2$. The organic phase is dried over $MgSO_4$ and evaporated. No further purification is needed.
Yield: 79%.
MS ($MH^+$): 225.

1.1.2 Synthesis of methyl 2-[(tert-butoxycarbonyl)amino]-3-(4-nitrophenyl)propanoate 3

Methyl 2-amino-3-(4-nitrophenyl)propanoate 2 (21 g) and powdered NaOH (1.2 equ.) are suspended in THF (5 ml/g). $Boc_2O$ (1.2 equ.) solubilized in THF (2 ml/g) is added slowly to the solution. The mixture is stirred for 1 h at room temperature, poured into water and then extracted with AcOEt (2×900 ml). The organic phase is dried over $MgSO_4$ and evaporated to dryness. No further purification is needed.
Yield: 100%.
MS ($MH^+$): 325.

1.1.3 Synthesis of methyl 3-(4-aminophenyl)-2-[(tert-butoxycarbonyl)amino]propanoate 4

To a solution of methyl 2-[(tert-butoxycarbonyl)amino]-3-(4 nitrophenyl)propanoate 3 (69.4 g) and $NH_4HCO_2$ (6.5 equ.) in $CH_3OH$ (20 ml/g) is added 5% Pd/C (15% in weight, 10 g). The temperature rises to 40° C. and then decreases. After stirring for 2 h at room temperature, the solution is filtered over celite and the solvent is evaporated. The residue is diluted in AcOEt and washed 3 times with water. The organic phase is dried over $MgSO_4$ and evaporated to dryness. No further purification is needed.
Yield: 100%.
MS ($MH^+$): 285.

1.1.4 Synthesis of methyl 2-[(tert-butoxycarbonyl)amino]-3-[2-(2,6-dichlorophenyl)-4-(phenylsulfanyl)-1,2,3,4-tetrahydro-6-quinolinyl]propanoate 5

Methyl 3-(4-aminophenyl)-2-[(tert-butoxycarbonyl)amino]propanoate 4 (38.2 g) solubilized in a 50/50 mixture of $CH_3CN/CH_2Cl_2$ is added, at room temperature, to a mixture of $Yb(OTf)_3$ (0.05 equ.) and $MgSO_4$ (3 equ.) in $CH_3CN/CH_2Cl_2$ (50/50,400 ml). Solid 2,6-dichlorobenzaldehyde (1.1 equ.) is then added and after 2 h, phenyl vinyl sulfide (1.2 equ.) is added dropwise. After one night, insolubles are filtered and the solvents evaporated. The residue is purified by silica gel chromatography using hexane mixture/AcOEt 80/20 as eluent to give methyl 2-[(tert-butoxycarbonyl)amino]-3-[2-(2,6-dichlorophenyl)-4-(phenylsulfanyl)-1,2,3,4-tetrahydro-6-quinolinyl]propanoate 5.
Yield: 81%.
MS ($MH^+$): 587/589/591.

Methyl 2-[(tert-butoxycarbonyl)amino]-3-[2-phenyl-4-(phenylsulfanyl)-1,2,3,4-tetrahydro-6-quinolinyl]propanoate 5a and methyl 2-[(tert-butoxycarbonyl)amino]-3-[2-(2,6-dimethoxyphenyl)-4-(phenylsulfanyl)-1,2,3,4-tetrahydro-6-quinolinyl]propanoate 5b (MS ($MH^+$): 579) can be synthesized according to the same method.

1.1.5 Synthesis of methyl 2-[(tert-butoxycarbonyl)amino]-3-[2-(2,6-dichlorophenyl)-6-quinolinyl]propanoate 6

Methyl 2-[(tert-butoxycarbonyl)amino]-3-[2-(2,6-dichlorophenyl)-4-(phenylsulfanyl)-1,2,3,4-tetrahydro-6-quinolinyl]propanoate 5 (32 g) is solubilized in dioxane (10 ml/g of 5). Water (0.5 ml/g of 5) and solid $NaIO_4$ (1.1 equ.) are added, and the mixture is stirred at 80° C. for 40 h. The solvent is evaporated and the resulting mixture is extracted with $CH_2Cl_2$. The insoluble part is filtered and after evaporation, the residue is purified by silica gel chromatography using Hexane mixture/AcOEt 75/25 as eluent.
Yield: 88%.
MS ($MH^+$): 475/477/479.

Methyl 2-[(tert-butoxycarbonyl)amino]-3-(2-phenyl-6-quinolinyl)propanoate 6a and methyl 2-[(tert-butoxycarbonyl)amino]-3-[2-(2,6-dimethoxyphenyl)-6-quinolinyl]propanoate 6b (MS ($MH^+$): 467) can be synthesized according to the same method.

1.1.6 Synthesis of methyl 2-amino-3-[2-(2,6-dichlorophenyl)-6-quinolinyl]propanoate 33

9.15 g of methyl 2-[(tert-butoxycarbonyl)amino]-3-[2-(2,6-dichlorophenyl)-6-quinolinyl]propanoate 6 are solubilized in $CH_2Cl_2$ (50 ml). TFA (50 ml) is added at 0° C., and the mixture is stirred at RT for 6 h. After evaporation of the solvent, the residue is triturated in diethyl ether and cooled at 5° C. The solid product 33 is obtained by filtration.
Yield: 89%.
MS ($MH^+$): 375/377/379.

1.1.7 Synthesis of methyl 2-[(2,6-dichlorobenzoyl)amino]-3-[2-(2,6-dichlorophenyl)-6-quinolinyl]propanoate 35

To 23.38 g of methyl 2-amino-3-[2-(2,6-dichlorophenyl)-6-quinolinyl]propanoate 33 (0.2 TFA salt) in $CH_2Cl_2$ (50 ml) are added, at 0° C., triethylamine (22 ml) and 2,6-dichlorobenzoyl chloride (6.22 ml) dissolved in $CH_2Cl_2$ (6 ml). The reaction is stirred at RT for 2 h. The organic phase is washed with water, dried over $MgSO_4$ and evaporated under vacuum. The residue is purified by silica gel chromatography using $CH_2Cl_2$/Hexane 95/5 as eluent.
Yield: 96%.
MS ($MH^+$): 547/549/551.

1.1.8 Synthesis of 2-[(2,6-dichlorobenzoyl)amino]-3-[2-(2,6-dichlorophenyl)-6-quinolinyl]propanoic acid 38

Methyl 2-[(2,6-dichlorobenzoyl)amino]-3-[2-(2,6-dichlorophenyl)-6-quinolinyl]propanoate 35 (0.2 g) is solubilized in $CH_3CN/H_2O$/NaOH 0.1N (4 ml/0.22 ml/3.65 ml). After 1 night at room temperature, 10% $KHSO_4$ (9 ml) is added and $CH_3CN$ is evaporated. The resulting aqueous phase is extracted two times with AcOEt (2×12 ml). The organic phase is washed with brine, dried over $MgSO_4$ and evaporated under vacuum. The residue is purified by silica gel chromatography using $CH_2Cl_2/CH_3OH/NH_4OH$ cc (90/10/1) as eluent.
Yield: 77%.
MS ($MH^+$): 533/535/537.

1.2 Synthesis of methyl 2-[(2,6-dichlorobenzoyl)amino]-3-[2-(2,6-dichlorophenyl)-6-quinolinyl]propanoate 35 and methyl 2-[(2,6-dichlorobenzyl)amino]-3-[2-(2,6-dichlorophenyl)-6-quinolinyl]propanoate 41

Scheme 2:
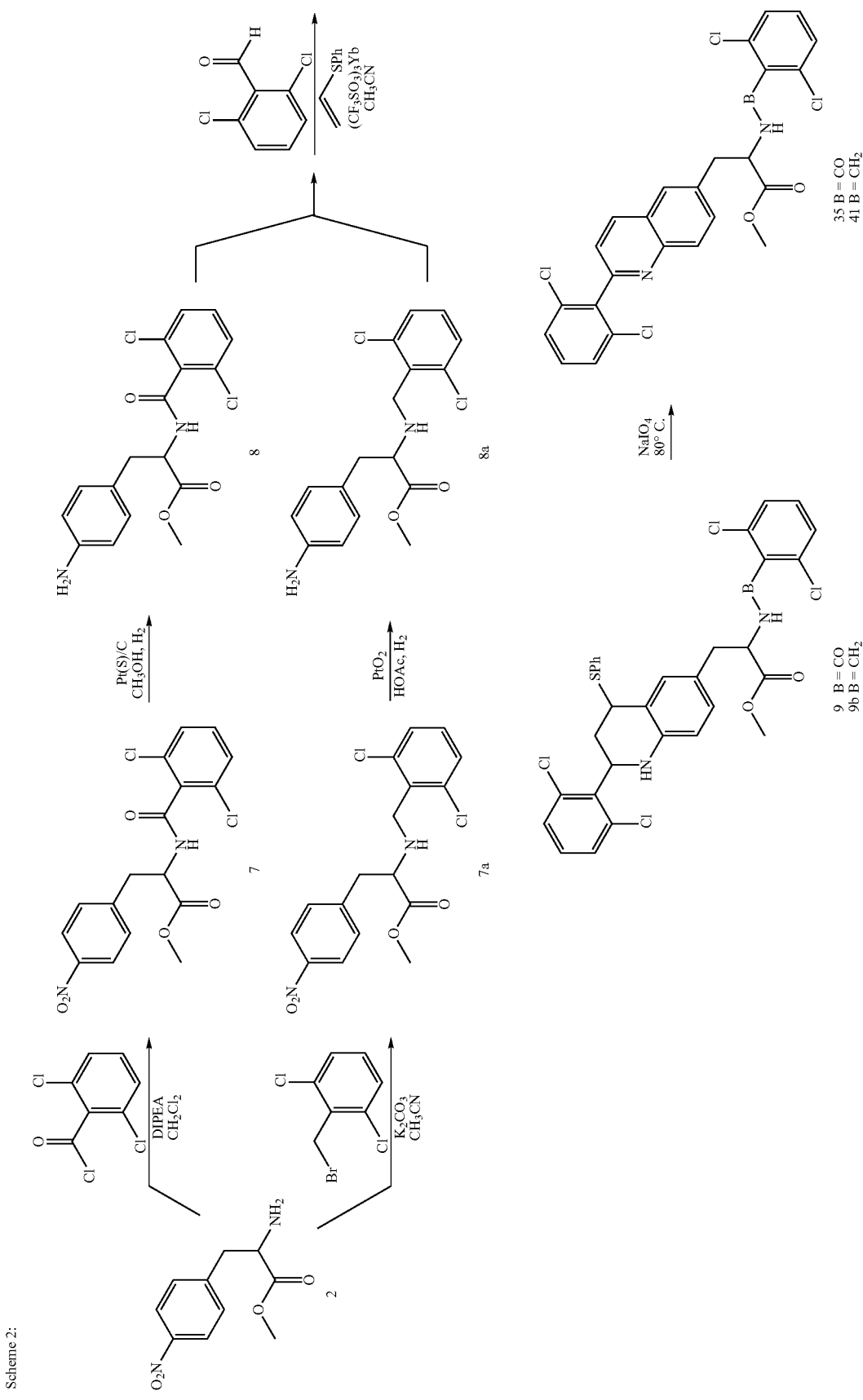

1.2.1 Synthesis of methyl 2-[(2,6-dichlorobenzoyl) amino]-3-(4-nitrophenyl)propanoate 7

To a solution of methyl 2-amino-3-(4-nitrophenyl)propanoate 2 (9.5 g) in $CH_2Cl_2$ (40 ml) is added, at 0° C., 2,6-dichlorobenzoyl chloride (7.71 g) dissolved in $CH_2Cl_2$ (40 ml). DIPEA (2 equ.) is then added dropwise to the mixture at 0° C. The reaction is then risen at RT and pH is brought to 7-8 by addition of DIPEA. The mixture is stirred for 2 h, then evaporated and the residue is placed in AcOEt (175 ml). The organic phase is washed one time with 5% $NaHCO_3$ (150 ml), one time with water, one time with 10% $KHSO_4$ (150 ml) and one time with brine, dried over $MgSO_4$ and evaporated. No further purification is needed.

Yield: 96%.

MS ($MH^+$): 397/399/401.

1.2.2 Synthesis of methyl 2-[(2,6-dichlorobenzyl) amino]-3-(4-nitrophenyl)propanoate 7a To a solution of methyl 2-amino-3-(4-nitrophenyl)propanoate 2 (6 g) in $CH_3CN$ (30 ml) is added, pulverized $K_2CO_3$ (11.095 g), 2,6-dichlorobenzyl bromide (6.42 g). The mixture is stirred at RT for 6 h then filtrated on decalite and evaporated. The residue is placed in $CH_2Cl_2$ (100 ml) and washed three time with water (100 ml) dried over $MgSO_4$ and evaporated. The residue is purified by silica gel chromatography using AcOEt/hexane 10/90 as eluent.

Yield: 74%.

MS ($MH^+$): 383/385/387.

1.2.3 Synthesis of methyl 3-(4-aminophenyl)-2-[(2, 6-dichlorobenzoyl)amino]propanoate 8

Methyl 2-[(2,6-dichlorobenzoyl)amino]-3-(4-nitrophenyl)propanoate 7 (7 g) is solubilized in $CH_3OH$ in presence of Pt(S)/C (5% in weight). $H_2$ pressure is then applied at RT for 2 h. The catalyst is filtered over celite and the solvent is evaporated to give methyl 3-(4-aminophenyl)-2-[(2,6-dichlorobenzoyl)amino]propanoate 8.

Yield: 100%.

MS ($MH^+$): 367/369/371.

1.2.4 Synthesis of methyl 3-(4-aminophenyl)-2-[(2, 6-dichlorobenzyl)amino]propanoate 8a To methyl 2-[(2,6-dichlorobenzyl)amino]-3-(4-nitrophenyl)propanoate 7a (8.2 g) solubilized in $CH_3COOH$ in an ultrasonic bath is added $PtO_2$ hydrate (typical Pt content 79-84%) (0.02 g). A $H_2$ pressure of 15 psi is then applied at RT and consumed after 5 min. An other $H_2$ pressure of 10 psi is then applied at RT and consumed after 5-10 min. A $H_2$ pressure of 10 psi is again applied at RT and a stabilization is observed after 5 min. The catalyst is filtered over celite under nitrogen and washed with $CH_3COOH$. The solvent is evaporated. AcOEt (200 ml) is added to the residue and this organic phase is washed three times with saturated $NaHCO_3$ (200 ml), dried over $MgSO_4$ and evaporated. The residue is purified by silica gel chromatography using $CH_2Cl_2/CH_3OH/NH_4OH$ cc (99.75/0.25/0.025) as eluent.

Yield: 62%.

MS ($MH^+$): 353/355/357.

1.2.5 Synthesis of methyl 2-[(2,6-dichlorobenzoyl) amino]-3-[2-(2,6-dichlorophenyl)-4-(phenylsulfanyl)-1,2,3,4-tetrahydro-6-quinolinyl]propanoate 9

Methyl 2-[(2,6-dichlorobenzoyl)amino]-3-[2-(2,6-dichlorophenyl)-4-(phenylsulfonyl)-1,2,3,4-tetrahydro-6-quinolinyl]propanoate 9 is prepared according to the method described for compound 5 in scheme 1.

Yield: 81%.

MS ($MH^+$): 659/661.

Methyl 2-(benzoylamino)-3-[2-(2,6-dichlorophenyl)-4-(phenylsulfanyl)-1,2,3,4-tetrahydro-6-quinolinyl]propanoate 9a, methyl 2-[(2,6-dichlorobenzoyl)amino]-3-[2-(2,6-dichlorophenyl)-4-(phenylsulfanyl)-1,2,3,4-tetrahydro-6-quinolinyl]propanoate 9b (MS ($MH^+$): 645/647/649), methyl 2-[(2,6-dichlorobenzoyl)amino]-3-[2-(2,6-dimethoxyphenyl)-4-(phenylsulfanyl)-1,2,3,4-tetrahydro-6-quinolinyl] propanoate 9c (MS ($MH^+$): 651/653/655), methyl 2-[(2,6-dichlorobenzoyl)amino]-3-[4-(phenylsulfanyl)-2-(1,3-thiazol-2-yl)-1,2,3,4-tetrahydro-6-quinolinyl]propanoate 9d (MS ($MH^+$): 596/598/600), methyl 2-[(2,6-dichlorobenzoyl)amino]-3-[2-(3,5-dichloro-4-pyridinyl)-4-(phenylsulfanyl)-1,2,3,4-tetrahydro-6-quinolinyl]propanoate 9e (MS ($MH^+$): 658/660/662) and methyl 2-[(2,6-dichlorobenzoyl)amino]-3-[4-(phenylsulfanyl)-2-(4-pyridinyl)-1,2,3,4-tetrahydro-6-quinolinyl]propanoate 9f (MS ($MH^+$): 590/592/594) can be synthesized according to the same method.

1.2.6 Synthesis of methyl 2-[(2,6-dichlorobenzoyl) amino]-3-[2-(2,6-dichlorophenyl)-6-quinolinyl]propanoate 35

Methyl 2-[(2,6-dichlorobenzoyl)amino]-3-[2-(2,6-dichlorophenyl)-6-quinolinyl]propanoate 35 is prepared according to the method described for compound 6 in scheme 1.

MS ($MH^+$): 547/549/551.

Methyl 2-[(2,6-dichlorobenzoyl)amino]-3-[2-(2,6-dichlorophenyl)-6-quinolinyl]propanoate 41 can be synthesized according to the same method.

MS ($MH^+$): 533/535/537.

1.3 Synthesis of 3-[2-(2,6-dichlorophenyl)-6-quinolinyl]-2-[({(2S)-1-[(4-methylphenyl)sulfonyl] piperidinyl}carbonyl)amino]propanoic acid 90

1.3.1 Synthesis of methyl 3-[2-(2,6-dichlorophenyl)-6-quinolinyl]-2-{[(2S)-piperidinylcarbonyl] amino}propanoate 45

Tert-butyl (2S)-2-{[(1-{[2-(2,6-dichlorophenyl)-6-quinolinyl]methyl}-2-methoxy-2-oxoethyl)amino]carbonyl}-1-piperidinecarboxylate 42 is deprotected with TFA (see 1.1.6) to give methyl 3-[2-(2,6-dichlorophenyl)-6-quinolinyl]-2-{[(2S)-piperidinylcarbonyl]amino}propanoate 45.

MS ($MH^+$): 486/488/490.

1.3.2 Synthesis of methyl 3-[2-(2,6-dichlorophenyl)-6-quinolinyl]-2-[({(2S)-1-[(4-methylphenyl)sulfonyl]piperidinyl}carbonyl)amino]propanoate 46

To methyl 3-[2-(2,6-dichlorophenyl)-6-quinolinyl]-2-{[(2S)-piperidinylcarbonyl]amino}propanoate 45 (0.2 TFA salt) (0.965 g) in $CH_2Cl_2$ (5 ml) are added, at 0 C, DIPEA (0.97 ml) and p-toluenesulfonyl chloride (0.282 g) dissolved in $CH_2Cl_2$. The reaction is stirred at RT for one night, then the mixture is diluted with $CH_2Cl_2$. The organic phase is washed 3 times with a brine solution, dried over $MgSO_4$ and concentrated under vacuum. The residue is purified over silica gel using $CH_2Cl_2/CH_3OH$ (99.5/0.5) as eluent to give methyl 3-[2-(2,6-dichlorophenyl)-6-quinolinyl]-2-[({(2S)-1-[(4-methylphenyl)sulfonyl]piperidinyl}carbonyl)amino]propanoate 46.

Yield: 72%.

MS (MH+): 640/642/644.

1.3.3 Synthesis of 3-[2-(2,6-dichlorophenyl)-6-quinolinyl]-2-[({(2S)-1-[(4-methylphenyl)sulfonyl]piperidinyl}carbonyl)amino]propanoic acid 90

To 455 mg of methyl 3-[2-(2,6-dichlorophenyl)-6-quinolinyl]-2-[({(2S)-1-[(4-methylphenyl)sulfonyl]piperidinyl}carbonyl)amino]propanoate 46 in $CH_3OH$ (5 ml) are added 0.8 ml of 1 N NaOH and 1 ml of water. The solution is stirred at RT overnight, and 1 N HCl (0.8 ml) is added to obtain a weakly acidic pH. Methanol is then evaporated, and the solid obtained is filtered, washed with water and dried to give 3-[2-(2,6-dichlorophenyl)-6-quinolinyl]-2-[({(2S)-1-[(4-methylphenyl)sulfonyl]piperidinyl}carbonyl)amino]propanoic acid 90.

Yield: 82%.

MS (MH+): 626/628/630.

1.4 Synthesis of 2-{[(2,6-dichlorophenyl)(ethoxy)methylene]amino}-3-[2-(2,6-dichlorophenyl)-6-quinolinyl]propanoic acid 64

Compound 64 is synthesized according to Chem. Pharm. Bull. (1984), 32, (11), 4466-4477 starting from compound 35 followed by basic hydrolysis, as described for the transformation of compound 46 into compound 90.

MS (MH+): 561/563.

1.5 Synthesis of 2-[(2,6-dichlorobenzyl)(methyl)amino]-3-[2-(2,6-dichlorophenyl)-6-quinolinyl]propanoic acid 66

Scheme 3:

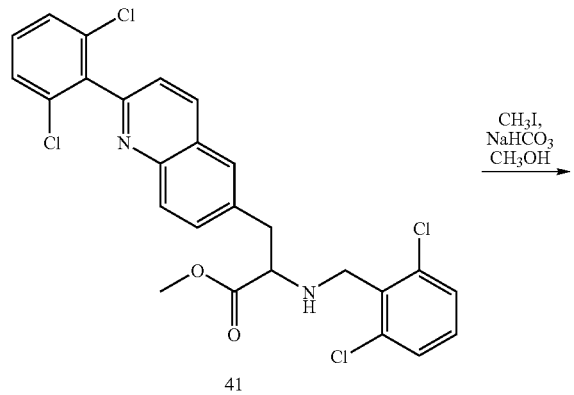

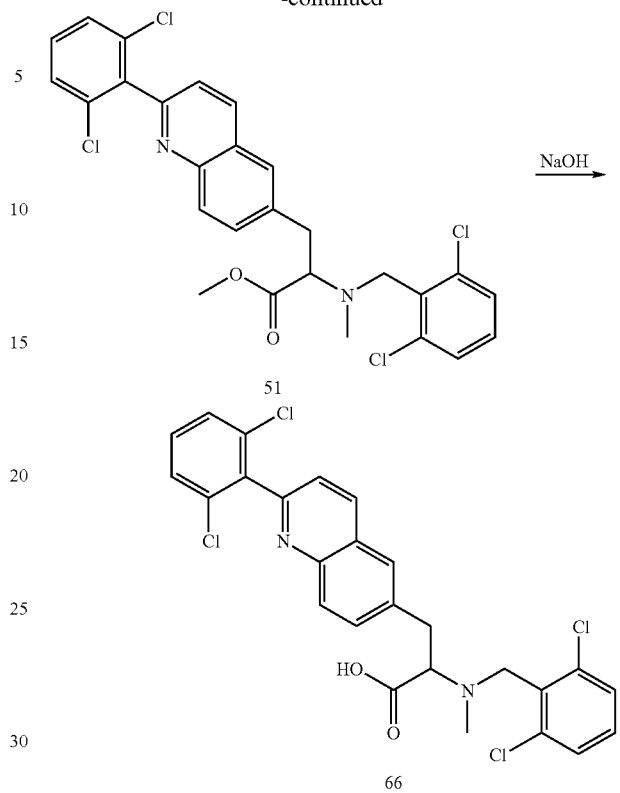

1.5.1 Synthesis of methyl 2-[(2,6-dichlorobenzyl)(methyl)amino]-3-[2-(2,6-dichlorophenyl)-6-quinolinyl]propanoate 51

To 100 mg of (methyl 2-[(2,6-dichlorobenzyl)amino]-3-[2-(2,6-dichlorophenyl)-6-quinolinyl]propanoate) 41 in $CH_3OH$ (2.3 ml) are added, at 0° C., $NaHCO_3$ (1 equ.) and $CH_3I$ (1 equ.). The reaction is stirred for 1 h at 0° C., and then at room temperature for 2 days. The solvent is evaporated and $CH_2Cl_2$ (10 ml) is added to the residue. The solution is washed with water, brine, again water and dried over $MgSO_4$, filtered and evaporated. Due to an incomplete reaction, the protocol is repeated using a tenfold excess of $NaHCO_3$ and $CH_3I$ in MeOH (5 ml). After a similar work-up, the residue is purified by silica gel chromatography using hexane/AcOEt 90/10 as eluent to give methyl 2-[(2,6-dichlorobenzyl)(methyl)amino]-3-[2-(2,6-dichlorophenyl)-6-quinolinyl]propanoate 51.

Yield: 43%.

MS (MH+): 547/549/551.

1.5.2 Synthesis of 2-[(2,6-dichlorobenzyl)(methyl)amino]-3-[2-(2,6-dichlorophenyl)-6-quinolinyl]propanoic acid 66

Hydrolysis of methyl 2-[(2,6-dichlorobenzyl)(methyl)amino]-3-[2-(2,6-dichlorophenyl)-6-quinolinyl]propanoate 51 is performed as described in 1.3.3 and gives 2-[(2,6-dichlorobenzyl)(methyl)amino]-3-[2-(2,6-dichlorophenyl)-6-quinolinyl]propanoic acid 66.

Yield: 65%.

MS (MH+): 533/535/537.

1.6 Synthesis of 3-[2-(2,6-dichlorophenyl)-6-quinolinyl]-2-[(2-hydroxybenzoyl)amino]propanoic acid 71

Hydrolysis of methyl 2-{[2-(acetyloxy)benzoyl]amino}-3-[2-(2,6-dichlorophenyl)-6-quinolinyl]propanoate 70 as described in 1.3.3 gives 3-[2-(2,6-dichlorophenyl)-6-quinolinyl]-2-[(2-hydroxybenzoyl)amino]propanoic acid 71.
Yield: 67%.
MS (MH$^+$): 481/483/485.

1.7 Synthesis of 2-({[(2,6-dichlorophenyl)amino]carbonyl}amino)-3-[2-(2,6-dichlorophenyl)-6-quinolinyl]propanoic acid 87

1.7.1 Synthesis of methyl 2-{[(2,6-dichloroanilino)carbonyl]amino}-3-[2-(2,6-dichlorophenyl)-6-quinolinyl]propanoate 52

To 0.62 g of methyl 2-amino-3-[2-(2,6-dichlorophenyl)-6-quinolinyl]propanoate 33 in CH$_2$Cl$_2$ (10 ml) are added 0.343 g of 2,6-dichlorophenyl isocyanate. The solution is stirred at RT and reduced to the half by evaporation. The solid residue is filtered and washed with CH$_2$Cl$_2$ and hexane to give a white powder that is recrystallised in hot CH$_3$CN. The compound is purified over silica gel using CH$_2$Cl$_2$/CH$_3$OH 99.5/0.5 as eluent. The obtained white powder is once more washed with CH$_3$CN to give methyl 2-{[(2,6-dichloroanilino)carbonyl]amino}-3-[2-(2,6-dichlorophenyl)-6-quinolinyl]propanoate 52.
Yield: 36%.
MS (MH$^+$): 562/564/566.

1.7.2 Synthesis of 2-({[(2,6-dichlorophenyl)amino]carbonyl}amino)-3-[2-(2,6-dichlorophenyl)-6-quinolinyl]propanoic acid 87

Hydrolysis of methyl 2-{[(2,6-dichloroanilino)carbonyl]amino}-3-[2-(2,6-dichlorophenyl)-6-quinolinyl]propanoate 52 as described in 1.3.3 gives 2-({[(2,6-dichlorophenyl)amino]carbonyl}amino)-3-[2-(2,6-dichlorophenyl)-6-quinolinyl]propanoic acid 87.
Yield: 58%.
MS (MH$^+$): 548/550/552.

1.8 Synthesis of 2-[(2,6-dichlorobenzoyl)amino]-3-(2-phenoxy-6-quinolinyl)propanoic acid 81

Scheme 4:

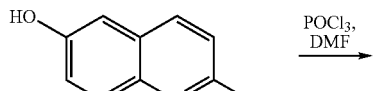
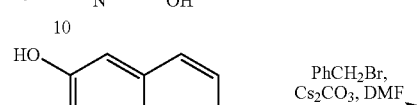
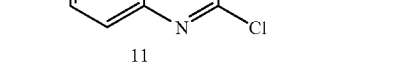

-continued

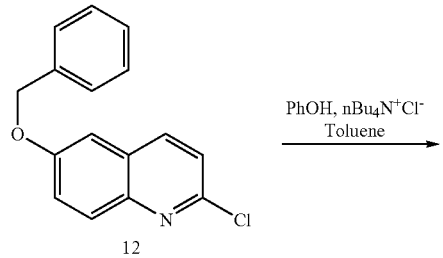
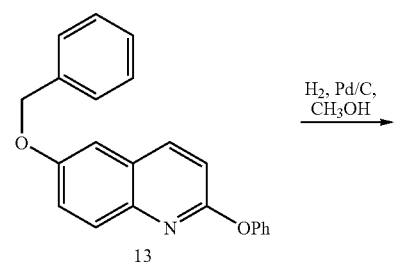
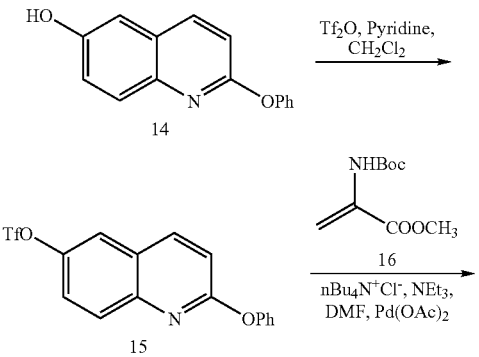
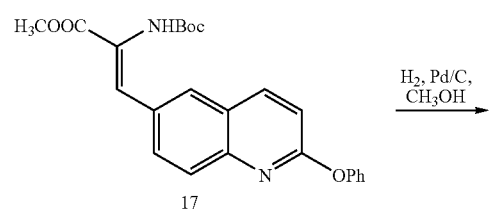
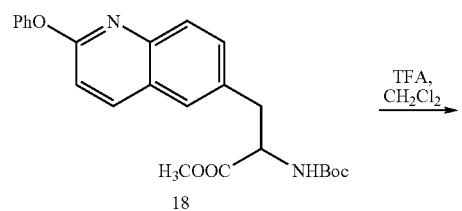
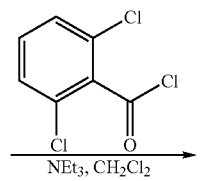

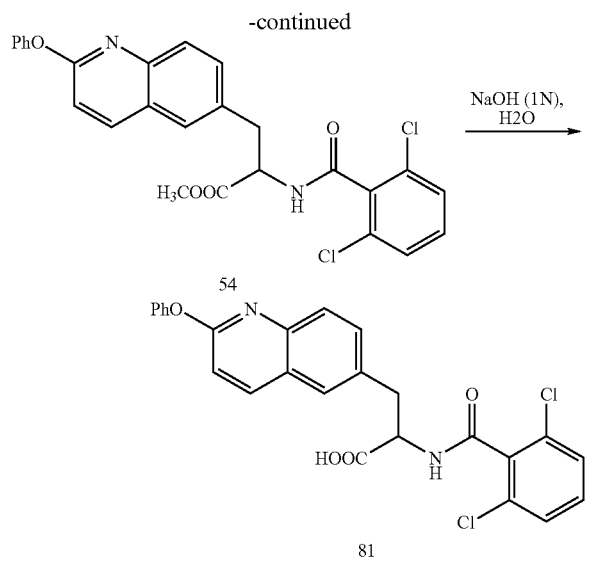

1.8.1 Synthesis of 2-chloro-6-quinolinol 11

A solution of 2,6-quinolinediol 10 (5 g) in $POCl_3$ (21 ml) and DMF (3.4 ml) is stirred for 12 h at room temperature, then heated for 1 h at 115° C. The reaction is poured into water (100 ml) at 0° C. and neutralized with a 32% aqueous $NH_3$ solution. The solid obtained by filtration is washed with acetone, and the resulting organic phase is evaporated to give 2-chloro-6-quinolinol 11 as a solid. No further purification is needed.

Yield: 98%.
MS ($MH^+$): 180.

1.8.2 Synthesis of 6-(benzyloxy)-2-chloroquinoline 12

To a solution of 2-chloro-6-quinolinol 11 (5.45 g) in DMF (100 ml) is added, at 0° C., cesium carbonate (11.9 g). After 15 minutes at 0° C., benzyl bromide (4 ml) is added and the reaction is stirred for 12 h at room temperature. Water (100 ml) is then added and the solid obtained is filtered and washed with pentane. No further purification is needed. 6-(benzyloxy)-2-chloroquinoline 12 is obtained as a powder.

Yield: 94%.
MS ($MH^+$): 170.

1.8.3 Synthesis of 6-(benzyloxy)-2-phenoxyquinoline 13

To a 50% (w/w) NaOH solution (10.2 ml) is added phenol (0.697 g). After 50 minutes at room temperature, toluene (10.21 ml) and 6-(benzyloxy)-2-chloroquinoline 12 (2 g) and tetrabutyl ammonium (2.062 g) are added. The solution is stirred under argon at reflux for 24 h. Water (5 ml) is added and the solution is extracted with toluene (3×10 ml). The organic phases are dried over $MgSO_4$ and evaporated under vacuum. The residue is purified by silica gel chromatography using AcOEt/cyclohexane 20/80 as eluent. The obtained solid is dissolved in AcOEt and pentane is added; 6-(benzyloxy)-2-phenoxyquinoline 13 precipitates as a white powder.

Yield: 70%.
MS ($MH^+$): 328.

Compounds described in table 1 can be synthesized according to the same method.

TABLE 1

| n° | IUPAC Name | MS ($MH^+$) |
| --- | --- | --- |
| 13a | 6-(benzyloxy)-2-(4-chlorophenoxy)quinoline | 362 |
| 13b | 6-(benzyloxy)-2-methoxyquinoline | 266 |
| 13c | 6-(benzyloxy)-2-(2-methoxyphenoxy)quinoline | 358 |
| 13d | 6-(benzyloxy)-2-(2,6-dimethoxyphenoxy)quinoline | 388 |
| 13e | 6-(benzyloxy)-2-(2,6-dichlorophenoxy)quinoline | 396/398 |

1.8.4 Synthesis of 2-phenoxy-6-quinolinol 14

To a solution of 6-(benzyloxy)-2-phenoxyquinoline 13 (0.862 g) in $CH_3OH$ (10 ml) is added 10% of palladium on C (10%). The reaction is stirred under $H_2$ at room temperature for 1 night. After filtration on celite and concentration, the residue is purified by silica gel chromatography using AcOEt/petroleum ether 10/90 as eluent to give compound 2-phenoxy-6-quinolinol 14 as an oil.

Yield: 61%.
MS ($MH^+$): 238.

Compounds described in table 2 can be synthesized according to the same method.

TABLE 2

| n° | IUPAC Name | MS ($MH^+$) |
| --- | --- | --- |
| 14a | 2-(4-chlorophenoxy)-6-quinolinol | 272 |
| 14b | 2-methoxy-6-quinolinol | 176 |
| 14c | 2-(2-methoxyphenoxy)-6-quinolinol | 268 |
| 14d | 2-(2,6-dimethoxyphenoxy)-6-quinolinol | 298 |
| 14e | 2-(2,6-dichlorophenoxy)-6-quinolinol | 306/308 |

1.8.5 Synthesis of 2-phenoxy-6-quinolinyl trifluoromethanesulfonate 15

To a solution of 2-phenoxy-6-quinolinol 14 (0.562 g) in $CH_2Cl_2$ (20 ml) is added pyridine (0.6 ml) under Argon. After 15 minutes at 0° C., trifluoromethanesulfonic anhydride (0.64 ml) is added. The reaction temperature is allowed to reach slowly room temperature. The reaction is stirred for 5 h and washed with a saturated solution of $NaHCO_3$. The solution is extracted with $CH_2Cl_2$ (3×10 ml). The organic phase is dried over $MgSO_4$ and evaporated under vacuum. The residue is purified by silica gel chromatography using AcOEt/petroleum ether 10/90 as eluent.

Yield: 87%.
MS ($MH^+$): 370.

Compounds described in table 3 can be synthesized according to the same method.

TABLE 3

| n° | IUPAC Name | MS ($MH^+$) |
| --- | --- | --- |
| 15a | 2-(4-chlorophenoxy)-6-quinolinyl trifluoromethanesulfonate | 404 |
| 15b | 2-methoxy-6-quinolinyl trifluoromethanesulfonate | 308 |
| 15c | 2-(2-methoxyphenoxy)-6-quinolinyl trifluoromethanesulfonate | 400 |
| 15d | 2-(2,6-dimethoxyphenoxy)-6-quinolinyl trifluoromethanesulfonate | 430 |
| 15e | 2-(2,6-dichlorophenoxy)-6-quinolinyl trifluoromethanesulfonate | 438/440 |

1.8.6 Synthesis of methyl-2-N-(tert-butoxycarbonyl)-acrylate 16

To a solution of methyl 2-[(tert-butoxycarbonyl)amino]-3-hydroxypropanoate (7.19 g) in CH$_2$Cl$_2$ (15 ml) are added 3.04 ml of mesyl chloride. NEt$_3$ (13.64 ml) is then added at −50° C., under Argon. After 45 minutes at −50° C., the reaction warmed up to room temperature and stirred for 4 hours. The solution is poured into ice and the aqueous phase is extracted with CH$_2$Cl$_2$ (3×10 ml). The organic phases are dried over MgSO$_4$ and evaporated to dryness. The residue is purified by silica gel chromatography using AcOEt/cyclohexane 20/80 as eluent to give 16 as oil.

Yield: 93%.
MS (MH$^+$): 202.

1.8.7 Synthesis of methyl 2-[(tert-butoxycarbonyl)amino]-3-(2-phenoxy-6-quinolinyl)-2-propenoate 17

To a solution of 2-phenoxy-6-quinolinyl trifluoromethanesulfonate 15 (0.782 g) in DMF (20 ml) is added palladium acetate (0.0285 g). The solution is degassed with Argon for 30 minutes. Methyl-2-N-(tert-butoxycarbonyl)-acrylate 16 (1.065 g), tetrabutyl ammonium chloride (0.706 g) and NEt$_3$ (0.342 ml) are then added. The solution is heated at 90° C. for 2 h and then poured in ice. The aqueous phase is extracted with AcOEt (3×15 ml). The organic phases are dried over MgSO$_4$ and evaporated to dryness. The residue is purified by silica gel chromatography using AcOEt/ether petroleum 10/90 then 40/60 as eluent.

Yield: 91%.
MS (MH$^+$): 421.

Compounds described in table 4 can be synthesized according to the same method.

TABLE 4

| n° | IUPAC Name | MS (MH$^+$) |
|---|---|---|
| 17a | methyl 2-[(tert-butoxycarbonyl)amino]-3-[2-(4-chlorophenoxy)-6-quinolinyl]-2-propenoate | 455 |
| 17b | methyl 2-[(tert-butoxycarbonyl)amino]-3-(2-methoxy-6-quinolinyl)-2-propenoate | 359 |
| 17c | methyl 2-[(tert-butoxycarbonyl)amino]-3-[2-(2-methoxyphenoxy)-6-quinolinyl]-2-propenoate | 451 |
| 17d | methyl 2-[(tert-butoxycarbonyl)amino]-3-[2-(2,6-dimethoxyphenoxy)-6-quinolinyl]-2-propenoate | 481 |
| 17e | methyl 2-[(tert-butoxycarbonyl)amino]-3-[2-(2,6-dichlorophenoxy)-6-quinolinyl]-2-propenoate | 490 |

1.8.8 Synthesis of methyl 2-[(tert-butoxycarbonyl)amino]-3-(2-phenoxy-6-quinolinyl) propanoate 18

To a solution of methyl 2-[(tert-butoxycarbonyl)amino]-3-(2-phenoxy-6-quinolinyl)-2-propenoate 17 (1.053 g) in methanol (15 ml) is added 10% of Pd over C (10%). The reaction is stirred at room temperature under H$_2$ atmosphere overnight. After filtration over celite and concentration, the residue is purified by silica gel chromatography using AcOEt/ether petroleum 40/60 as eluent to give compound methyl 2-[(tert-butoxycarbonyl)amino]-3-(2-phenoxy-6-quinolinyl) propanoate 18 as an oil.

Yield: 82%.
MS (MH$^+$): 423.

Compounds described in table 5 can be synthesized according to the same method.

TABLE 5

| n° | IUPAC Name | MS (MH$^+$) |
|---|---|---|
| 18a | methyl 2-[(tert-butoxycarbonyl)amino]-3-[2-(4-chlorophenoxy)-6-quinolinyl]propanoate | 457 |
| 18b | methyl 2-[(tert-butoxycarbonyl)amino]-3-(2-methoxy-6-quinolinyl)propanoate | 361 |
| 18c | methyl 2-[(tert-butoxycarbonyl)amino]-3-[2-(2-methoxyphenoxy)-6-quinolinyl]propanoate | 453 |
| 18d | methyl 2-[(tert-butoxycarbonyl)amino]-3-[2-(2,6-dimethoxyphenoxy)-6-quinolinyl]propanoate | 483 |
| 18e | methyl 2-[(tert-butoxycarbonyl)amino]-3-[2-(2,6-dichlorophenoxy)-6-quinolinyl]propanoate | 491/493 |

1.8.9 Synthesis of methyl 2-amino-3-(2-phenoxy-6-quinolinyl)propanoate 53

A solution of 0.737 g of methyl 2-[(tert-butoxycarbonyl)amino]-3-(2-phenoxy-6-quinolinyl) propanoate 18, trifluoroacetic acid (1 ml) and a drop of anisole in CH$_2$Cl$_2$ (6 ml) is stirred at 0° C. under argon. The reaction temperature is allowed to reach slowly room temperature, and the solution is stirred at this temperature for 2 h. After concentration, the residue is diluted in AcOEt (6 ml) and the mixture is neutralized with NaHCO$_3$ (5%). The aqueous phase is extracted with AcOEt (4×5 ml). The organic phases are dried over MgSO$_4$, filtered and concentrated. The obtained residue is purified over silica gel using (CH$_2$Cl$_2$/CH$_3$OH 90/10+5% NEt$_3$) as eluent to give methyl 2-amino-3-(2-phenoxy-6-quinolinyl)propanoate 53 as an oil.

Yield: 85%.
MS (MH$^+$): 322.

1.8.10 Synthesis of methyl 2-[(2,6-dichlorobenzoyl)amino]-3-(2-phenoxy-6-quinolinyl) propanoate 54

To a solution of methyl 2-amino-3-(2-phenoxy-6-quinolinyl)propanoate 53 (0.363 g) in CH$_2$Cl$_2$ (5 ml) under argon is added NEt$_3$ (0.937 ml). After 15 minutes, 2,6-dichlorophenylcarbonylchloride (0.241 ml) is added. The solution is stirred for 6 h at room temperature. After addition of NaHCO$_3$ (5 ml), the aqueous phase is extracted with CH$_2$Cl$_2$ (3×10 ml). The organic phases are dried over MgSO$_4$, filtered and concentrated. The obtained residue is purified over silica gel using AcOEt/petroleum ether 10/90 then 60/40 as eluent to give methyl 2-[(2,6-dichlorobenzoyl)amino]-3-(2-phenoxy-6-quinolinyl) propanoate 54.

Yield: 91%.
MS (MH$^+$): 495.

1.8.11 Synthesis of 2-[(2,6-dichlorobenzoyl)amino]-3-(2-phenoxy-6-quinolinyl)propanoic acid 81

Methyl 2-[(2,6-dichlorobenzoyl)amino]-3-(2-phenoxy-6-quinolinyl) propanoate 54 is added to a mixture of CH$_3$CN (10.99 ml), NaOH 1N (0.914 ml) and water (0.545 ml). The reaction is stirred at room temperature for 3 h. After addition of KHSO$_4$ (10%, 22.4 ml), CH$_3$CN is evaporated under vacuum. The aqueous phase is extracted with AcOEt (2×5 ml). The organic phases are washed with brine, dried over MgSO$_4$ and evaporated under vacuum. The resulting residue is washed with 5 ml of pentane to give 2-[(2,6-dichlorobenzoyl)amino]-3-(2-phenoxy-6-quinolinyl)propanoic acid 81 as a white powder.

Yield: 82%.
MS (MH$^+$): 481/483/485.

1.9 Synthesis of 2-[(2,6-dichlorobenzyl)oxy]-3-[2-(2,6-dichlorophenyl)-6-quinolinyl]propanoic acid 91 and 2-[(2,6-dichlorobenzoyl)oxy]-3-[2-(2,6-dichlorophenyl)-6-quinolinyl]propanoic acid 93

Scheme 5:
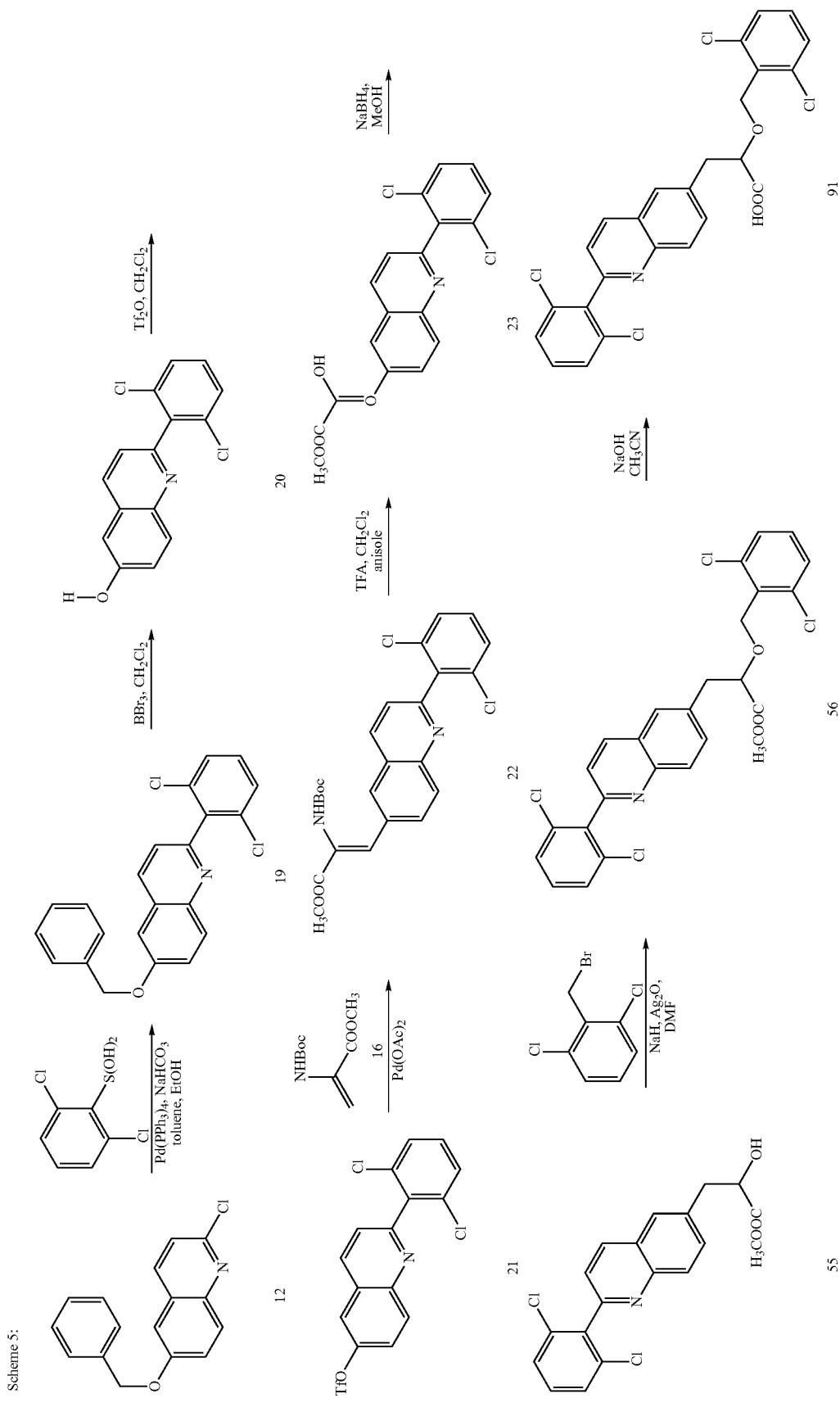

-continued
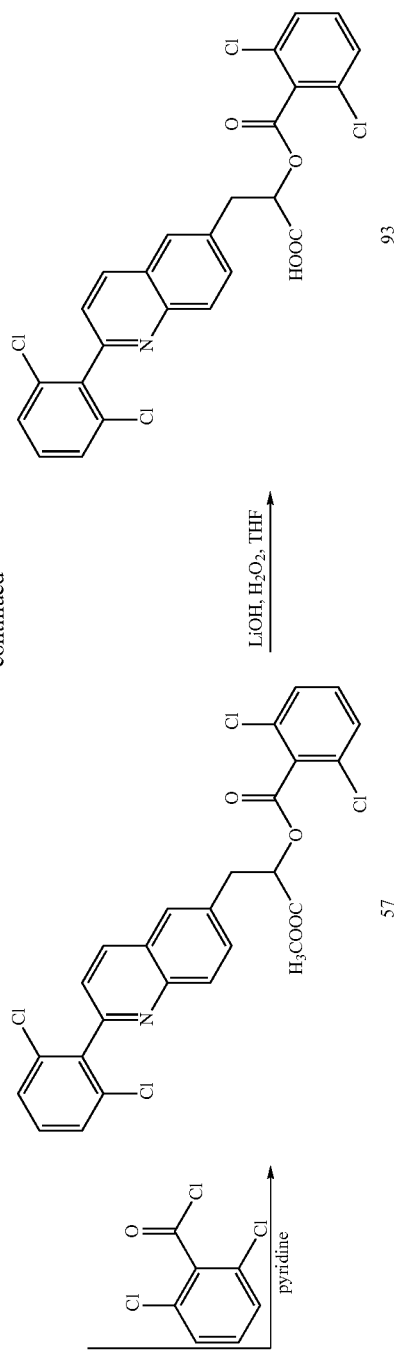

1.9.1 Synthesis of 6-(benzyloxy)-2-(2,6-dichlorophenyl)quinoline 19

To a solution of 3 g of 6-(benzyloxy)-2-chloroquinoline 12 in toluene (294 ml) is added Pd(PPh$_3$)$_4$ (1 g). After 30 minutes, a solution of 2,6-dichlorophenylboronic acid (4.22 g) in methanol (186 ml) and 120 ml of a saturated aqueous solution of NaHCO$_3$ is added. The reaction is heated under reflux for 4 h. After evaporation, the aqueous phase is extracted with AcOEt (3×20 ml). The organic phases are washed with brine, dried over MgSO$_4$ and evaporated to dryness. The residue is purified over silica gel using AcOEt/petroleum ether 5/95 then 10/90 as eluent to give 6-(benzyloxy)-2-(2,6-dichlorophenyl)quinoline 19 as an oil.
Yield: 62%.
MS (MH$^+$): 380.

1.9.2 Synthesis of 2-(2,6-dichlorophenyl)-6-quinolinol 20

To a solution of 6-(benzyloxy)-2-(2,6-dichlorophenyl)quinoline 19 (2.5 g) in CH$_2$Cl$_2$ (20 ml) are added, at 0° C., 20 ml of BBr$_3$ (1 M in CH$_2$Cl$_2$). The solution is stirred for 1 h at room temperature. Water (20 ml) is added and the resulting solution is alkalinized with 1 N NaOH. The aqueous phase is extracted with AcOEt (3×20 ml). The organic phases are washed with brine, dried over MgSO$_4$ and evaporated. 2-(2,6-dichlorophenyl)-6-quinolinol 20 is obtained as a yellow solid and is used without further purification in the next step.
Yield: 100%.
MS (MH$^+$): 290.

1.9.3 Synthesis of 2-(2,6-dichlorophenyl)-6-quinolinyl trifluoromethanesulfonate 21

To a solution of 2-(2,6-dichlorophenyl)-6-quinolinol 20 (1.9 g) in CH$_2$Cl$_2$ (20 ml) is added pyridine (1.6 ml) at room temperature. After 5 minutes, trifluoroacetic acid (1.7 ml) is added at 0° C. The solution is stirred for 2 h at 0° C. and a saturated solution of NaHCO$_3$ (20 ml) is added. The aqueous phase is extracted with AcOEt (3×20 ml). The organic phases are washed with brine, dried over Na$_2$SO$_4$ and evaporated to dryness. The resulting solid 21 is used in the next step without further purification.
Yield: 100%.
MS (MH$^+$): 422.

1.9.4 Synthesis of methyl 2-[(tert-butoxycarbonyl)amino]-3-[2-(2,6-dichlorophenyl)-6-quinolinyl]-2-propenoate 22

To a solution of 2-(2,6-dichlorophenyl)-6-quinolinyl trifluoromethanesulfonate 21 (0.67 g) in DMF (15 ml) are added 0.8 g of freshly prepared methyl-2-N-(tert-butoxycarbonyl)-acrylate 16, tetrabutylammonium (0.57 g) and NEt$_3$ (0.3 ml). The solution is degassed for 20 minutes and Pd(OAc)$_2$ (36 mg, 10% mol) is added. The solution is heated at 90° C. for 3 h, then water (10 ml) is added. The aqueous phase is extracted with AcOEt (3×10 ml), and the organic phases are washed with water (2×10 ml), brine and dried over MgSO$_4$. After evaporation under vacuum, the residue is purified over silica gel using AcOEt/petroleum ether 20/80 as eluent.
Yield: 77%.
MS (MH$^+$): 473.

1.9.5 Synthesis of methyl 3-[2-(2,6-dichlorophenyl)-6-quinolinyl]-2-hydroxy-2-propenoate 23

To a solution of 2-[(tert-butoxycarbonyl)amino]-3-[2-(2,6-dichlorophenyl)-6-quinolinyl]-2-propenoate 22 (0.48 g) in CH$_2$Cl$_2$ (2 ml) are added at 0° C. two drops of anisole and 1.6 ml of trifluoroacetic acid. The solution is stirred for 2 h and a solution of NaHCO$_3$ saturated is added to reach a basic pH. The aqueous phase is extracted with AcOEt (3×10 ml). The organic phases are washed with brine, dried over MgSO$_4$ and concentrated. The residue is washed with methanol to give methyl 3-[2-(2,6-dichlorophenyl)-6-quinolinyl]-2-hydroxy-2-propenoate 23.
Yield: 53%.
MS (MH$^+$): 374.

1.9.6 Synthesis of methyl 3-[2-(2,6-dichlorophenyl)-6-quinolinyl]-2-hydroxypropanoate 55

To a solution of methyl 3-[2-(2,6-dichlorophenyl)-6-quinolinyl]-2-hydroxy-2-propenoate 23 (0.38 g) in CH$_3$OH (2 ml) is added, at 0° C., NaBH$_4$ (36 mg). The solution is stirred for 5 h. A saturated solution of NaHCO$_3$ and then, a solution of 1 N NaOH are added until pH=11. The aqueous phase is extracted with AcOEt (3×10 ml). The organic phases are washed with brine, dried over MgSO$_4$ and concentrated. The residue is purified over silica gel using AcOEt/petroleum ether 30/70 then 35/65 as eluent to give methyl 3-[2-(2,6-dichlorophenyl)-6-quinolinyl]-2-hydroxypropanoate 55.
Yield: 65%.
MS (MH$^+$): 377.

1.9.7 Synthesis of methyl 2-[(2,6-dichlorobenzyl)oxy]-3-[2-(2,6-dichlorophenyl)-6-quinolinyl]propanoate 56

To a solution of methyl 3-[2-(2,6-dichlorophenyl)-6-quinolinyl]-2-hydroxypropanoate 55 (0.159 g) and α-bromo-2,6-dichlorotoluene (1.05 g) in DMF (3.5 ml) is added 17 mg of NaH (60% dispersion in mineral oil) and Ag$_2$O (0.102 g). The solution is stirred for 1 night at room temperature. A saturated solution of NaHCO$_3$ is added. The aqueous phase is extracted with AcOEt (3×10 ml). The organic phases are washed with water (2×10 ml), with brine and dried over MgSO$_4$. After concentration, the residue is purified twice over silica gel using AcOEt/petroleum ether 10/90 then 15/85 as eluent to give methyl 2-[(2,6-dichlorobenzyl)oxy]-3-[2-(2,6-dichlorophenyl)-6-quinolinyl]propanoate 56.
Yield: 70%.
MS (MH$^+$): 534.

1.9.8 Synthesis of 2-[(2,6-dichlorobenzyl)oxy]-3-[2-(2,6-dichlorophenyl)-6-quinolinyl]propanoic acid 91

A solution of methyl 2-[(2,6-dichlorobenzyl)oxy]-3-[2-(2,6-dichlorophenyl)-6-quinolinyl]propanoate 56 (0.123 g) and 1 N NaOH (0.236 ml) in a mixture of acetonitrile/water (3 ml/0.14 ml) is stirred for 3 h at room temperature. After addition of a 10% KHSO$_4$ solution (3 ml), the mixture is concentrated. The aqueous phase is extracted with AcOEt (3×10 ml). The organic phases are washed with brine, dried over MgSO$_4$ and evaporated under vacuum. The residue is washed with CH$_2$Cl$_2$ and 2-[(2,6-dichlorobenzyl)oxy]-3-[2-(2,6-dichlorophenyl)-6-quinolinyl]propanoic acid 91 is obtained as a white powder.
Yield: 69%.
MS (MH$^+$): 521.

1.9.9 Synthesis of 1-([2-(2,6-dichlorophenyl)-6-quinolinyl]methyl)-2-methoxy-2-oxoethyl 2,6-dichlorobenzoate 57

To a solution of methyl 3-[2-(2,6-dichlorophenyl)-6-quinolinyl]-2-hydroxypropanoate 55 (0.104 g) in pyridine (1 ml) is added 2,6-dichlorobenzoyl chloride (0.2 ml). The solution is stirred for 6 h at room temperature. A saturated solution of NaHCO$_3$ (10 ml) is added. The aqueous phase is extracted with AcOEt (3×10 ml). The organic phases are washed with brine, dried over MgSO$_4$ and evaporated. The residue is purified twice over silica gel using AcOEt/petroleum ether (10/90 to 20/80) as eluent.

Yield: 88%.
MS (MH$^+$): 550.

1.9.10 Synthesis of 2-[(2,6-dichlorobenzoyl)oxy]-3-[2-(2,6-dichlorophenyl)-6-quinolinyl]propanoic acid 93

To a solution of 1-{[2-(2,6-dichlorophenyl)-6-quinolinyl]methyl}-2-methoxy-2-oxoethyl 2,6-dichlorobenzoate 57 (0.113 g) in 10 ml THF are added, at 0° C., 1 ml of LiOH (1 M) and 0.5 ml of H$_2$O$_2$ (30%). The solution is then stirred at room temperature for 18 h. After addition of 10 ml KHSO$_4$ (10%), the THF is evaporated. The aqueous phase is extracted with AcOEt (3×10 ml). The organic phases are washed with brine, dried over MgSO$_4$ and evaporated under vacuum. The residue is triturated in pentane to give 2-[(2,6-dichlorobenzoyl)oxy]-3-[2-(2,6-dichlorophenyl)-6-quinolinyl]propanoic acid 93 as a white powder.

Yield: 93%.
MS (MH$^+$): 534.

1.10 Synthesis of 2,6-dichloro-N-[2-[2-(2,6-dichlorophenyl)-6-quinolinyl]-1-(1H-tetraazol-5-yl)ethyl]benzamide 126

Scheme 6.

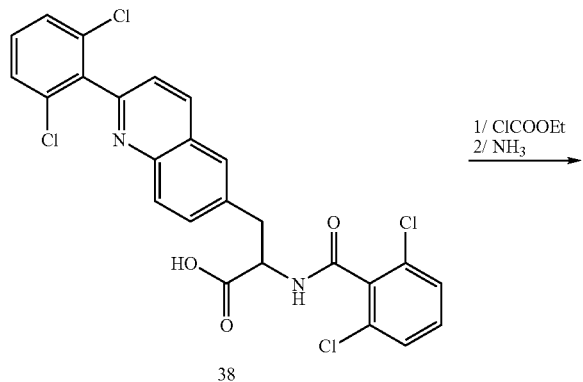

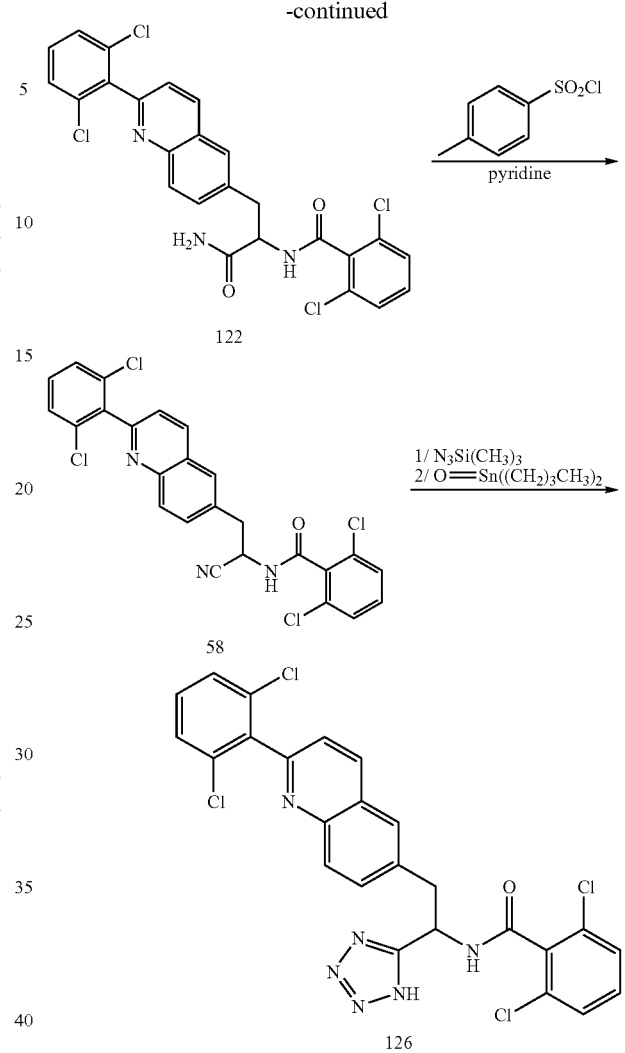

1.10.1 Synthesis of N-(2-amino-1-{[2-(2,6-dichlorophenyl)-6-quinolinyl]methyl}-2-oxoethyl)-2,6-dichlorobenzamide 122.

2-[(2,6-dichlorobenzoyl)amino]-3-[2-(2,6-dichlorophenyl)-6-quinolinyl]propanoic acid 38 (2.12 g) in dry THF (15 ml) is cooled to −20° C. NEt$_3$ (0.54 ml) and ethyl chloroformate (0.37 ml) are added. The solution is stirred at this temperature for 20 minutes. The resulting solution is saturated with gaseous NH$_3$ at −30° C. The mixture is allowed to reach room temperature. After one night, the residue is filtered and washed with THF, then dried under vacuum at 60° C. and purified over silica gel using CH$_2$Cl$_2$/CH$_3$OH (95/5) as eluent to give N-(2-amino-1-{[2-(2,6-dichlorophenyl)-6-quinolinyl]methyl}-2-oxoethyl)-2,6-dichlorobenzamide 122.

Yield: 55%.
MS (MH$^+$): 532/534/536.

1.10.2 Synthesis of 2,6-dichloro-N-{1-cyano-2-[2-(2,6-dichlorophenyl)-6-quinolinyl]ethyl}benzamide 58

To a solution of N-(2-amino-1-{[2-(2,6-dichlorophenyl)-6-quinolinyl]methyl}-2-oxoethyl)-2,6-dichlorobenzamide 122 (1.09 g) in pyridine (9 ml) is added p-toluenesulfonyl chloride (583 mg) at RT. The solution is stirred at 80° C. After one night, 120 mg of p-toluenesulfonyl chloride are added again to the mixture at RT to drive the reaction to completion. The solution is heated at 80° C. for one additional day. The organic phases are evaporated, AcOEt and a small amount of CH$_2$Cl$_2$ are added. The organic phases are washed 3 times with water, one time with a solution of NaHCO$_3$, dried over MgSO$_4$ and evaporated to dryness. The residue so obtained was purified over silica gel using CH$_2$Cl$_2$/CH$_3$OH (99.25/0.75) as eluent to give 2,6-dichloro-N-{1-cyano-2-[2-(2,6-dichlorophenyl)-6-quinolinyl]ethyl}benzamide 58.

Yield: 65%.
MS (MH$^+$): 514/516/518.

1.10.3 Synthesis of 2,6-dichloro-N-[2-[2-(2,6-dichlorophenyl)-6-quinolinyl]-1-(1H-tetraazol-5-yl)ethyl]benzamide 126

To 2,6-dichloro-N-{1-cyano-2-[2-(2,6-dichlorophenyl)-6-quinolinyl]ethyl}benzamide 58 (0.358 g) in toluene (5 ml) are added trimethylsilyl azide (184 μl) and dibutyltin oxide (17 mg). The solution is heated at reflux overnight, then evaporated under vacuum. The resulting residue is purified twice over silica gel using one time CH$_2$Cl$_2$/CH$_3$OH 85/15 as eluent and the second time CH$_2$Cl$_2$/(CH$_3$OH-10% NH$_4$OH) 85/15 to give 2,6-dichloro-N-[2-[2-(2,6-dichlorophenyl)-6-quinolinyl]-1-(1H-tetraazol-5-yl)ethyl]benzamide 126.

Yield: 36%.
MS (MH$^+$): 557/559/561.

1.11 Synthesis of 3-[2-(2,6-dichlorophenyl)-6-quinolinyl]-2-{[3,4-dioxo-2-(propylamino)-1-cyclobuten-1-yl]amino}propanoic acid 198

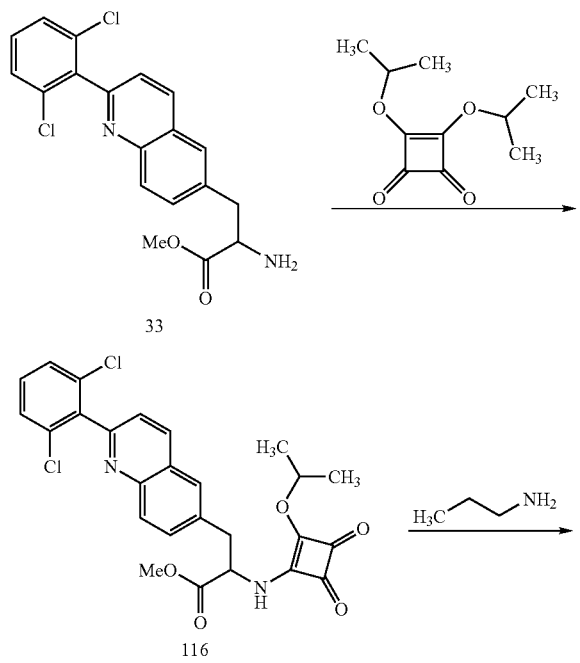

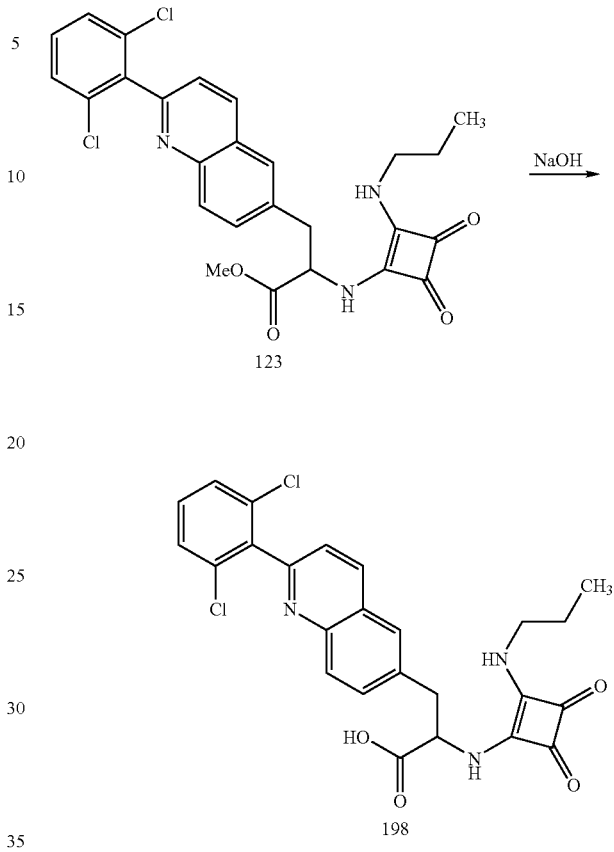

1.11.1 Synthesis of methyl 3-[2-(2,6-dichlorophenyl)-6-quinolinyl]-2-[(2-isopropoxy-3,4-dioxo-1-cyclobuten-1-yl)amino]propanoate 116

To a solution of methyl 2-amino-3-[2-(2,6-dichlorophenyl)-6-quinolinyl]propanoate 33 (2 TFA salt, 1.51 g) in CH$_3$OH (15 ml) cooled with an ice bath, are added 0.96 ml of DIPEA and 495.6 mg of 3,4-diisopropoxy-3-cyclobutene-1,2-dione. The solution is stirred overnight at Rt. The solution is evaporated and the resulting residue is purified over silica gel using CH$_2$Cl$_2$/CH$_3$OH (99.2/0.8) as eluent to give methyl 3-[2-(2,6-dichlorophenyl)-6-quinolinyl]-2-[(2-isopropoxy-3,4-dioxo-1-cyclobuten-1-yl)amino]propanoate 116.

Yield: 57%.
MS (MH$^+$): 513/515/517.

1.11.2 Synthesis of methyl 3-[2-(2,6-dichlorophenyl)-6-quinolinyl]-2-{[3,4-dioxo-2-(propylamino)-1-cyclobuten-1-yl]amino}propanoate 123

To methyl 3-[2-(2,6-dichlorophenyl)-6-quinolinyl]-2-[(2-isopropoxy-3,4-dioxo-1-cyclobuten-1-yl)amino]propanoate 116 (690 mg) in CH$_3$OH (20 ml) are added 132 μl of n-propylamine. After addition of DMF (15 ml), the solution is stirred at RT overnight. The evaporation of CH$_3$OH gives a DMF residue that is diluted in water (200 ml) and stirred overnight. The solid is filtered, washed with water then with MeOH, diluted in DMF, and n-propylamine (150 μl) is added to drive the reaction to completion. The solution is stirred at RT for 48 h, then poured into water. DMF is evaporated and the resulting solid is filtered, washed with water and dried. The product is purified by HPLC/MS (eluent: CH$_3$CN/water/ TFA, 8 minutes gradient from respectively 5/95/0.1 to 95/5/ 0.1). CH$_3$CN is evaporated and water is added to the residue. The resulting solid is filtered and dried to give methyl 3-[2-(2,6-dichlorophenyl)-6-quinolinyl]-2-{[3,4-dioxo-2-(propylamino)-1-cyclobuten-1-yl]amino}propanoate 123.

Yield: 10%.
MS (MH$^+$): 513/515/517.

1.11.3 Synthesis of 3-[2-(2,6-dichlorophenyl)-6-quinolinyl]-2-{[3,4-dioxo-2-(propylamino)-1-cyclobuten-1-yl]amino}propanoic acid 198

The basic hydrolysis of methyl 3-[2-(2,6-dichlorophenyl)-6-quinolinyl]-2-([3,4-dioxo-2-(propylamino)-1-cyclobuten-1-yl]amino)propanoate 123 into 3-[2-(2,6-dichlorophenyl)-6-quinolinyl]-2-{[3,4-dioxo-2-(propylamino)-1-cyclobuten-1-yl]amino}propanoic acid 198 follows the procedure described in 1.3.3.

Yield: 80%.
MS (MH$^+$): 498/500/502.

1.12 Synthesis of 2,6-dichloro-N-(1-{[2-(2,6-dichlorophenyl)-6-quinolinyl]methyl}-2-{[2-(4-morpholinyl)ethyl]amino}-2-oxoethyl)benzamide 117

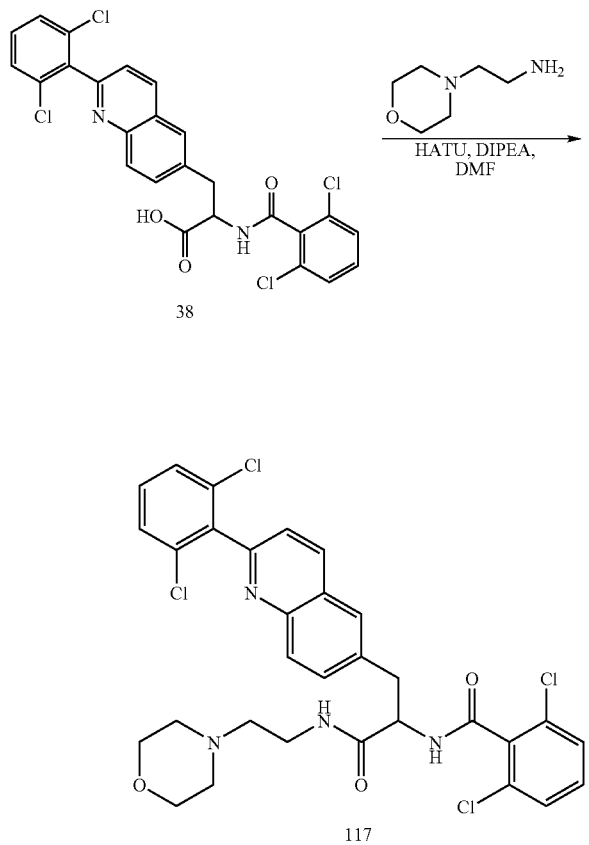

The transformation of 2-[(2,6-dichlorobenzoyl)amino]-3-[2-(2,6-dichlorophenyl)-6-quinolinyl]propanoic acid 38 into 2,6-dichloro-N-(1-{[2-(2,6-dichlorophenyl)-6-quinolinyl]methyl}-2-{[2-(4-morpholinyl)ethyl]amino}-2-oxoethyl)benzamide 117 follows the same conditions that the transformation of compound 33 into compound 35 (scheme 1).

Yield: 48%.
MS (MH$^+$): 645/647/649.

1.13 Synthesis of ({2-[(2,6-dichlorobenzoyl)amino]-3-[2-(2,6-dichlorophenyl)-6-quinolinyl]propanoyl}oxy)methyl pivalate 129

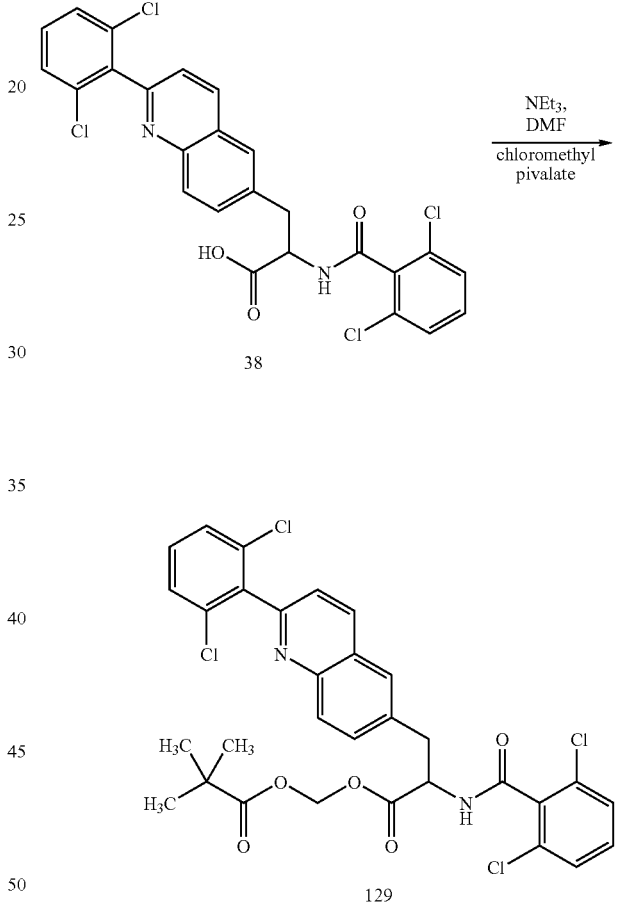

To 2-[(2,6-dichlorobenzoyl)amino]-3-[2-(2,6-dichlorophenyl)-6-quinolinyl]propanoic acid 38 (534 mg) are added 195 µl of triethylamine and, after 15 minutes, 290 µl of chloromethyl pivalate. The solution is stirred at RT overnight and then poured in AcOEt. The organic phases are washed with water and brine, dried over MgSO$_4$ and concentrated. The resulting residue is purified over silica gel using CH$_2$Cl$_2$/C$_2$H$_5$OH 99/1 as eluent to give ({2-[(2,6-dichlorobenzoyl)amino]-3-[2-(2,6-dichlorophenyl)-6-quinolinyl]propanoyl}oxy)methyl pivalate 129.

Yield: 85%.
MS (MH$^+$): 647/649/651.

1.14. Synthesis of 2-{[(1-aminocyclopentyl)carbonyl]amino}-3-[2-(2,6-dichlorophenyl)-6-quinolinyl]propanoic acid 260

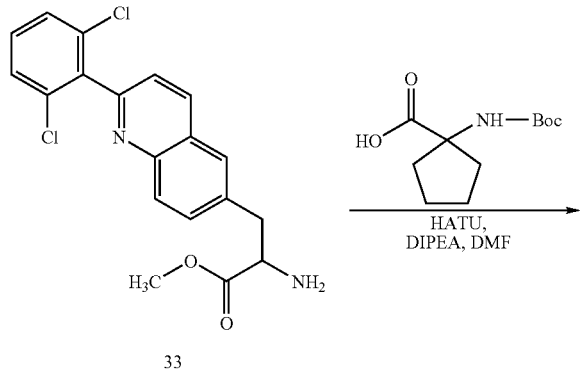

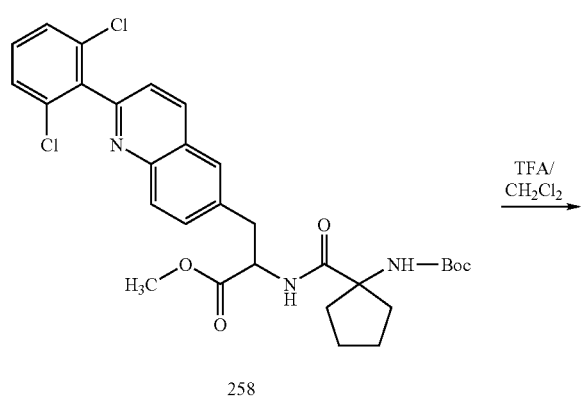

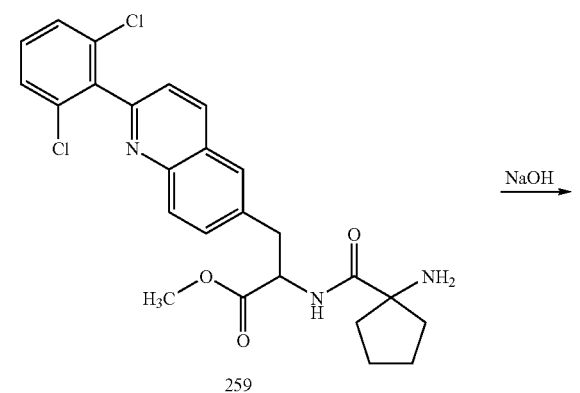

1.14.1. Synthesis of methyl 2-[({1-[(tert-butoxycarbonyl)amino]cyclopentyl}carbonyl)amino]-3-[2-(2,6-dichlorophenyl)-6-quinolinyl]propanoate 258.

Synthesis of methyl 2-[({1-[(tert-butoxycarbonyl)amino]cyclopentyl}carbonyl)amino]-3-[2-(2,6-dichlorophenyl)-6-quinolinyl]propanoate 258 from compound 33 follows the transformation of compound 33 into compound 35 as described in example 1.1.

Yield: 79%.
MS (MH+): 586/588/590.

1.14.2. Synthesis of methyl 2-{[(1-aminocyclopentyl)carbonyl]amino}-3-[2-(2,6-dichlorophenyl)-6-quinolinyl]propanoate 259

Synthesis of methyl 2-{[(1-aminocyclopentyl)carbonyl]amino}-3-[2-(2,6-dichlorophenyl)-6-quinolinyl]propanoate 259 from compound 258 follows the transformation of compound 6 into 33 as described is example 1.1.

Yield: 80%.
MS (MH+): 486/488/490.

1.14.3. Synthesis of 2-{[(1-aminocyclopentyl)carbonyl]amino}-3-[2-(2,6-dichlorophenyl)-6-quinolinyl]propanoic acid 260

Synthesis of 2-{[(1-aminocyclopentyl)carbonyl]amino}-3-[2-(2,6-dichlorophenyl)-6-quinolinyl]propanoic acid 260 from compound 259 follows the transformation of compound 35 into 38 as described is example 1.1.

Yield: 68%.
MS (MH+): 472/474/476.

1.15. Synthesis of tert-butyl 2-[(2,6-dichlorobenzoyl)amino]-3-[2-(2,6-dichlorophenyl)-6-quinolinyl]propanoate 264.

Compound 264 is synthesized from compound 38 according to method described in Takeda K., Synthesis (1994), 1063.

Yield: 16%.
MS (MH+): 589/591/593/595/597.

EXAMPLE 2

Quinolinyl Derivatives: Stereospecific Synthesis

2.1 Synthesis of (2S)-3-[2-(2,6-dichlorophenyl)-6-quinolinyl]-2-({[(2S)-1-(methylsulfonyl)piperidinyl]carbonyl}amino)propanoic acid 125

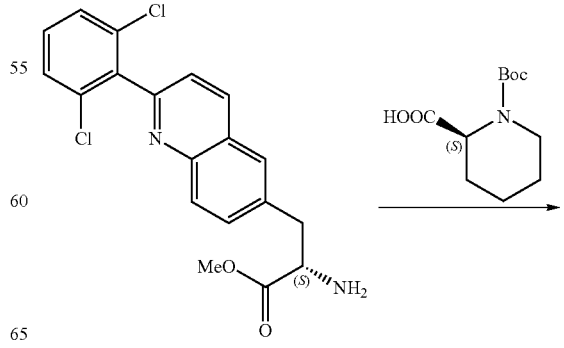

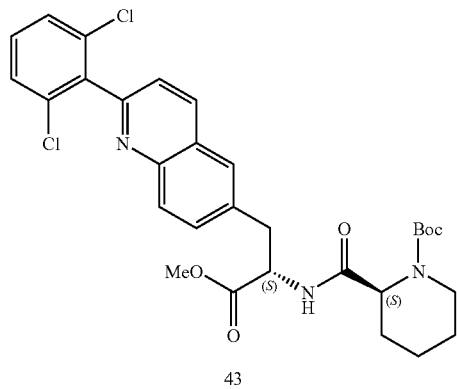

43

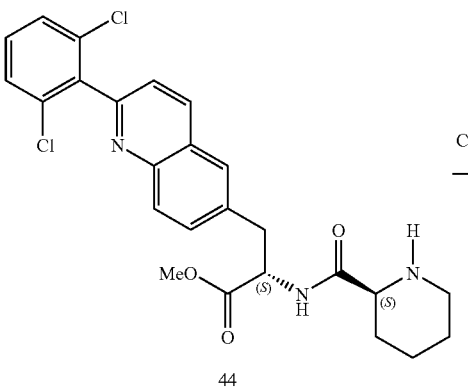

44

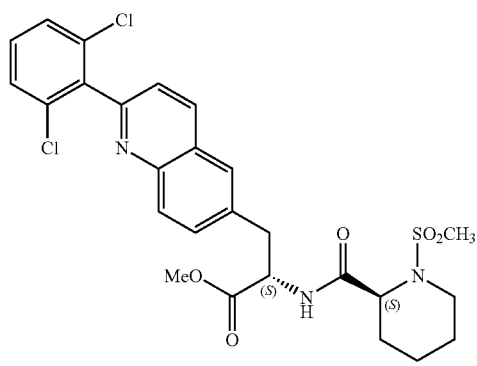

124

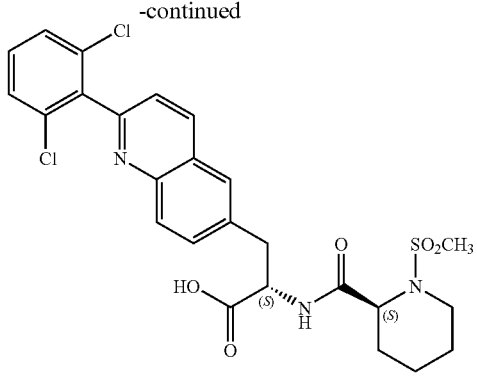

125

2.1.1 Synthesis of tert-butyl (2S)-2-{[(((1S)-1-([2-(2,6-dichlorophenyl)-6-quinolinyl]methyl}-2-methoxy-2-oxoethyl)amino]carbonyl)-1-piperidinecarboxylate 43

Synthesis of tert-butyl (2S)-2-{[((1S)-1-{[2-(2,6-dichlorophenyl)-6-quinolinyl]methyl}-2-methoxy-2-oxoethyl)amino]carbonyl}-1-piperidinecarboxylate 43 from compound 34 follows the transformation of compound 33 into compound 35 as described in scheme 1.
Yield: 71%.
MS (MH$^+$): 586/588/590.

2.1.2 Synthesis of methyl (2S)-3-[2-(2,6-dichlorophenyl)-6-quinolinyl]-2-{[(2S)-piperidinylcarbonyl]amino}propanoate 44

The deprotection of tert-butyl (2S)-2-{[((1S)-1-{[2-(2,6-dichlorophenyl)-6-quinolinyl]methyl}-2-methoxy-2-oxoethyl)amino]carbonyl}-1-piperidinecarboxylate 43 is performed according to the procedure described in 1.1.6 and gives methyl (2S)-3-[2-(2,6-dichlorophenyl)-6-quinolinyl]-2-{[(2S)-piperidinylcarbonyl]amino}propanoate 44.
Yield: 100%.
MS (MH$^+$): 486/488/490.

2.1.3 Synthesis of methyl (2S)-3-[2-(2,6-dichlorophenyl)-6-quinolinyl]-2-({[(2S)-1-(methylsulfonyl)piperidinyl]carbonyl}amino)propanoate 124

The mesylation of methyl (2S)-3-[2-(2,6-dichlorophenyl)-6-quinolinyl]-2-{[(2S)-piperidinylcarbonyl]amino}propanoate 44 is performed according to the procedure described in 1.3.2. using mesylchloride instead of p-toluenesulfonyl chloride and gives methyl (2S)-3-[2-(2,6-dichlorophenyl)-6-quinolinyl]-2-({[(2S)-1-(methylsulfonyl)piperidinyl]carbonyl}amino)propanoate 124.
Yield: 45%.
MS (MH$^+$): 564/566/568.

2.1.4 Synthesis of (2S)-3-[2-(2,6-dichlorophenyl)-6-quinolinyl]-2-({[(2S)-1-(methylsulfonyl)piperidinyl]carbonyl}amino)propanoic acid 125

The basic hydrolysis of methyl (2S)-3-[2-(2,6-dichlorophenyl)-6-quinolinyl]-2-({[(2S)-1-(methylsulfonyl)piperidinyl]carbonyl}amino)propanoate 124 is performed according to the procedure described in 1.3.3.

Yield: 78%.
MS (MH⁺): 550/552/554.

2.2 Synthesis of (2R)-2-[(2,6-dichlorobenzoyl)amino]-3-[2-(2,6-dichlorophenyl)-6-quinolinyl]propanoic acid 40 and (2S)-2-[(2,6-dichlorobenzoyl)amino]-3-[2-(2,6-dichlorophenyl)-6-quinolinyl]propanoic acid 39

2.2.1 Synthesis of methyl (2R)-2-[(2,6-dichlorobenzoyl)amino]-3-[2-(2,6-dichlorophenyl)-6-quinolinyl]propanoate 36 and methyl (2S)-2-[(2,6-dichlorobenzoyl)amino]-3-[2-(2,6-dichlorophenyl)-6-quinolinyl]propanoate 37

Compounds 36 and 37 are obtained by chiral chromatography of racemic compound 35 (Chiralpak AD 100*500 nm, flow: 300 ml/min, length wave: 220 nm, Hexane mixture/ethanol 50/50 as eluent).

Compound 36: second eluted.
Compound 37: first eluted.

2.2.2 Synthesis of (2R)-2-[(2,6-dichlorobenzoyl)amino]-3-[2-(2,6-dichlorophenyl)-6-quinolinyl]propanoic acid 40 and (2S)-2-[(2,6-dichlorobenzoyl)amino]-3-[2-(2,6-dichlorophenyl)-6-quinolinyl]propanoic acid 39

Hydrolysis at RT of methyl (2R)-2-[(2,6-dichlorobenzoyl)amino]-3-[2-(2,6-dichlorophenyl)-6-quinolinyl]propanoate 36 and methyl (2S)-2-[(2,6-dichlorobenzoyl)amino]-3-[2-(2,6-dichlorophenyl)-6-quinolinyl]propanoate 37 (as described in example 1.1 for the synthesis of compound 38) gives respectively (2R)-2-[(2,6-dichlorobenzoyl)amino]-3-[2-(2,6-dichlorophenyl)-6-quinolinyl]propanoic acid 40 and (2S)-2-[(2,6-dichlorobenzoyl)amino]-3-[2-(2,6-dichlorophenyl)-6-quinolinyl]propanoic acid 39.

2.3 Synthesis of (2S)-2-[(2,6-dichlorobenzoyl)amino]-3-[2-(2,6-dichlorophenyl)-6-quinolinyl]propanoic acid 39 according to scheme 13

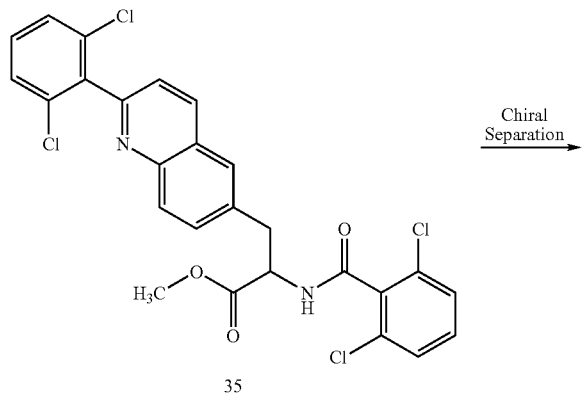

Scheme 12

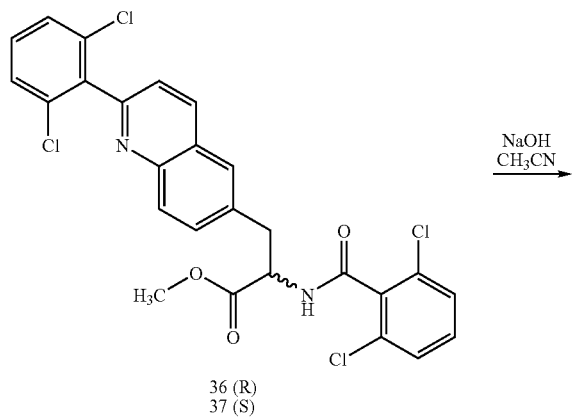

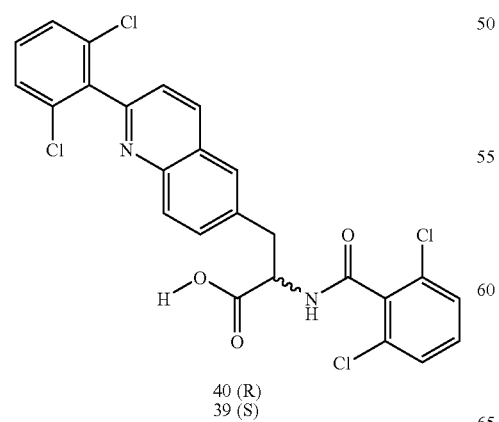

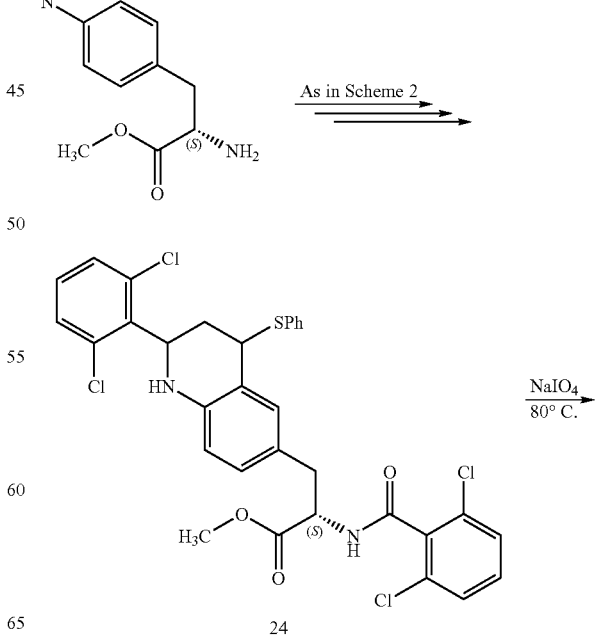

Scheme 13.

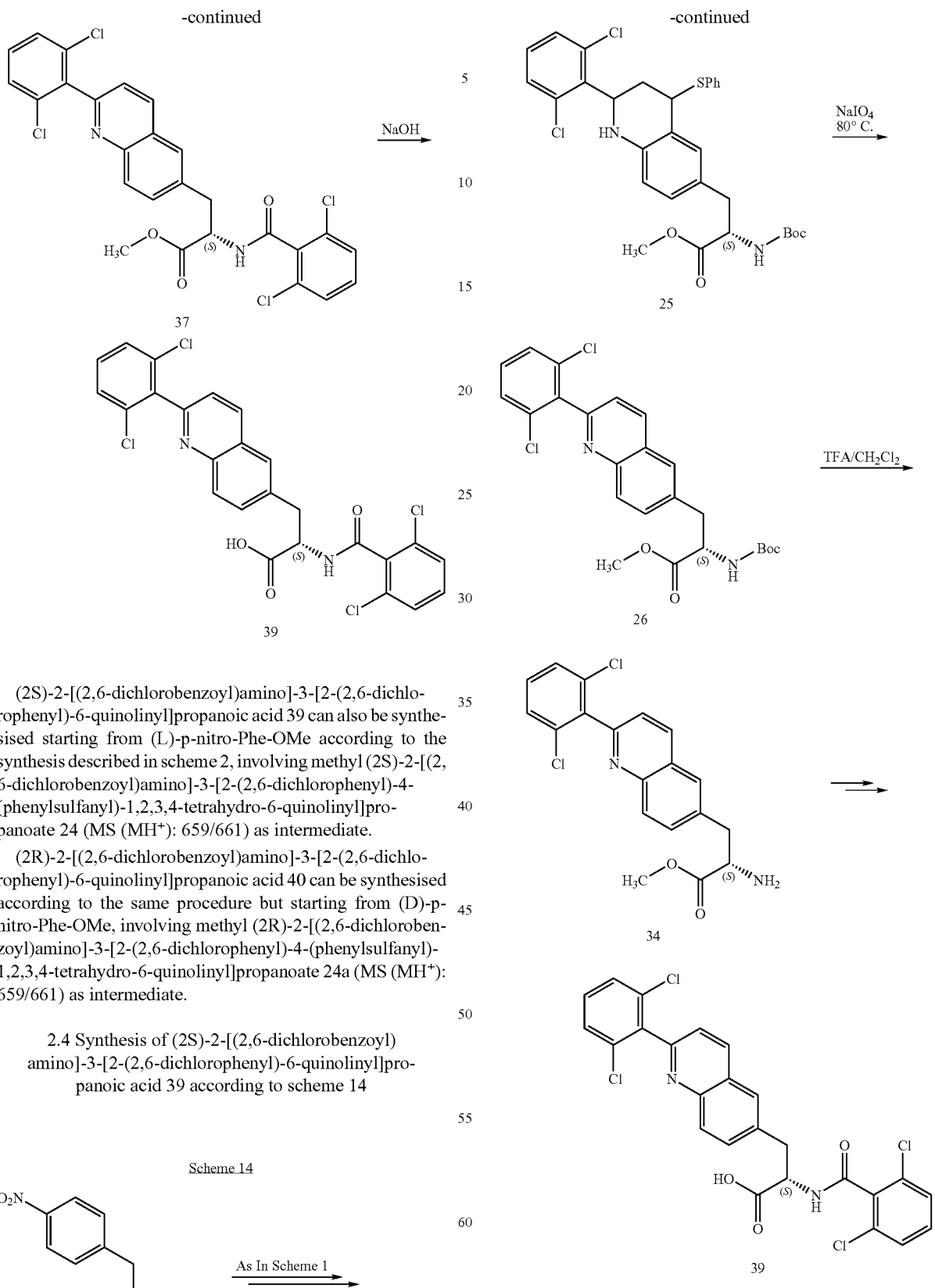

(2S)-2-[(2,6-dichlorobenzoyl)amino]-3-[2-(2,6-dichlorophenyl)-6-quinolinyl]propanoic acid 39 can also be synthesised starting from (L)-p-nitro-Phe-OMe according to the synthesis described in scheme 2, involving methyl (2S)-2-[(2,6-dichlorobenzoyl)amino]-3-[2-(2,6-dichlorophenyl)-4-(phenylsulfanyl)-1,2,3,4-tetrahydro-6-quinolinyl]propanoate 24 (MS (MH$^+$): 659/661) as intermediate.

(2R)-2-[(2,6-dichlorobenzoyl)amino]-3-[2-(2,6-dichlorophenyl)-6-quinolinyl]propanoic acid 40 can be synthesised according to the same procedure but starting from (D)-p-nitro-Phe-OMe, involving methyl (2R)-2-[(2,6-dichlorobenzoyl)amino]-3-[2-(2,6-dichlorophenyl)-4-(phenylsulfanyl)-1,2,3,4-tetrahydro-6-quinolinyl]propanoate 24a (MS (MH$^+$): 659/661) as intermediate.

2.4 Synthesis of (2S)-2-[(2,6-dichlorobenzoyl)amino]-3-[2-(2,6-dichlorophenyl)-6-quinolinyl]propanoic acid 39 according to scheme 14

Scheme 14

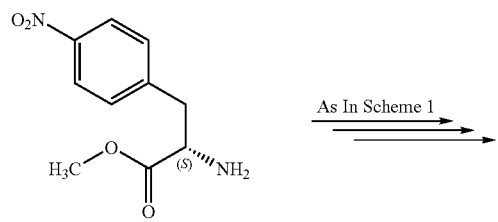

(2S)-2-[(2,6-dichlorobenzoyl)amino]-3-[2-(2,6-dichlorophenyl)-6-quinolinyl]propanoic acid 39 can also be synthesised starting from (L)-p-nitro-Phe-OMe according to the synthesis described in scheme 1, involving methyl (2S)-2-[(tert-butoxycarbonyl)amino]-3-[2-(2,6-dichlorophenyl)-4-(phenylsulfanyl)-1,2,3,4-tetrahydro-6-quinolinyl]propanoate 25 (MS (MH+): 587/589/591), methyl (2S)-2-[(tert-butoxycarbonyl)amino]-3-[2-(2,6-dichlorophenyl)-6-quinolinyl]propanoate 26 (MS (MH+): 475/477/479) and methyl (2S)-2-amino-3-[2-(2,6-dichlorophenyl)-6-quinolinyl]propanoate 34 (MS (MH+): 375/377/379) as intermediates.

Compounds described in table 6 can be synthesized as described for compound 25.

TABLE 6

| n° | IUPAC Name | MS (MH+) |
| --- | --- | --- |
| 25a | methyl (2R)-2-[(tert-butoxycarbonyl)amino]-3-[2-(2,6-dichlorophenyl)-4-(phenylsulfanyl)-1,2,3,4-tetrahydro-6-quinolinyl]propanoate | 587/589/591 |
| 25b | methyl (2S)-2-[(tert-butoxycarbonyl)amino]-3-[2-(2,6-dimethoxyphenyl)-4-(phenylsulfanyl)-1,2,3,4-tetrahydro-6-quinolinyl]propanoate | 579 |
| 25c | methyl (2R)-2-[(tert-butoxycarbonyl)amino]-3-[2-(2,6-dimethoxyphenyl)-4-(phenylsulfanyl)-1,2,3,4-tetrahydro-6-quinolinyl]propanoate | 579 |
| 25d | methyl (2S)-2-[(tert-butoxycarbonyl)amino]-3-[2-(2,6-dimethylphenyl)-4-(phenylsulfanyl)-1,2,3,4-tetrahydro-6-quinolinyl]propanoate | 547 |
| 25e | methyl (2S)-2-[(tert-butoxycarbonyl)amino]-3-[2-(3,5-dichloro-4-pyridinyl)-4-(phenylsulfanyl)-1,2,3,4-tetrahydro-6-quinolinyl]propanoate | 586/588/590 |

Compounds described in table 7 can be synthesized as described for compound 26.

TABLE 7

| n° | IUPAC Name | MS (MH+) |
| --- | --- | --- |
| 26a | methyl (2R)-2-[(tert-butoxycarbonyl)amino]-3-[2-(2,6-dichlorophenyl)-6-quinolinyl]propanoate | 475/477/479 |
| 26b | methyl (2S)-2-[(tert-butoxycarbonyl)amino]-3-[2-(2,6-dimethoxyphenyl)-6-quinolinyl]propanoate | 467 |
| 26c | methyl (2R)-2-[(tert-butoxycarbonyl)amino]-3-[2-(2,6-dimethoxyphenyl)-6-quinolinyl]propanoate | 467 |
| 26d | methyl (2S)-2-[(tert-butoxycarbonyl)amino]-3-[2-(2,6-dimethylphenyl)-6-quinolinyl]propanoate | 435 |
| 26e | methyl (2S)-2-[(tert-butoxycarbonyl)amino]-3-[2-(3,5-dichloro-4-pyridinyl)-6-quinolinyl]propanoate | 476/478/480 |

(2R)-2-[(2,6-dichlorobenzoyl)amino]-3-[2-(2,6-dichlorophenyl)-6-quinolinyl]propanoic acid 40 can be synthesised according to the same procedure but starting from (D)-p-nitro-Phe-OMe, involving methyl (2R)-2-[(tert-butoxycarbonyl)amino]-3-[2-(2,6-dichlorophenyl)-4-(phenylsulfanyl)-1,2,3,4-tetrahydro-6-quinolinyl]propanoate 25a, methyl (2R)-2-[(tert-butoxycarbonyl)amino]-3-[2-(2,6-dichlorophenyl)-6-quinolinyl]propanoate 26a and methyl (2R)-2-amino-3-[2-(2,6-dichlorophenyl)-6-quinolinyl]propanoate 34a (MS (MH+): 375/377/379) as intermediates.

2.5 Synthesis of (2S)-3-[2-(2,6-dichlorophenyl)-6-quinolinyl]-2-[({1-[2-(diethylamino)ethyl]cyclopentyl}carbonyl)amino]propanoic acid 272 according to the same method as described in 2.4 (scheme 14)

1-[2-(diethylamino)ethyl]cyclopentanecarboxylic acid 281 used for the synthesis of (2S)-3-[2-(2,6-dichlorophenyl)-6-quinolinyl]-2-[({1-[2-(diethylamino)ethyl]cyclopentyl}carbonyl)amino]propanoic acid 272 is synthesised according to scheme 15.

Scheme 15:

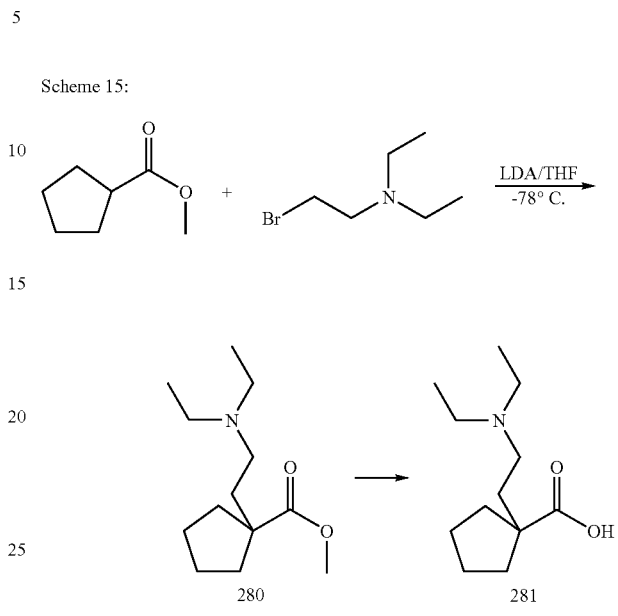

2.5.1 Synthesis of methyl 1-[2-(diethylamino)ethyl]cyclopentanecarboxylate 280

To methyl cyclopentanecarboxylate (1 g) in THF (8 ml) at −61° C. is added a solution of 2M LDA (9.8 ml). The mixture is stirred at room temperature for 15 minutes, then 2-bromo-N,N-diethylethanamine hydrobromide (2.04 g) is added at −61° C. The mixture is stirred for 5 minutes at this temperature, then at room temperature. The solution became yellow and was diluted with water (30 ml). The organic phase is extracted twice with a brine solution (30 ml). The pH of the organic phase is adjusted to 4 with 6N HCl. After decantation, the aqueous phase is extracted with $CH_2Cl_2$ (20 ml) and the pH of aqueous phase adjusted to 12 with 6 N NaOH. After decantation, the organic phase is dried over $MgSO_4$ and concentrated. The residue is treated with diethyl ether (10 ml) and the white solid is filtrated. Methyl 1-[2-(diethylamino)ethyl]cyclopentanecarboxylate 280 is obtained as a yellow liquid after concentration of the ether solution.

Yield: 79%.

MS (MH+): 228.

2.5.2 Synthesis of 1-[2-(diethylamino)ethyl]cyclopentanecarboxylic acid 281

Synthesis of 1-[2-(diethylamino)ethyl]cyclopentanecarboxylic acid 281 from 280 follows the transformation of compound 35 into 38 as described is example 1.1.

Yield: 94%.

MS (MH+): 214.

2.6 Synthesis of 2,6-dichloro-N-[(1R)-2-[2-(2,6-dichlorophenyl)-6-quinolinyl]-1-(hydroxymethyl)ethyl]benzamide 60 and 2,6-dichloro-N-[(1S)-2-[2-(2,6-dichlorophenyl)-6-quinolinyl]-1-(hydroxymethyl)ethyl]benzamide 59

Scheme 16.

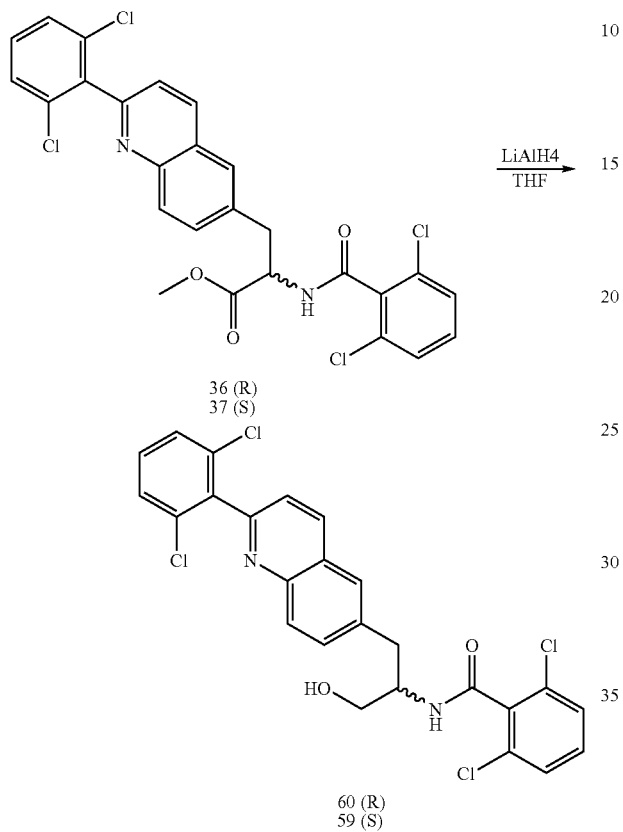

2.6.1 Synthesis of 2,6-dichloro-N-[(1R)-2-[2-(2,6-dichlorophenyl)-6-quinolinyl]-1-(hydroxymethyl)ethyl]benzamide 60

To methyl (2R)-2-[(2,6-dichlorobenzoyl)amino]-3-[2-(2,6-dichlorophenyl)-6-quinolinyl]propanoate 36 (0,222 g) in THF (1 ml) is added, at 0° C., LiAlH$_4$ (1.5 equ.). The solution is stirred at 0° C. for 1 hour. The reaction is quenched at −25° C. by successive additions of water (25 μl), 15% NaOH (25 μl) and water (75 μl). After evaporation of THF under vacuum, AcOEt is added. The organic phases are washed with water, brine, dried over MgSO$_4$ and evaporated. The resulting residue is purified over silica gel using CH$_2$Cl$_2$/CH$_3$OH/NH$_4$OH (99/1/0.1) as eluent to give 2,6-dichloro-N-[(1R)-2-[2-(2,6-dichlorophenyl)-6-quinolinyl]-1-(hydroxymethyl)ethyl]benzamide 60.

Yield: 62%.
MS (MH$^+$): 519/521/523.

2.6.2 Synthesis of 2,6-dichloro-N-[(1S)-2-[2-(2,6-dichlorophenyl)-6-quinolinyl]-1-(hydroxymethyl)ethyl]benzamide 59

The synthesis of 2,6-dichloro-N-[(1S)-2-[2-(2,6-dichlorophenyl)-6-quinolinyl]-1-(hydroxymethyl)ethyl]benzamide 59 follows the procedure described for compound 60 using methyl (2S)-2-[(2,6-dichlorobenzoyl)amino]-3-[2-(2,6-dichlorophenyl)-6-quinolinyl]propanoate 37 as starting material.

Yield: 48%.
MS (MH$^+$): 519/521/523.

2.7 Synthesis of (2S)-3-[2-(2,6-dichlorophenyl)-6-quinolinyl]-2-{[4-(4-piperidinylmethyl)benzoyl]amino}propanoic acid 263

Scheme 17.

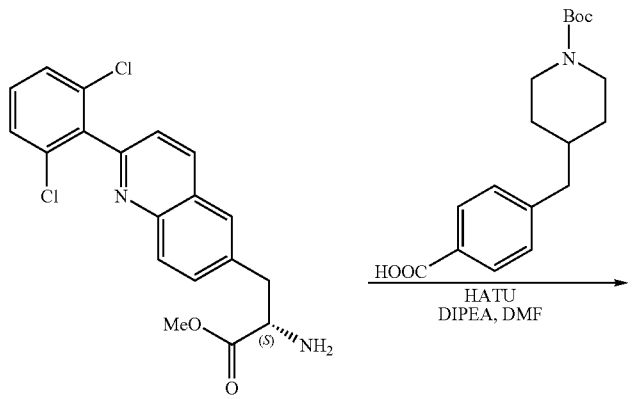

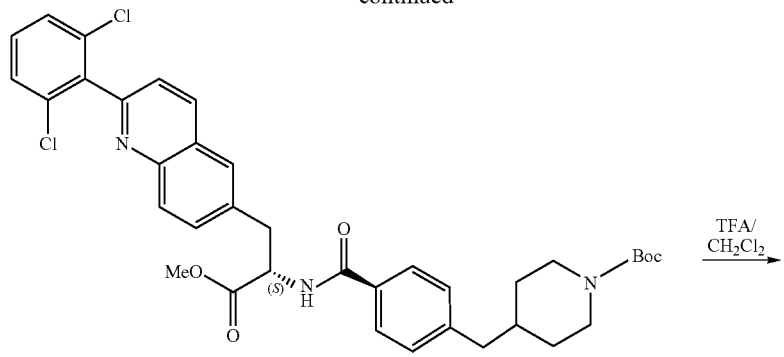

261

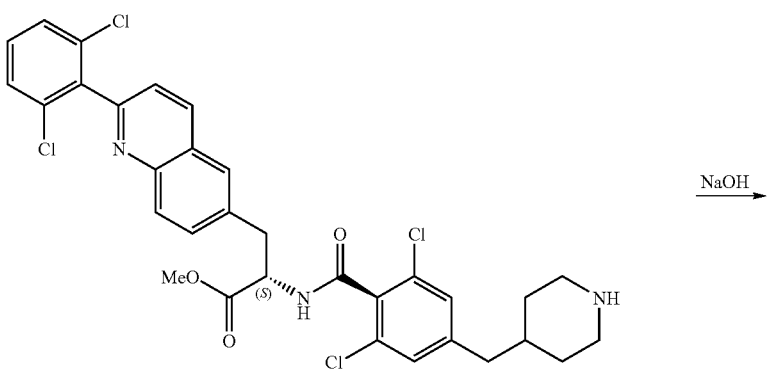

262

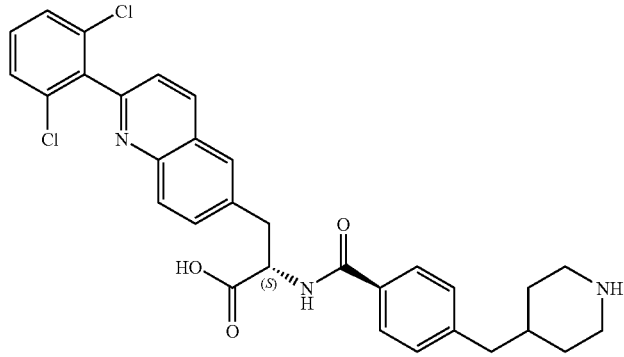

263

2.7.1 Synthesis of tert-butyl 4-(4-{[(((1S)-1-{[2-(2,6-dichlorophenyl)-6-quinolinyl]methyl}-2-methoxy-2-oxoethyl)amino]carbonyl}benzyl)-1-piperidinecarboxylate 261

Synthesis of tert-butyl 4-(4-{[(((1S)-1-{[2-(2,6-dichlorophenyl)-6-quinolinyl]methyl}-2-methoxy-2-oxoethyl)amino]carbonyl}benzyl)-1-piperidinecarboxylate 261 follows the transformation of compound 33 into compound 258 as described is example 1.14.

Yield: 86%.

MS (MH+): 676/678/680.

2.7.2 Synthesis of methyl (2S-3-[2-(2,6-dichlorophenyl)-6-quinolinyl]-2-{[4-(4-piperidinylmethyl)benzoyl]amino}propanoate 262

Synthesis of methyl (2S-3-[2-(2,6-dichlorophenyl)-6-quinolinyl]-2-{[4-(4-piperidinylmethyl)benzoyl]

amino}propanoate 262 follows the transformation of compound 258 into compound 259 as described is example 1.14.

Yield: 87%.

MS (MH+): 576/578/580.

2.7.3 Synthesis of (2S)-3-[2-(2,6-dichlorophenyl)-6-quinolinyl]-2-{[4-(4-piperidinylmethyl)benzoyl]amino}propanoic acid 263

Synthesis of (2S)-3-[2-(2,6-dichlorophenyl)-6-quinolinyl]-2-{[4-(4-piperidinylmethyl)benzoyl]amino}propanoic acid 263 follows the transformation of compound 259 into compound 260 as described is example 1.14.

Yield: 65%.

MS (MH+): 562/564/566.

EXAMPLE 3

Quinolinyl Derivatives: Combinatorial Chemistry

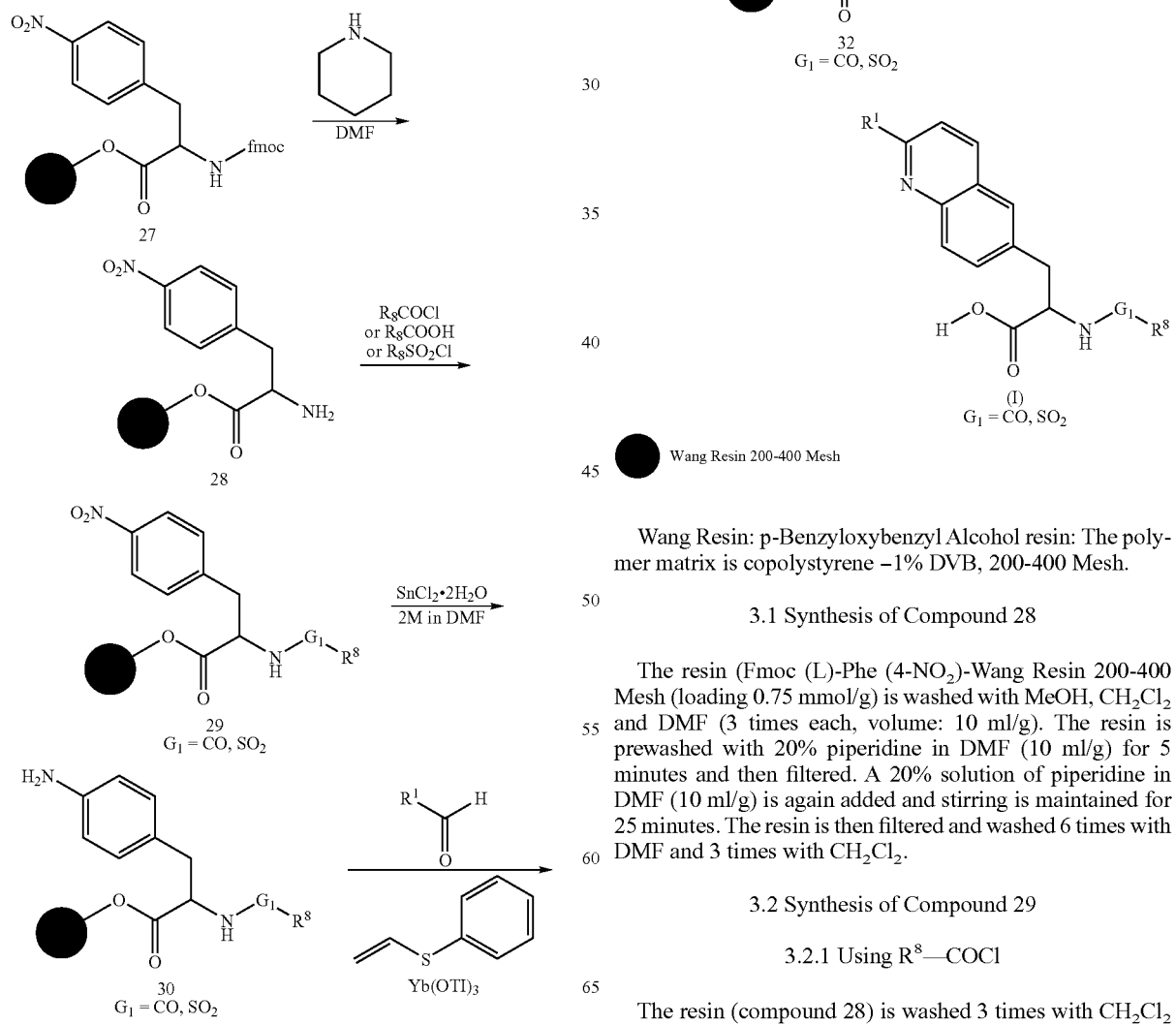
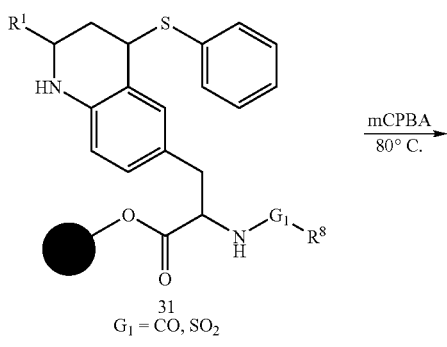
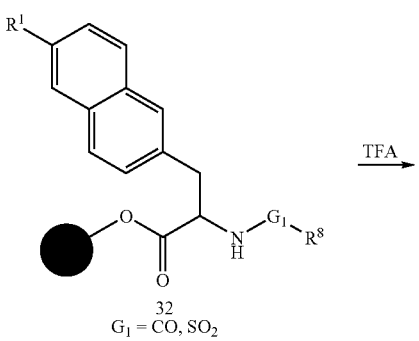
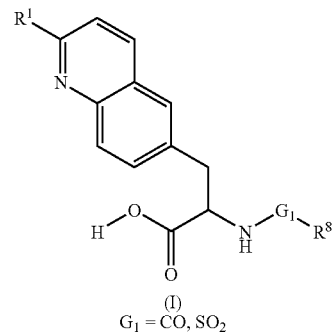

Wang Resin: p-Benzyloxybenzyl Alcohol resin: The polymer matrix is copolystyrene −1% DVB, 200-400 Mesh.

3.1 Synthesis of Compound 28

The resin (Fmoc (L)-Phe (4-NO$_2$)-Wang Resin 200-400 Mesh (loading 0.75 mmol/g) is washed with MeOH, CH$_2$Cl$_2$ and DMF (3 times each, volume: 10 ml/g). The resin is prewashed with 20% piperidine in DMF (10 ml/g) for 5 minutes and then filtered. A 20% solution of piperidine in DMF (10 ml/g) is again added and stirring is maintained for 25 minutes. The resin is then filtered and washed 6 times with DMF and 3 times with CH$_2$Cl$_2$.

3.2 Synthesis of Compound 29

3.2.1 Using R$^8$—COCl

The resin (compound 28) is washed 3 times with CH$_2$Cl$_2$ (volume: 10 ml/g). Ten equivalents of R$^8$—COCl in CH$_2$Cl$_2$ (10 ml/g) are then added, followed by 10 equivalents of DIPEA. Stirring is maintained for 2 h. The resin is filtered and washed with CH$_2$Cl$_2$, DMF and MeOH (3 times each, volume: 10 ml/g). Completion of the reaction is checked using a chloranil test on a small resin sample.

3.2.2 Using R$^8$—COOH

The resin (compound 28) is washed with CH$_2$Cl$_2$ followed by DMF (3 times each, volume: 10 ml/g). 10 equivalents of TBTU and 10 equivalents of HOBT (both as solids) are then added to the resin followed by R$^8$—COOH in DMF (10 ml/g). 30 equivalents of DIPEA are then added dropwise. Stirring is maintained for 2 h and the resin is filtered and washed 3 times with DMF, 3 times with CH$_2$Cl$_2$, 3 times with DMF and 3 times with MeOH (volume: 10 ml/g). Completion of the reaction is checked using a chloranil test on a small resin sample. If the reaction is not complete, the same procedure is started again but reaction is maintained overnight.

3.3 Synthesis of Compound 30

The resin (compound 29) is washed with CH$_2$Cl$_2$ followed by DMF (3 times each, volume: 10 ml/g). A 2M solution of 5 SnCl$_2$.2H$_2$O in DMF is then added (volume: 10 ml/g). Stirring is maintained 16 hours. The resin is then filtered and washed 6 times with DMF, 3 times with CH$_2$Cl$_2$, 3 times with CH$_2$Cl$_2$+10% TEA, 6 times with CH$_2$Cl$_2$ and 3 times with MeOH (volume: 10 ml/g).

3.4 Synthesis of Compound 31

The resin (compound 30) is washed 3 times with CH$_2$Cl$_2$ (volume: 10 ml/g). Ten equivalents of aldehyde R$^1$CHO in CH$_2$Cl$_2$ (5 ml/g) are added to the resin and the slurry is stirred for 10 minutes. Yb(OTf)$_3$ (0.05 equivalents, 5% mol) in CH$_3$CN (10 ml/g) is added, then 10 equivalents of phenyl vinyl sulfide, and the stirring is maintained for 20 hours. The resin is filtered and washed with MeOH, CH$_2$Cl$_2$, DMF, CH$_2$Cl$_2$ and MeOH (3 times each, volume: 10 ml/g).

3.5 Synthesis of Compound 32

The resin (compound 31) is washed 3 times with CH$_2$Cl$_2$ (10 ml/g). 1.3 equivalents of mCPBA in CH$_2$Cl$_2$ (10 ml/g) are subsequently added. After 1 hour of stirring the resin is filtered and washed with CH$_2$Cl$_2$, DMF, CH$_2$Cl$_2$ and MeOH (3 times each, 10 ml/g). The resin in DMF (10 ml/g) is then heated at 80° C. for 16 hours. The resin is then washed with DMF, CH$_2$Cl$_2$ and MeOH (3 times each, 10 ml/g).

3.6 Synthesis of Compounds of Formula I

The resin (compound 32, 500 mg/well) is dried under vacuum and the compounds of formula I are cleaved from by treating the resin 3 times with 5 ml solution of TFA/Water 95/5 during 15 minutes. After filtration, the resin is washed with the same solvent. Solvent is removed at RT under vacuum using a Genevac apparatus and the product is purified by reverse phase chromatography (CH$_3$CN/water/0.1% TFA).

Average overall yield: +/−30%.

EXAMPLE 4

Naphthyl Derivatives: Racemic Synthesis 4.1 Synthesis of 2-[(2,6-dichlorobenzoyl)amino]-3-[6-(2,6-dimethoxyphenyl)-2-naphthyl]propanoic acid 210

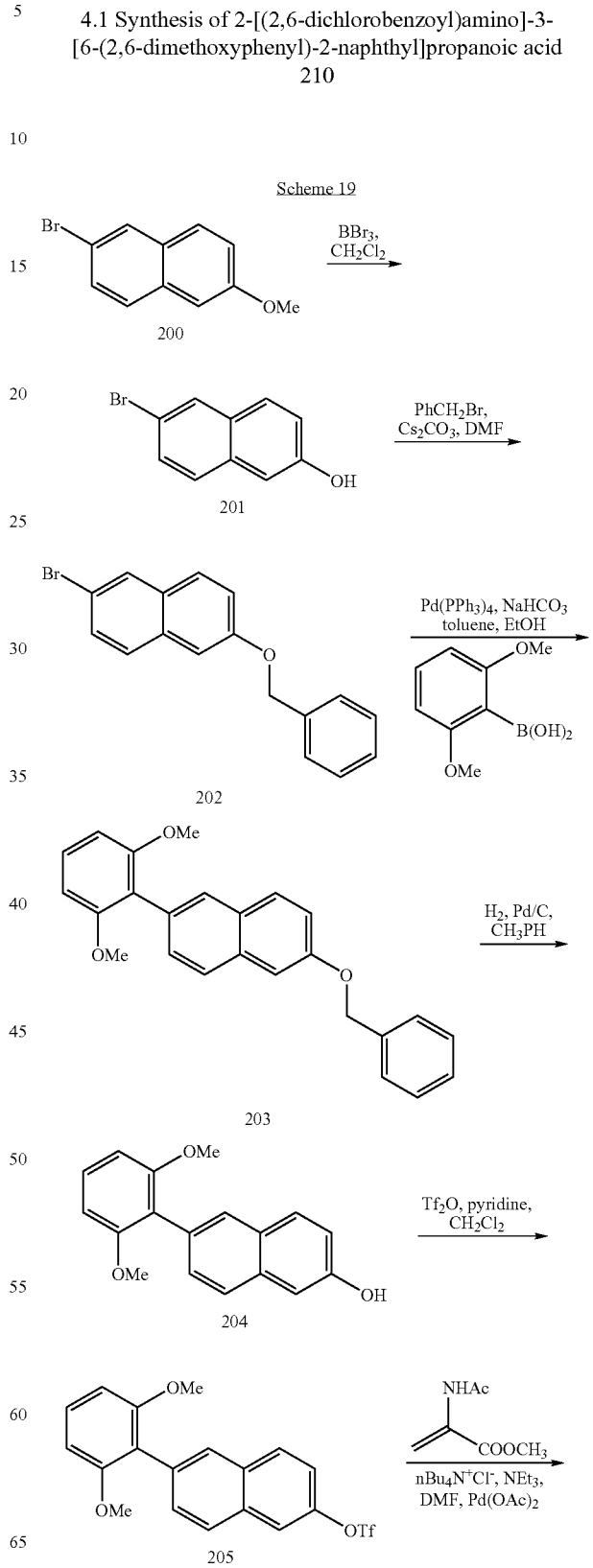

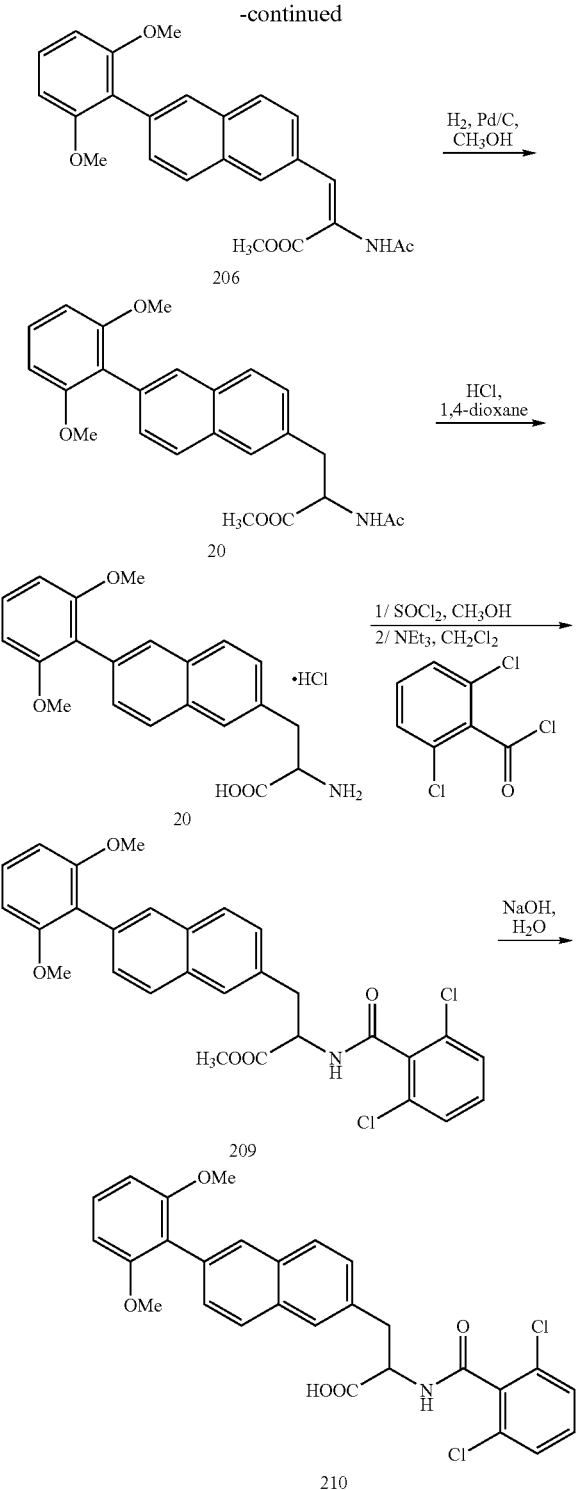

4.1.1 Synthesis of 6-bromo-2-naphthol 201

Deprotection of 2-bromo-6-methoxynaphthalene 200 as described in 1.9.2 gives 6-bromo-2-naphthol 201.
Yield: 94%.
MS (MH$^+$): 227.

4.1.2 Synthesis of 2-(benzyloxy)-6-bromonaphthalene 202

Protection of 6-bromo-2-naphthol 201 as described in 1.8.2 gives 2-(benzyloxy)-6-bromonaphthalene 202.
Yield: 98%.
MS (MH$^+$): 313.

4.1.3 Synthesis of 2-(benzyloxy)-6-(2,6-dimethoxyphenyl)naphthalene 203

Reaction of 2-(benzyloxy)-6-bromonaphthalene 202 with 2,6-dimethoxyboronic acid as described in 1.9.1 gives 2-(benzyloxy)-6-(2,6-dimethoxyphenyl)naphthalene 203.
Yield: 95%.
MS (MH$^+$): 370.

4.1.4 Synthesis of 6-(2,6-dimethoxyphenyl)-2-naphthol 204

Deprotection of 2-(benzyloxy)-6-(2,6-dimethoxyphenyl) naphthalene 203 as described in 1.8.4 gives 6-(2,6-dimethoxyphenyl)-2-naphthol 204.
Yield: 92%.
MS (MH$^+$): 281.

4.1.5 Synthesis of 6-(2,6-dimethoxyphenyl)-2-naphthyl trifluoromethanesulfonate 205

Reaction of 6-(2,6-dimethoxyphenyl)-2-naphthol 204 with trifluoromethanesulfonic anhydride as described in 1.8.5 gives 6-(2,6-dimethoxyphenyl)-2-naphthyl trifluoromethanesulfonate 205.
Yield: 80%.
MS (MH$^+$): 413.

4.1.6 Synthesis of methyl (2-(acetylamino)-3-[6-(2,6-dimethoxyphenyl)-2-naphthyl]-2-propenoate 206

Reaction of 6-(2,6-dimethoxyphenyl)-2-naphthyl trifluoromethanesulfonate 205 with methyl-2-N-acetyl-acrylate as described in 1.8.7 gives methyl (2-(acetylamino)-3-[6-(2,6-dimethoxyphenyl)-2-naphthyl]-2-propenoate 206.
Yield: 88%.
MS (MH$^+$): 406.

4.1.7 Synthesis of methyl 2-(acetylamino)-3-[6-(2,6-dimethoxyphenyl)-2-naphthyl]propanoate 207

Hydrogenation of methyl (2-(acetylamino)-3-[6-(2,6-dimethoxyphenyl)-2-naphthyl]-2-propenoate 206 as described in 1.8.8. gives methyl 2-(acetylamino)-3-[6-(2,6-dimethoxyphenyl)-2-naphthyl]propanoate 207.
Yield: 99%.
MS (MH$^+$): 408.

4.1.8 Synthesis of 2-amino-3-[6-(2,6-dimethoxyphenyl)-2-naphthyl]propanoic acid hydrochloride 208

To a solution of 1,4-dioxane (1 ml) are added successively 6 N HCl (3 ml) and methyl 2-(acetylamino)-3-[6-(2,6-dimethoxyphenyl)-2-naphthyl]propanoate 207 (0.135 g). The solution is stirred and heated at reflux for 4 hours, then cooled, and diethyl ether (5 ml) is added. The aqueous phase is extracted with diethyl ether (35 ml). The organic phase is concentrated under vacuum. The resulting residue is dried overnight under high pression to give 2-amino-3-[6-(2,6-dimethoxyphenyl)-2-naphthyl]propanoic acid hydrochloride 208.

Yield: 81%.
MS (MH+): 352.

4.1.9 Synthesis of methyl 2-[(2,6-dichlorobenzoyl)amino]-3-[6-(2,6-dimethoxyphenyl)-2-naphthyl]propanoate 209

Esterification of 2-amino-3-[6-(2,6-dimethoxyphenyl)-2-naphthyl]propanoic acid hydrochloride 208 as described in 1.1.1 followed by acylation as described in 1.8.10 gives methyl 2-[(2,6-dichlorobenzoyl)amino]-3-[6-(2,6-dimethoxyphenyl)-2-naphthyl]propanoate 209.

Yield: 72%.
MS (MH+): 538/540/542.

4.1.10 Synthesis of 2-[(2,6-dichlorobenzoyl)amino]-3-[6-(2,6-dimethoxyphenyl)-2-naphthyl]propanoic acid 210

Hydrolysis of methyl 2-[(2,6-dichlorobenzoyl)amino]-3-[6-(2,6-dimethoxyphenyl)-2-naphthyl]propanoate 209 as described in 1.8.11 gives 2-[(2,6-dichlorobenzoyl)amino]-3-[6-(2,6-dimethoxyphenyl)-2-naphthyl]propanoic acid 210.

Yield: 64%.
MS (MH+): 524/526/528.

4.2 Synthesis of 2-[(2,6-dichlorobenzoyl)amino]-3-[6-(2,6-dichlorophenyl)-2-naphthyl]propanoic acid 214

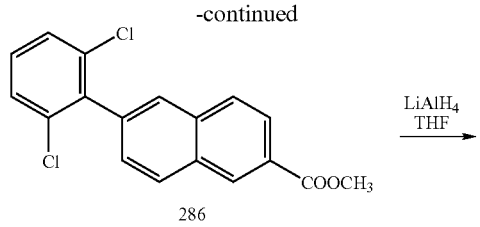
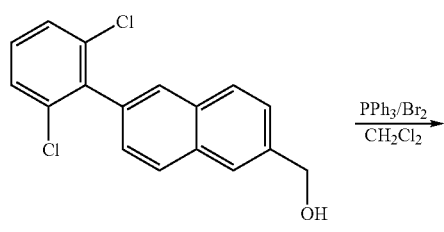
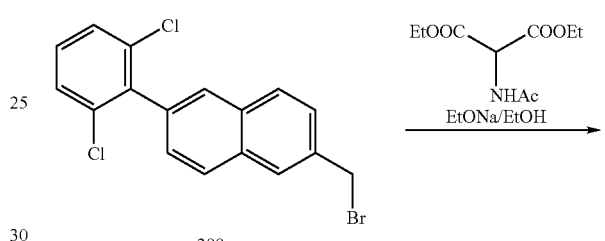
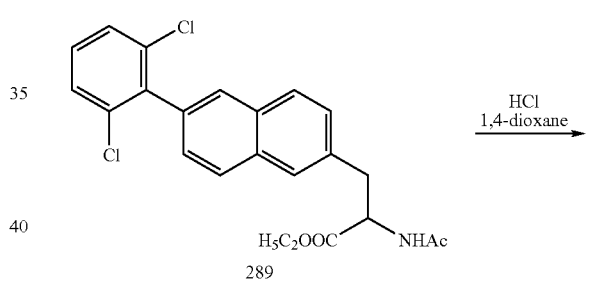
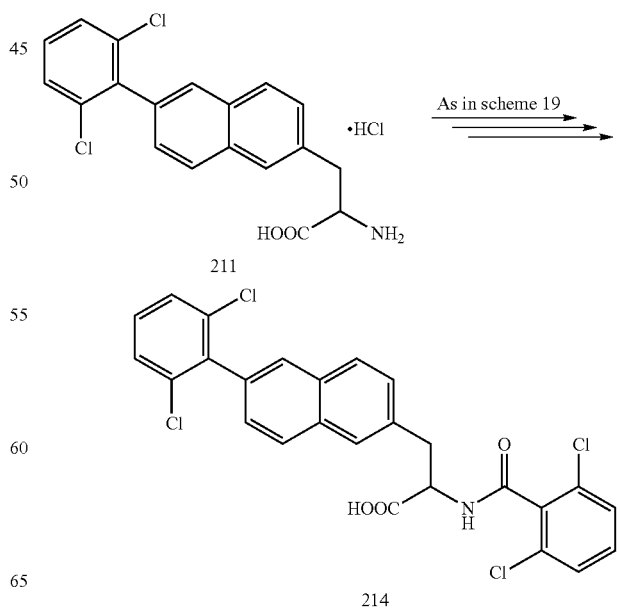

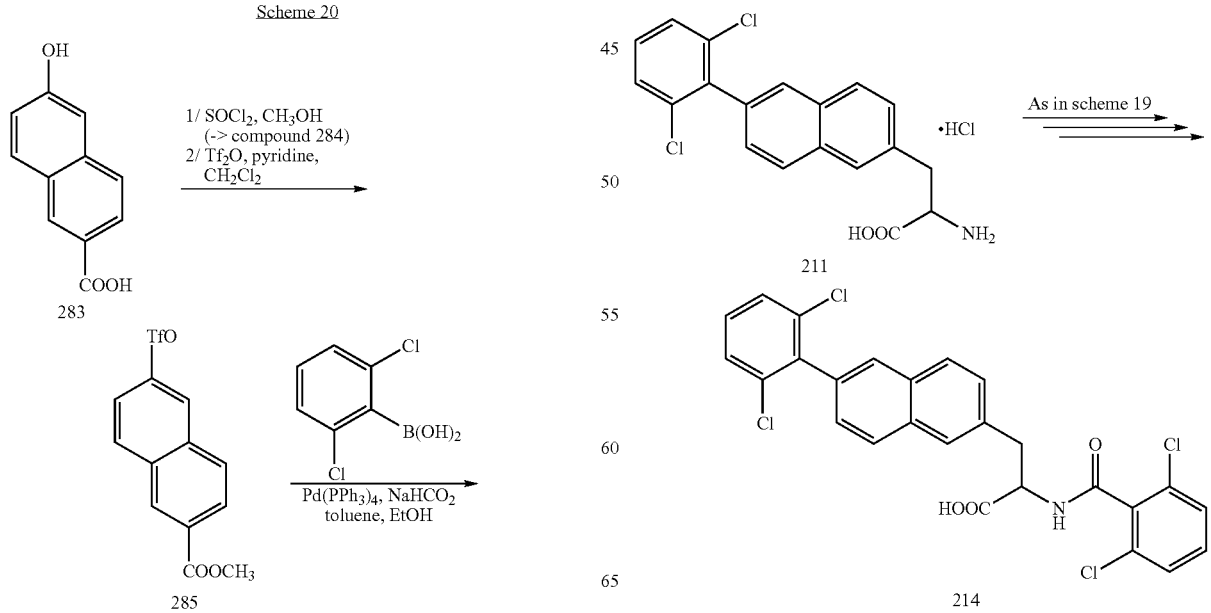

4.2.1 Synthesis of methyl 6-hydroxy-2-naphthoate 284

Reaction of 6-hydroxy-2-naphthoic acid 283 with $SOCl_2$ as described in 1.1.1. gives methyl 6-hydroxy-2-naphthoate 284.
Yield: 97%.
MS ($MH^+$): 202.

4.2.2 Synthesis of methyl 6-{[(trifluoromethyl)sulfonyl]oxy}-2-naphthoate 285

Reaction of methyl 6-hydroxy-2-naphthoate 284 with trifluoromethanesulfonic anhydride as described in 4.1.5. gives methyl 6-{[(trifluoromethyl)sulfonyl]oxy}-2-naphthoate 285.
Yield: 90%.
MS ($MH^+$): 334.

4.2.3 Synthesis of methyl 6-(2,6-dichlorophenyl)-2-naphthoate 286

Reaction of methyl 6-{[(trifluoromethyl)sulfonyl]oxy}-2-naphthoate 285 as described in example 4.1.3. gives methyl 6-(2,6-dichlorophenyl)-2-naphthoate 286.
Yield: 93%.
MS ($MH^+$): 331.

4.2.4 Synthesis of [6-(2,6-dichlorophenyl)-2-naphthyl]methanol 287

Reaction of methyl 6-(2,6-dichlorophenyl)-2-naphthoate 286 as described in 2.5.1. gives [6-(2,6-dichlorophenyl)-2-naphthyl]methanol 287.
Yield: 98%.
MS ($MH^+$): 303.

4.2.5 Synthesis of 2-(bromomethyl)-6-(2,6-dichlorophenyl)naphthalene 288

To a solution of $PPh_3$ (0.251 g) in $CH_2Cl_2$ (1 ml) is added drop by drop, at 0° C., a solution of bromine (0.049 ml) in $CH_2Cl_2$ (1 ml). After 30 min, [6-(2,6-dichlorophenyl)-2-naphthyl]methanol 287 (0.242 g) is added. The mixture is stirred, under argon, at RT for 6 h. Water (2 ml) is added. The aqueous phase is extracted with $CH_2Cl_2$ (3×5 ml). The organic phases are dried over $MgSO_4$ and evaporated under vacuum. The residue is purified by silica gel chromatography using AcOEt/cyclohexane 40/60 as eluent.
Yield: 95%.
MS ($MH^+$): 366.

4.2.6 Synthesis of ethyl 2-(acetylamino)-3-[6-(2,6-dichlorophenyl)-2-naphthyl]propanoate 289

To a solution of Na (0.092 g) in ethanol (5 ml) is added diethyl 2-(acetylamino)malonate (0.870 g). The mixture is stirred for 1 h. A solution of 2-(bromomethyl)-6-(2,6-dichlorophenyl)naphthalene 288 (0.978 g) in ethanol (5 ml) is added, under argon. The mixture is stirred under reflux for 5 h. After addition of water (5 ml), the solution is concentrated under vacuum and then diluted with AcOEt (5 ml). The aqueous phase is extracted with AcOEt (3×15 ml). The organic phases are dried over $MgSO_4$, filtrated and evaporated under vacuum. The residue is purified by silica gel chromatography using AcOEt/cyclohexane 20/80 then (40/60) as eluent.

Yield: 54%.
MS ($MH^+$): 430.

4.2.7 Synthesis of 2-amino-3-[6-(2,6-dichlorophenyl)-2-naphthyl]propanoic acid hydrochloride 211

Reaction of ethyl 2-(acetylamino)-3-[6-(2,6-dichlorophenyl)-2-naphthyl]propanoate 289 with HCl as described in 4.1.8. gives 2-amino-3-[6-(2,6-dichlorophenyl)-2-naphthyl]propanoic acid hydrochloride 211.
Yield: 91%.
MS ($MH^+$): 396.

4.2.8 Synthesis of 2-[(2,6-dichlorobenzoyl)amino]-3-[6-(2,6-dichlorophenyl)-2-naphthyl]propanoic acid 214

2-[(2,6-dichlorobenzoyl)amino]-3-[6-(2,6-dichlorophenyl)-2-naphthyl]propanoic acid 214 can be synthesised starting from 2-amino-3-[6-(2,6-dichlorophenyl)-2-naphthyl]propanoic acid hydrochloride 211 according to the synthesis described in scheme 19.

EXAMPLE 5

Naphthyl derivatives: stereospecific synthesis. Synthesis of (−)- and (+)-2-[(2,6-dichlorobenzoyl)amino]-3-[6-(2,6-dimethoxyphenyl)-2-naphthyl]propanoic acid 217 and 218

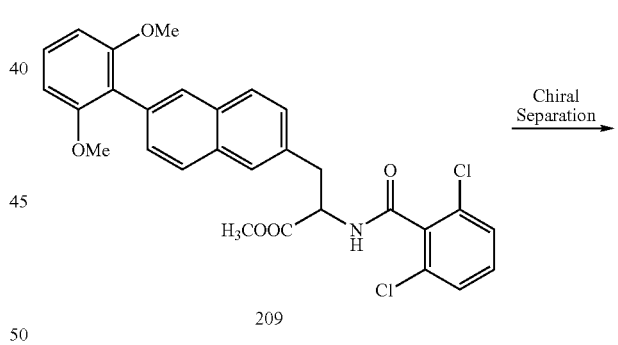

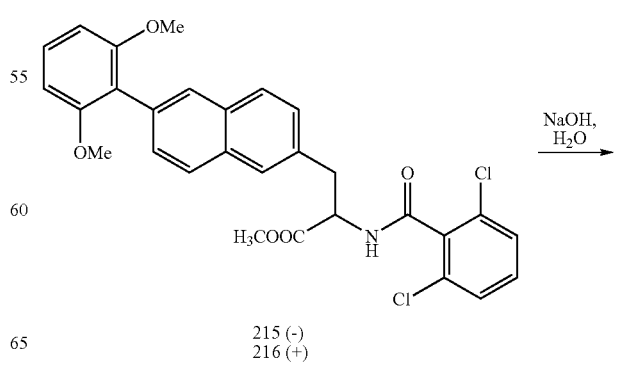

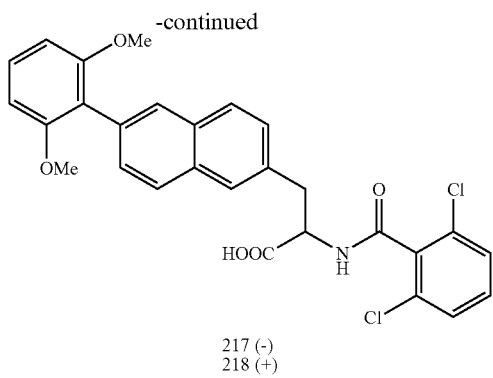

217 (−)
218 (+)

5.1 Synthesis of (−) and (+) methyl 2-[(2,6-dichlorobenzoyl)amino]-3-[6-(2,6-dimethoxyphenyl)-2-naphthyl]propanoate 215 and 216

Synthesis of (−) and (+) methyl 2-[(2,6-dichlorobenzoyl) amino]-3-[6-(2,6-dimethoxyphenyl)-2-naphthyl]propanoate 215 and 216 follows the transformation of compound 35 into 36 and 37 as described is example 2.2.

MS (MH$^+$): 538/540/542.

5.2. Synthesis of (−) and (+) 2-[(2,6-dichlorobenzoyl)amino]-3-[6-(2,6-dimethoxyphenyl)-2-naphthyl]propanoic acid 217 and 218

According to the transformation of compounds 36 and 37 into 40 and 39 as described in example 2.2.

Yield: respectively 83% and 84%.

MS (MH$^+$): 524/526/228.

Compounds described in table 8 can be synthesized according to one of these methods.

In the table, the stereochemical information is contained in the two columns headed 'configuration data'. The second column indicates whether a compound is a pure configuration isomer or enantiomer (Pure), a racemate (Rac) or is a mixture of two or more stereoisomers, possibly in unequal proportions (Mixt). The first column contains the stereochemical assignment for each recognised center, following the IUPAC numbering used in the preceding column. A number alone indicates the existence of both configurations at that center. A number followed by 'R' or 'S' indicates the known absolute configuration at that center. A number followed by '§' indicates the existence of only one but unknown absolute configuration at that center. The letter (A, B, C, D) in front is a way of distinguishing the various configuration isomers, enantiomers or racemates of the same structure.

TABLE 8

| n° | Configuration data | | IUPAC Name | $\alpha_D$ (25° C.) or ee | LC-MS (MH$^+$) |
|---|---|---|---|---|---|
| 33 | 2 | Rac | methyl 2-amino-3-[2-(2,6-dichlorophenyl)-6-quinolinyl]propanoate | | 375/377/379 |
| 34 | 2S | Pure | methyl (2S)-2-amino-3-[2-(2,6-dichlorophenyl)-6-quinolinyl]propanoate | | 375/377/379 |
| 34a | 2R | Pure | methyl (2R)-2-amino-3-[2-(2,6-dichlorophenyl)-6-quinolinyl]propanoate | | 375/377/379 |
| 35 | 2 | Rac | methyl 2-{[(2,6-dichlorophenyl)carbonyl]amino}-3-[2-(2,6-dichlorophenyl)-6-quinolinyl]propanoate | | 547/549/551 |
| 36 | 2R | Pure | methyl (2R)-2-[(2,6-dichlorobenzoyl)amino]-3-[2-(2,6-dichlorophenyl)-6-quinolinyl]propanoate | +52.77 (CH$_3$CN, 1%) | 547/549/551 |
| 37 | 2S | Pure | methyl (2S)-2-[(2,6-dichlorobenzoyl)amino]-3-[2-(2,6-dichlorophenyl)-6-quinolinyl]propanoate | −51.95 (CH$_3$CN, 1%) | 547/549/551 |
| 38 | 2 | Rac | 2-[(2,6-dichlorobenzoyl)amino]-3-[2-(2,6-dichlorophenyl)-6-quinolinyl]propanoic acid | | 533/535/537 |
| 39 | 2S | Pure | (2S)-2-[(2,6-dichlorobenzoyl)amino]-3-[2-(2,6-dichlorophenyl)-6-quinolinyl]propanoic acid | −61.92 (CH$_3$OH, 1%) | 533/535/537 |
| 40 | 2R | Pure | (2R)-2-[(2,6-dichlorobenzoyl)amino]-3-[2-(2,6-dichlorophenyl)-6-quinolinyl]propanoic acid | +57.25 (CH$_3$OH, 1%) | 533/535/537 |
| 41 | 2 | Rac | methyl 2-[(2,6-dichlorobenzyl)amino]-3-[2-(2,6-dichlorophenyl)-6-quinolinyl]propanoate | | 533/535/537 |
| 42 | 2S, 1 | Mixt | tert-butyl (2S)-2-{[(1-{[2-(2,6-dichlorophenyl)-6-quinolinyl]methyl}-2-methoxy-2-oxoethyl)amino]carbonyl}-1-piperidinecarboxylate | | 586/588/590 |
| 43 | 2S, 1S | Pure | tert-butyl (2S)-2-{[((1S)-1-{[2-(2,6-dichlorophenyl)-6-quinolinyl]methyl}-2-methoxy-2-oxoethyl)amino]carbonyl}-1-piperidinecarboxylate | | 586/588/590 |
| 44 | 2S, 2S | Pure | methyl (2S)-3-[2-(2,6-dichlorophenyl)-6-quinolinyl]-2-{[(2S)-piperidinylcarbonyl]amino}propanoate | | 486/488/490 |
| 45 | 2, 2S | Mixt | methyl 3-[2-(2,6-dichlorophenyl)-6-quinolinyl]-2-{[(2S)-piperidinylcarbonyl]amino}propanoate | | 486/488/490 |
| 46 | 2, 2S | Mixt | methyl 3-[2-(2,6-dichlorophenyl)-6-quinolinyl]-2-[({(2S)-1-[(4-methylphenyl)sulfonyl]piperidinyl}carbonyl)amino]propanoate | | 640/642/644 |
| 47 | 2 | Rac | methyl 2-({[1-(4-chlorophenyl)cyclopentyl]carbonyl}amino)-3-[2-(2,6-dichlorophenyl)-6-quinolinyl]propanoate | | 581/583/585 |
| 48 | 2S, 3aS, 7aS, 2 | Mixt | tert-butyl (2S,3aS,7aS)-2-{[(1-{[2-(2,6-dichlorophenyl)-6-quinolinyl]methyl}-2-methoxy-2-oxoethyl)amino]carbonyl}octahydro-1H-indole-1-carboxylate | | 626/628/630 |
| 49 | 2, 2S, 3aS, 7aS | Mixt | methyl 2-{[((2S,3aS,7aS)-octahydro-1H-indol-2-ylcarbonyl]amino}-3-[2-(2,6-dichlorophenyl)-6-quinolinyl]propanoate | | 526/528/530 |
| 50 | 2, 2S, 3aS, 7aS | Mixt | methyl 2-[({(2S,3aS,7aS)-1-[(4-methylphenyl)sulfonyl]octahydro-1H-indol-2-yl}carbonyl)amino]-3-[2-(2,6-dichlorophenyl)-6-quinolinyl]propanoate | | 680/682/684 |
| 51 | 2 | Rac | methyl 2-[(2,6-dichlorobenzyl)(methyl)amino]-3-[2-(2,6-dichlorophenyl)-6-quinolinyl]propanoate | | 547/549/551 |
| 52 | 2 | Rac | methyl 2-{[(2,6-dichloroanilino)carbonyl]amino}-3-[2-(2,6-dichlorophenyl)-6-quinolinyl]propanoate | | 562/564/566 |
| 53 | 2 | Rac | methyl 2-amino-3-[2-(phenyloxy)-6-quinolinyl]propanoate | | 322 |
| 54 | 2 | Rac | methyl 2-{[(2,6-dichlorophenyl)carbonyl]amino}-3-[2-(phenyloxy)-6-quinolinyl]propanoate | | 495 |

TABLE 8-continued

| n° | Configuration data | | IUPAC Name | α_D (25° C.) or ee | LC-MS (MH+) |
|---|---|---|---|---|---|
| 55 | 2 | Rac | methyl 3-[2-(2,6-dimethylphenyl)-6-quinolinyl]-2-hydroxypropanoate | | 377 |
| 56 | 2 | Rac | methyl 2-{[(2,6-dichlorophenyl)methyl]oxy}-3-[2-(2,6-dichlorophenyl)-6-quinolinyl]propanoate | | 534 |
| 57 | 2 | Rac | 1-{[2-(2,6-dichlorophenyl)-6-quinolinyl]methyl}-2-(methyloxy)-2-oxoethyl 2,6-dichlorobenzoate | | 550 |
| 58 | 1 | Rac | 2,6-dichloro-N-{1-cyano-2-[2-(2,6-dichlorophenyl)-6-quinolinyl]ethyl}benzamide | | 514/516/518 |
| 59 | 1S | Pure | 2,6-dichloro-N-[(1S)-2-[2-(2,6-dichlorophenyl)-6-quinolinyl]-1-(hydroxymethyl)ethyl]benzamide | −36.25 ($CH_3OH$, 1%) | 519/521/523 |
| 60 | 1R | Pure | 2,6-dichloro-N-[(1R)-2-[2-(2,6-dichlorophenyl)-6-quinolinyl]-1-(hydroxymethyl)ethyl]benzamide | +68.10 ($CH_3OH$, 1%) | 519/521/523 |
| 61 | 2 | Rac | 2-(benzoylamino)-3-[2-(2,6-dichlorophenyl)-6-quinolinyl]propanoic acid | | 465/467/469 |
| 62 | 2 | Rac | 2-[(2,6-dichlorobenzyl)amino]-3-[2-(2,6-dichlorophenyl)-6-quinolinyl]propanoic acid | | 519/521/523 |
| 63 | 2, 4R | Mixt | 2-({[(4R)-3-acetyl-1,3-thiazolidin-4-yl]carbonyl}amino)-3-[2-(2,6-dichlorophenyl)-6-quinolinyl]propanoic acid | | 518/520/522 |
| 64 | 2 | Rac | 2-{[(2,6-dichlorophenyl)(ethoxy)methylene]amino}-3-[2-(2,6-dichlorophenyl)-6-quinolinyl]propanoic acid | | 561/563 |
| 65 | 2 | Rac | 2-[(2,6-dichlorobenzoyl)amino]-3-[2-(2,6-dimethoxyphenyl)-6-quinolinyl]propanoic acid | | 525/527/529 |
| 66 | 2 | Rac | 2-[(2,6-dichlorobenzyl)(methyl)amino]-3-[2-(2,6-dichlorophenyl)-6-quinolinyl]propanoic acid | | 533/535/537 |
| 67 | 2 | Rac | 3-[2-(2,6-dichlorophenyl)-6-quinolinyl]-2-[(2,6-dimethoxybenzoyl)amino]propanoic acid | | 525/527/529 |
| 68 | 2 | Rac | 3-[2-(2,6-dichlorophenyl)-6-quinolinyl]-2-[(2,6-dimethylbenzoyl)amino]propanoic acid | | 493/495/497 |
| 69 | 2 | Rac | 2-{[({1-{[2-(2,6-dichlorophenyl)-6-quinolinyl]methyl}-2-methoxy-2-oxoethyl)amino]carbonyl}benzyl benzoate | | 613/615/617 |
| 70 | 2 | Rac | methyl 2-{[2-(acetyloxy)benzoyl]amino}-3-[2-(2,6-dichlorophenyl)-6-quinolinyl]propanoate | | 537/539/541 |
| 71 | 2 | Rac | 3-[2-(2,6-dichlorophenyl)-6-quinolinyl]-2-[(2-hydroxybenzoyl)amino]propanoic acid | | 481/483/485 |
| 72 | 2 | Rac | 2-[(2,6-dichlorobenzoyl)amino]-3-(2-methoxy-6-quinolinyl)propanoic acid | | 419/421/423 |
| 73 | 2 | Rac | 2-(benzoylamino)-3-(2-phenyl-6-quinolinyl)propanoic acid | | 397 |
| 74 | 2 | Rac | 2-[(2,6-dichlorobenzoyl)amino]-3-(2-phenyl-6-quinolinyl)propanoic acid | | 465/467/469 |
| 75 | 2 | Rac | methyl 2-[(2,6-dichlorobenzoyl)amino]-3-[2-(1,3-thiazol-2-yl)-6-quinolinyl]propanoate | | 486/488/490 |
| 76 | 2 | Rac | 2-[(2,6-dichlorobenzoyl)amino]-3-[2-(4-pyridinyl)-6-quinolinyl]propanoic acid | | 466/468/470 |
| 77 | 2 | Rac | 2-[(2,6-dichlorobenzoyl)amino]-3-[2-(1,3-thiazol-2-yl)-6-quinolinyl]propanoic acid | | 472/474/476 |
| 78 | 2 | Rac | 2-[(2,6-dichlorobenzoyl)amino]-3-[2-(3,5-dichloro-4-pyridinyl)-6-quinolinyl]propanoic acid | | 534/536 |
| 79 | 2 | Rac | methyl 2-[(2,6-dichlorobenzoyl)amino]-3-[2-(3,5-dichloro-4-pyridinyl)-6-quinolinyl]propanoate | | 548/550/552 |
| 80 | 2 | Rac | 3-[2-(2,6-dichlorophenyl)-6-quinolinyl]-2-[(2,6-difluorobenzoyl)amino]propanoic acid | | 501/503/505 |
| 81 | 2 | Rac | 2-[(2,6-dichlorobenzoyl)amino]-3-(2-phenoxy-6-quinolinyl)propanoic acid | | 481/483/485 |
| 82 | 2S, 4R | Pure | methyl (2S)-2-({[(4R)-3-acetyl-1,3-thiazolidin-4-yl]carbonyl}amino)-3-[2-(2,6-dimethoxyphenyl)-6-quinolinyl]propanoate | −15.96 ($CH_3OH$, 1%) | 524 |
| 83 | 2S | Pure | methyl (2S)-2-{[2-chloro-4-(methylsulfonyl)benzoyl]amino}-3-[2-(2,6-dichlorophenyl)-6-quinolinyl]propanoate | −57.25 ($CH_3CN$, 1%) | 591/593/595 |
| 84 | 1R, 3S, 1 | Mixt | (1R,3S)-3-{[(1-{[2-(2,6-dichlorophenyl)-6-quinolinyl]methyl}-2-methoxy-2-oxoethyl)amino]carbonyl}-1,2,2-trimethylcyclopentanecarboxylic acid | | 557/559/561 |
| 85 | 2S | Pure | (2S)-2-[(2-chloro-6-methylbenzoyl)amino]-3-[2-(2,6-dichlorophenyl)-6-quinolinyl]propanoic acid | −68.63 ($CH_3CN$, 1%) | 513/515/517 |
| 86 | 2S | Pure | (2S)-2-{[2-chloro-4-(methylsulfonyl)benzoyl]amino}-3-[2-(2,6-dichlorophenyl)-6-quinolinyl]propanoic acid | −50.32 ($CH_3CN$, 1%) | 577/579/581 |
| 87 | 2 | Rac | 2-({[(2,6-dichlorophenyl)amino]carbonyl}amino)-3-[2-(2,6-dichlorophenyl)-6-quinolinyl]propanoic acid | | 548/550/552 |
| 88 | 2R (90%) 2S (10%) | Mtxt | (2R)-2-({[1-(4-chlorophenyl)cyclopentyl]carbonyl}amino)-3-[2-(2,6-dichlorophenyl)-6-quinolinyl]propanoic acid (90%) (2S)-2-({[1-(4-chlorophenyl)cyclopentyl]carbonyl}amino)-3-[2-(2,6-dichlorophenyl)-6-quinolinyl]propanoic acid (10%) | ee: 82% | 567/569/571 |
| 89 | 2S | Pure | (2S)-2-({[1-(4-chlorophenyl)cyclopentyl]carbonyl}amino)-3-[2-(2,6-dichlorophenyl)-6-quinolinyl]propanoic acid | ee: 98% | 567/569/571 |
| 90 | 2, 2S | Mixt | 3-[2-(2,6-dichlorophenyl)-6-quinolinyl]-2-[({(2S)-1-[(4-methylphenyl)sulfonyl]piperidinyl}carbonyl)amino]propanoic acid | | 626/628/630 |
| 91 | 2 | Rac | 2-[(2,6-dichlorobenzyl)oxy]-3-[2-(2,6-dichlorophenyl)-6-quinolinyl]propanoic acid | | 521 |
| 92 | 1R, 3S, 1 | Mixt | (1R,3S)-3-[({1-carboxy-2-[2-(2,6-dichlorophenyl)-6-quinolinyl]ethyl}amino)carbonyl]-1,2,2-trimethylcyclopentanecarboxylic acid | | 543/545/547 |

TABLE 8-continued

| n° | Configuration data | | IUPAC Name | α_D (25° C.) or ee | LC-MS (MH+) |
|---|---|---|---|---|---|
| 93 | 2 | Rac | 2-[(2,6-dichlorobenzoyl)oxy]-3-[2-(2,6-dichlorophenyl)-6-quinolinyl]propanoic acid | | 534 |
| 94 | 2S | Pure | (2S)-2-[(2,6-difluorobenzoyl)amino]-3-[2-(2-nitrophenyl)-6-quinolinyl]propanoic acid | ee: >95% | 478 |
| 95 | 2S | Pure | (2S)-2-[(2,6-difluorobenzoyl)amino]-3-{2-[2-(trifluoromethyl)phenyl]-6-quinolinyl}propanoic acid | ee: >95% | 501 |
| 96 | 2S | Pure | (2S)-3-[2-(2-chloro-6-fluorophenyl)-6-quinolinyl]-2-[(2,6-difluorobenzoyl)amino]propanoic acid | ee: >95% | 485 |
| 97 | 2S | Pure | (2S)-2-[(2,6-difluorobenzoyl)amino]-3-[2-(2-methoxy-1-naphthyl)-6-quinolinyl]propanoic acid | ee: >95% | 513 |
| 98 | 2S | Pure | (2S)-2-[(2,6-dichlorobenzoyl)amino]-3-[2-(2-nitrophenyl)-6-quinolinyl]propanoic acid | ee: >95% | 510 |
| 99 | 2S | Pure | (2S)-2-[(2,6-dichlorobenzoyl)amino]-3-{2-[2-(trifluoromethyl)phenyl]-6-quinolinyl}propanoic acid | ee: >95% | 533 |
| 100 | 2S | Pure | (2S)-3-[2-(2-chloro-6-fluorophenyl)-6-quinolinyl]-2-[(2,6-dichlorobenzoyl)amino]propanoic acid | ee: >95% | 517 |
| 101 | 2S | Pure | (2S)-2-[(2,6-dichlorobenzoyl)amino]-3-[2-(2-methoxy-1-naphthyl)-6-quinolinyl]propanoic acid | ee: >95% | 545 |
| 102 | 2S | Pure | (2S)-2-[(2-chloro-6-methylbenzoyl)amino]-3-[2-(2-nitrophenyl)-6-quinolinyl]propanoic acid | ee: >95% | 490 |
| 103 | 2S | Pure | (2S)-2-[(2-chloro-6-methylbenzoyl)amino]-3-{2-[2-(trifluoromethyl)phenyl]-6-quinolinyl}propanoic acid | ee: >95% | 513 |
| 104 | 2S | Pure | (2S)-3-[2-(2-chloro-6-fluorophenyl)-6-quinolinyl]-2-[(2-chloro-6-methylbenzoyl)amino]propanoic acid | ee: >95% | 497 |
| 105 | 2S | Pure | (2S)-2-[(2-chloro-6-methylbenzoyl)amino]-3-[2-(2-methoxy-1-naphthyl)-6-quinolinyl]propanoic acid | ee: >95% | 525 |
| 106 | 2S | Pure | (2S)-2-{[2-chloro-4-(methylsulfonyl)benzoyl]amino}-3-{2-[2-nitrophenyl]-6-quinolinyl}propanoic acid | ee: >95% | 554 |
| 107 | 2S | Pure | (2S)-2-{[2-chloro-4-(methylsulfonyl)benzoyl]amino}-3-{2-[2-(trifluoromethyl)phenyl]-6-quinolinyl}propanoic acid | ee: >95% | 577 |
| 108 | 2S | Pure | (2S)-3-[2-(2-chloro-6-fluorophenyl)-6-quinolinyl]-2-{[2-chloro-4-(methylsulfonyl)benzoyl]amino}propanoic acid | ee: >95% | 561 |
| 109 | 2S | Pure | (2S)-2-{[2-chloro-4-(methylsulfonyl)benzoyl]amino}-3-[2-(2-methoxy-1-naphthyl)-6-quinolinyl]propanoic acid | ee: >95% | 589 |
| 110 | 2S, 4R | Pure | (2S)-2-({[(4R)-3-acetyl-1,3-thiazolidin-4-yl]carbonyl}amino)-3-[2-(2,6-dimethoxyphenyl)-6-quinolinyl]propanoic acid | ee: >98% | 510 |
| 111 | 2, 2S, 3aS, 7aS | Mixt | 2-[({(2S,3aS,7aS)-1-[(4-methylphenyl)sulfonyl]octahydro-1H-indol-2-yl}carbonyl)amino]-3-[2-(2,6-dichlorophenyl)-6-quinolinyl]propanoic acid | | 666/668/670 |
| 112 | 2S, 2S | Pure | methyl (2S)-3-[2-(2,6-dichlorophenyl)-6-quinolinyl]-2-({[(2S)-2-methyltetrahydro-2-furanyl]carbonyl}amino)propanoate | −3.54 (DMSO, 1%) | 487/489/491 |
| 113 | 2S, 2R | Pure | methyl (2S)-3-[2-(2,6-dichlorophenyl)-6-quinolinyl]-2-({[(2R)-2-methyltetrahydro-2-furanyl]carbonyl}amino)propanoate | −13.7 (DMSO, 1%) | 487/489/491 |
| 114 | 2S, 2S | Pure | (2S)-3-[2-(2,6-dichlorophenyl)-6-quinolinyl]-2-({[(2S)-2-methyltetrahydro-2-furanyl]carbonyl}amino)propanoic acid | +13.54 (DMSO, 1%) | 473/475/477 |
| 115 | 2S, 2R | Pure | (2S)-3-[2-(2,6-dichlorophenyl)-6-quinolinyl]-2-({[(2R)-2-methyltetrahydro-2-furanyl]carbonyl}amino)propanoic acid | +5.77 (DMSO, 1%) | 473/475/477 |
| 116 | 2 | Rac | methyl 3-[2-(2,6-dichlorophenyl)-6-quinolinyl]-2-[(2-isopropoxy-3,4-dioxo-1-cyclobuten-1-yl)amino]propanoate | | 513/515/517 |
| 117 | 1 | Rac | 2,6-dichloro-N-(1-{[2-(2,6-dichlorophenyl)-6-quinolinyl]methyl}-2-{[2-(4-morpholinyl)ethyl]amino}-2-oxoethyl)benzamide | | 645/647/649 |
| 118 | 1 | Rac | 2,6-dichloro-N-(1-{[2-(2,6-dichlorophenyl)-6-quinolinyl]methyl}-2-oxo-2-{[2-(1-pyrrolidinyl)ethyl]amino}ethyl)benzamide | | 629/631/633 |
| 119 | 1 | Rac | 2,6-dichloro-N-(1-{[2-(2,6-dichlorophenyl)-6-quinolinyl]methyl}-2-{[2-(dimethylamino)ethyl]amino}-2-oxoethyl)benzamide | | 603/605/607 |
| 120 | 1 | Rac | 2,6-dichloro-N-[1-{[2-(2,6-dichlorophenyl)-6-quinolinyl]methyl}-2-(methylamino)-2-oxoethyl]benzamide | | 546/548/550 |
| 121 | 1 | Rac | 2,6-dichloro-N-[1-{[2-(2,6-dichlorophenyl)-6-quinolinyl]methyl}-2-(hydroxyamino)-2-oxoethyl]benzamide | | 548/550/552 |
| 122 | 1 | Rac | N-(2-amino-1-{[2-(2,6-dichlorophenyl)-6-quinolinyl]methyl}-2-oxoethyl)-2,6-dichlorobenzamide | | 532/534/536 |
| 123 | 2 | Rac | methyl 3-[2-(2,6-dichlorophenyl)-6-quinolinyl]-2-{[3,4-dioxo-2-(propylamino)-1-cyclobuten-1-yl]amino}propanoate | | 513/515/517 |
| 124 | 2S, 2S | Pure | methyl (2S)-3-[2-(2,6-dichlorophenyl)-6-quinolinyl]-2-({[(2S)-1-(methylsulfonyl)piperidinyl]carbonyl}amino)propanoate | −1.55 (CH₂Cl₂, 1%) | 564/566/568 |
| 125 | 2S, 2S | Pure | (2S)-3-[2-(2,6-dichlorophenyl)-6-quinolinyl]-2-({[(2S)-1-(methylsulfonyl)piperidinyl]carbonyl}amino)propanoic acid | +29.41 (CH₂Cl₂, 1%) | 550/552/554 |
| 126 | 1 | Rac | 2,6-dichloro-N-[2-[2-(2,6-dichlorophenyl)-6-quinolinyl]-1-(1H-tetraazol-5-yl)ethyl]benzamide | | 557/559/561 |
| 127 | 2 | Rac | methyl 2-{[(6-amino-3-pyridinyl)carbonyl]amino}-3-[2-(2,6-dichlorophenyl)-6-quinolinyl]propanoate | | 495/497/499 |
| 128 | 2 | Rac | methyl 2-[(2,6-dichlorobenzoyl)amino]-3-[2-(2-methoxyphenoxy)-6-quinolinyl]propanoate | | 525 |
| 129 | 2 | Rac | ({2-[(2,6-dichlorobenzoyl)amino]-3-[2-(2,6-dichlorophenyl)-6-quinolinyl]propanoyl}oxy)methyl pivalate | | 647/649/651 |

TABLE 8-continued

| n° | Configuration data | | IUPAC Name | α$_D$ (25° C.) or ee | LC-MS (MH+) |
|---|---|---|---|---|---|
| 130 | 2S, 4R | Pure | methyl (2S)-2-({[(4R)-3-acetyl-1,1-dioxido-1,3-thiazolidin-4-yl]carbonyl}amino)-3-[2-(2,6-dichlorophenyl)-6-quinolinyl]propanoate | +10.51 (CH$_3$OH, 1%) | 564/566/568 |
| 131 | ** | | 2-[({(2S,3aS,7aS)-1-[(4-methylphenyl)sulfonyl]octahydro-1H-indol-2-yl}carbonyl)amino]-3-[2-(2-chlorophenyl)-6-quinolinyl]propanoic acid | | 632 |
| 132 | ** | | 3-[2-(2,6-dichlorophenyl)-6-quinolinyl]-2-{[(2,6-dichlorophenyl)sulfonyl]amino}propanoic acid | | 458 |
| 133 | ** | | 3-[2-(3,4-dichlorophenyl)-6-quinolinyl]-2-{[(2,6-dichlorophenyl)sulfonyl]amino}propanoic acid | | 569 |
| 134 | ** | | 3-[2-(2-bromophenyl)-6-quinolinyl]-2-[(2,6-dichlorobenzoyl)amino]propanoic acid | | 543 |
| 135 | ** | | 3-[2-(2-bromophenyl)-6-quinolinyl]-2-[({(2S)-1-[(4-methylphenyl)sulfonyl]piperidinyl}carbonyl)amino]propanoic acid | | 636 |
| 136 | ** | | 2-[({(2S,3aS,7aS)-1-[(4-methylphenyl)sulfonyl]octahydro-1H-indol-2-yl}carbonyl)amino]-3-[2-(2-bromophenyl)-6-quinolinyl]propanoic acid | | 676 |
| 137 | ** | | 3-{2-[2-chloro-5-(trifluoromethyl)phenyl]-6-quinolinyl}-2-[(2,6-dichlorobenzyl)amino]propanoic acid | | 567 |
| 138 | ** | | 2-[(2-chloro-6-methylbenzoyl)amino]-3-{2-[2-chloro-5-(trifluoromethyl)phenyl]-6-quinolinyl}propanoic acid | | 547 |
| 139 | ** | | 2-{[2-chloro-4-(methylsulfonyl)benzoyl]amino}-3-{2-[2-chloro-5-(trifluoromethyl)phenyl]-6-quinolinyl}propanoic acid | | 611 |
| 140 | ** | | 3-{2-[2-chloro-5-(trifluoromethyl)phenyl]-6-quinolinyl}-2-[({(2S)-1-[(4-methylphenyl)sulfonyl]piperidinyl}carbonyl)amino]propanoic acid | | 660 |
| 141 | ** | | 2-[({(2S,3aS,7aS)-1-[(4-methylphenyl)sulfonyl]octahydro-1H-indol-2-yl}carbonyl)amino]-3-{2-[2-chloro-5-(trifluoromethyl)phenyl]-6-quinolinyl}propanoic acid | | 700 |
| 142 | ** | | 3-(2-cyclohexyl-6-quinolinyl)-2-[(2,6-dichlorobenzoyl)amino]propanoic acid | | 471 |
| 143 | ** | | 2-({[1-(4-chlorophenyl)cyclopentyl]carbonyl}amino)-3-(2-cyclohexyl-6-quinolinyl)propanoic acid | | 505 |
| 144 | ** | | 2-({[1-(4-chlorophenyl)cyclopentyl]carbonyl}amino)-3-[2-(2-nitrophenyl)-6-quinolinyl]propanoic acid | | 544 |
| 145 | ** | | 3-(2-cyclohexyl-6-quinolinyl)-2-[(2,6-dimethoxybenzoyl)amino]propanoic acid | | 463 |
| 146 | ** | | 2-[(2,6-dimethoxybenzoyl)amino]-3-[2-(2-nitrophenyl)-6-quinolinyl]propanoic acid | | 502 |
| 147 | ** | | 2-[(2-chloro-6-methylbenzoyl)amino]-3-(2-cyclohexyl-6-quinolinyl)propanoic acid | | 451 |
| 148 | ** | | 3-{2-[2-(1,3-benzodioxol-5-yl)-1-methylethyl]-6-quinolinyl}-2-[(2-chloro-6-methylbenzoyl)amino]propanoic acid | | 531 |
| 149 | ** | | 3-(2-bicyclo[2.2.1]hept-5-en-2-yl-6-quinolinyl)-2-{[2-chloro-4-(methylsulfonyl)benzoyl]amino}propanoic acid | | 525 |
| 150 | ** | | 2-{[2-chloro-4-(methylsulfonyl)benzoyl]amino}-3-[2-(1-phenylethyl)-6-quinolinyl]propanoic acid | | 537 |
| 151 | ** | | 3-{2-[2-(1,3-benzodioxol-5-yl)-1-methylethyl]-6-quinolinyl}-2-{[2-chloro-4-(methylsulfonyl)benzoyl]amino}propanoic acid | | 595 |
| 152 | ** | | 2-({[1-(4-chlorophenyl)cyclopentyl]carbonyl}amino)-3-[2-(2-methoxyphenyl)-6-quinolinyl]propanoic acid | | 529 |
| 153 | ** | | 2-({[1-(4-chlorophenyl)cyclopentyl]carbonyl}amino)-3-[2-(2-6-dimethoxyphenyl)-6-quinolinyl]propanoic acid | | 559 |
| 154 | ** | | 2-[(2,6-difluorobenzoyl)amino]-3-[2-(2,6-dimethoxyphenyl)-6-quinolinyl]propanoic acid | | 493 |
| 155 | ** | | 2-[(2-chloro-6-methylbenzoyl)amino]-3-[2-(2-methoxyphenyl)-6-quinolinyl]propanoic acid | | 475 |
| 156 | ** | | 2-[(2-chloro-6-methylbenzoyl)amino]-3-[2-(2,3-dimethoxyphenyl)-6-quinolinyl]propanoic acid | | 505 |
| 157 | ** | | 2-{[2-chloro-4-(methylsulfonyl)benzoyl]amino}-3-[2-(2-methoxyphenyl)-6-quinolinyl]propanoic acid | | 539 |
| 158 | ** | | 2-{[2-chloro-4-(methylsulfonyl)benzoyl]amino}-3-[2-(2,3-dimethoxyphenyl)-6-quinolinyl]propanoic acid | | 569 |
| 159 | ** | | 2-{[2-chloro-4-(methylsulfonyl)benzoyl]amino}-3-[2-(2,6-dimethoxyphenyl)-6-quinolinyl]propanoic acid | | 569 |
| 160 | ** | | 2-{[(1-acetyl-2-pyrrolidinyl)carbonyl]amino}-3-[2-(2,6-dimethoxyphenyl)-6-quinolinyl]propanoic acid | | 492 |
| 161 | ** | | 2-[(2,6-dichlorobenzoyl)amino]-3-[2-(2,4-dichlorophenyl)-6-quinolinyl]propanoic acid | | 533 |
| 162 | ** | | 2-[(2,6-dichlorobenzoyl)amino]-3-{2-[4-(methylsulfonyl)phenyl]-6-quinolinyl}propanoic acid | | 543 |
| 163 | ** | | 3-[2-(2-chloro-6-fluorophenyl)-6-quinolinyl]-2-({[1-(4-chlorophenyl)cyclopentyl]carbonyl}amino)propanoic acid | | 551 |
| 164 | ** | | 2-({[1-(4-chlorophenyl)cyclopentyl]carbonyl}amino)-3-{2-[2-(trifluoromethyl)phenyl]-6-quinolinyl}propanoic acid | | 567 |
| 165 | ** | | 2-({[1-(4-chlorophenyl)cyclopentyl]carbonyl}amino)-3-{2-[4-(methylsulfonyl)phenyl]-6-quinolinyl}propanoic acid | | 577 |
| 166 | ** | | 3-[2-(2,4-dichlorophenyl)-6-quinolinyl]-2-[(2,6-dimethoxybenzoyl)amino]propanoic acid | | 525 |

TABLE 8-continued

| n° | Configuration data | | IUPAC Name | α_D (25° C.) or ee | LC-MS (MH+) |
|---|---|---|---|---|---|
| 167 | ** | | 3-[2-(2-chloro-6-fluorophenyl)-6-quinolinyl]-2-[(2,6-dimethoxybenzoyl)amino]propanoic acid | | 509 |
| 168 | ** | | 2-[(2,6-dimethoxybenzoyl)amino]-3-{2-[2-(trifluoromethyl)phenyl]-6-quinolinyl}propanoic acid | | 525 |
| 169 | ** | | 2-[(2,6-difluorobenzoyl)amino]-3-{2-[4-(methylsulfonyl)phenyl]-6-quinolinyl}propanoic acid | | 511 |
| 170 | ** | | 2-[(2-chloro-6-methylbenzoyl)amino]-3-(2-mesityl-6-quinolinyl)propanoic acid | | 487 |
| 171 | ** | | 2-[(2-chloro-6-methylbenzoyl)amino]-3-[2-(2,4-dichlorophenyl)-6-quinolinyl]propanoic acid | | 513 |
| 172 | ** | | 2-{[2-chloro-4-(methylsulfonyl)benzoyl]amino}-3-(2-mesityl-6-quinolinyl)propanoic acid | | 551 |
| 173 | ** | | 2-{[2-chloro-4-(methylsulfonyl)benzoyl]amino}-3-[2-(2,4-dichlorophenyl)-6-quinolinyl]propanoic acid | | 577 |
| 174 | ** | | 2-{[(1-acetyl-2-pyrrolidinyl)carbonyl]amino}-3-[2-(2,4-dichlorophenyl)-6-quinolinyl]propanoic acid | | 500 |
| 175 | ** | | 2-{[(1-acetyl-2-pyrrolidinyl)carbonyl]amino}-3-[2-(2-chloro-6-fluorophenyl)-6-quinolinyl]propanoic acid | | 484 |
| 176 | ** | | 3-{2-[5-chloro-1-methyl-3-(trifluoromethyl)-1H-pyrazol-4-yl]-6-quinolinyl}-2-[(2,6-dichlorobenzoyl)amino]propanoic acid | | 571 |
| 177 | 2S | Pure | (2S)-2-[(2,6-dichlorobenzoyl)amino]-3-[2-(2,6-dimethylphenyl)-6-quinolinyl]propanoic acid | | 493 |
| 178 | ** | | 2-({[1-(4-chlorophenyl)cyclopentyl]carbonyl}amino)-3-[2-(2,3-difluorophenyl)-6-quinolinyl]propanoic acid | | 605 |
| 179 | ** | | 2-({[1-(4-chlorophenyl)cyclopentyl]carbonyl}amino)-3-[2-(2-methoxy-1-naphthyl)-6-quinolinyl]propanoic acid | | 579 |
| 180 | ** | | 2-({[1-(4-chlorophenyl)cyclopentyl]carbonyl}amino)-3-[2-(2,6-dimethylphenyl)-6-quinolinyl]propanoic acid | | 527 |
| 181 | ** | | 2-[(2,6-dimethoxybenzoyl)amino]-3-[2-(2-methoxy-1-naphthyl)-6-quinolinyl]propanoic acid | | 537 |
| 182 | ** | | 2-[(2-chloro-6-methylbenzoyl)amino]-3-{2-[5-chloro-1-methyl-3-(trifluoromethyl)-1H-pyrazol-4-yl]-6-quinolinyl}propanoic acid | | 551 |
| 183 | ** | | 2-[(2-chloro-6-methylbenzoyl)amino]-3-[2-(2,6-dimethylphenyl)-6-quinolinyl]propanoic acid | | 473 |
| 184 | ** | | 2-{[2-chloro-4-(methylsulfonyl)benzoyl]amino}-3-{2-[5-chloro-1-methyl-3-(trifluoromethyl)-1H-pyrazol-4-yl]-6-quinolinyl}propanoic acid | | 615 |
| 185 | 2S | Pure | (2S)-2-{[2-chloro-4-(methylsulfonyl)benzoyl]amino}-3-[2-(2,6-dimethylphenyl)-6-quinolinyl]propanoic acid | | 537 |
| 186 | ** | | 2-{[(1-acetyl-2-pyrrolidinyl)carbonyl]amino}-3-[2-(2-methoxy-1-naphthyl)-6-quinolinyl]propanoic acid | | 512 |
| 190 | ** | | 2-[(2,6-dichlorobenzoyl)amino]-3-[2-(2-pyrrolidinyl)-6-quinolinyl]propanoic acid | | 451 |
| 191 | ** | | 2-[(2,6-dichlorobenzoyl)amino]-3-[2-(2,6-difluorophenyl)-6-quinolinyl]propanoic acid | | 501 |
| 192 | ** | | 3-[2-(2-chloro-6-nitrophenyl)-6-quinolinyl]-2-[(2,6-dichlorobenzoyl)amino]propanoic acid | | 544 |
| 193 | ** | | 2-({[1-(4-chlorophenyl)cyclopentyl]carbonyl}amino)-3-[2-(2,6-difluorophenyl)-6-quinolinyl]propanoic acid | | 535 |
| 194 | ** | | 3-[2-(2-chloro-6-nitrophenyl)-6-quinolinyl]-2-[(2,6-dimethoxybenzoyl)amino]propanoic acid | | 536 |
| 195 | ** | | 2-[(2-chloro-6-methylbenzoyl)amino]-3-[2-(2,6-difluorophenyl)-6-quinolinyl]propanoic acid | | 481 |
| 196 | ** | | 2-[(2-chloro-6-methylbenzoyl)amino]-3-[2-(2-chloro-6-nitrophenyl)-6-quinolinyl]propanoic acid | | 524 |
| 197 | 2 | Rac | 3-[2-(4-chlorophenoxy)-6-quinolinyl]-2-[(2,6-dichlorobenzoyl)amino]propanoic acid | | 515/517/519 |
| 198 | 2 | Rac | 3-[2-(2,6-dichlorophenyl)-6-quinolinyl]-2-{[3,4-dioxo-2-(propylamino)-1-cyclobuten-1-yl]amino}propanoic acid | | 498/500/502 |
| 199 | 2 | Rac | methyl 2-amino-3-(2-phenyl-6-quinolinyl)propanoate | | 479 |
| 208 | 2 | Rac | 2-amino-3-[6-(2,6-dimethoxyphenyl)-2-naphthyl]propanoic acid hydrochloride | | 352 |
| 209 | 2 | Rac | methyl 2-[(2,6-dichlorobenzoyl)amino]-3-[6-(2,6-dimethoxyphenyl)-2-naphthyl]propanoate | | 538/540/542 |
| 210 | 2 | Rac | 2-[(2,6-dichlorobenzoyl)amino]-3-[6-(2,6-dimethoxyphenyl)-2-naphthyl]propanoic acid | | 524/526/528 |
| 211 | 2 | Rac | 2-amino-3-[6-(2,6-dichlorophenyl)-2-naphthyl]propanoic acid hydrochloride | | 396 |
| 212 | 2 | Rac | methyl 2-amino-3-[6-(2,6-dichlorophenyl)-2-naphthyl]propanoate hydrochloride | | 410 |
| 213 | 2 | Rac | methyl 2-[(2,6-dichlorobenzoyl)amino]-3-[6-(2,6-dichlorophenyl)-2-naphthyl]propanoate | | 548 |
| 214 | 2 | Rac | 2-[(2,6-dichlorobenzoyl)amino]-3-[6-(2,6-dichlorophenyl)-2-naphthyl]propanoic acid | | 532/534/536 |
| 215 | A-2§ | Pure | (−)-methyl 2-[(2,6-dichlorobenzoyl)amino]-3-[6-(2,6-dimethoxyphenyl)-2-naphthyl]propanoate | −34.60 (DMSO, 1%) | 538/540/542 |

TABLE 8-continued

| n° | Configuration data | | IUPAC Name | α_D (25° C.) or ee | LC-MS (MH+) |
|---|---|---|---|---|---|
| 216 | B-2§ | Pure | (+)-methyl 2-[(2,6-dichlorobenzoyl)amino]-3-[6-(2,6-dimethoxyphenyl)-2-naphthyl]propanoate | +33.88 (DMSO, 1%) | 538/540/542 |
| 217 | A-2§ | Pure | (−)-2-[(2,6-dichlorobenzoyl)amino]-3-[6-(2,6-dimethoxyphenyl)-2-naphthyl]propanoic acid | −23.95 (DMSO, 1%) | 524/526/528 |
| 218 | B-2§ | Pure | (+)-2-[(2,6-dichlorobenzoyl)amino]-3-[6-(2,6-dimethoxyphenyl)-2-naphthyl]propanoic acid | +26.10 (DMSO, 1%) | 524/526/528 |
| 219 | 2, 2S | Mixt | 3-[6-(2,6-dimethoxyphenyl)-2-naphthyl]-2-({[(2S)-1-(phenylsulfonyl)pyrrolidinyl]carbonyl}amino)propanoic acid | | 589 |
| 220 | 2, 2S | Mixt | methyl 3-[6-(2,6-dimethoxyphenyl)-2-naphthyl]-2-({[(2S)-1-(phenylsulfonyl)pyrrolidinyl]carbonyl}amino)propanoate | | 603 |
| 221 | 2, 2S | Mixt | methyl 3-[6-(2,6-dimethoxyphenyl)-2-naphthyl]-2-({[(2S)-1-methylpyrrolidinyl]carbonyl}amino)propanoate | | 477 |
| 222 | 2S | Pure | methyl (2S)-2-{[(2,4-dichloro-6-methyl-3-pyridinyl)carbonyl]amino}-3-[2-(2,6-dichlorophenyl)-6-quinolinyl]propanoate | ee: 93% | 562/564/566 |
| 223 | 1R, 3S, 1S | Pure | (1R,3S)-3-{[((1S)-1-{[2-(2,6-dichlorophenyl)-6-quinolinyl]methyl}-2-methoxy-2-oxoethyl)amino]carbonyl}-1,2,2-trimethylcyclopentanecarboxylic acid | −3.89 (CH₃CN, 1%) | 557/559/561 |
| 224 | 2 | Rac | 2-{[(6-amino-3-pyridinyl)carbonyl]amino}-3-[2-(2,6-dichlorophenyl)-6-quinolinyl]propanoic acid | | 481/483/485 |
| 225 | 2S | Pure | methyl (2S)-2-{[(2-amino-3-pyridinyl)carbonyl]amino}-3-[2-(2,6-dichlorophenyl)-6-quinolinyl]propanoate | ee: 93% | 495/497/499 |
| 226 | 2S | Pure | (2S)-2-{[(2-amino-3-pyridinyl)carbonyl]amino}-3-[2-(2,6-dichlorophenyl)-6-quinolinyl]propanoic acid | −36.89 (DMSO, 1%) | 481/483/485 |
| 227 | 2 | Rac | 2-[(2,6-dichlorobenzoyl)amino]-3-[2-(2-methoxyphenoxy)-6-quinolinyl]propanoic acid | | 511/513/515 |
| 228 | 2 | Rac | methyl 2-[(2,6-dichlorobenzoyl)amino]-3-[2-(2,6-dimethoxyphenyl)-6-quinolinyl]propanoate | | 539/541/543 |
| 229 | 3S, 1R, 1S | Pure | (1R,3S)-3-[({(1S)-1-carboxy-2-[2-(2,6-dichlorophenyl)-6-quinolinyl]ethyl}amino)carbonyl]-1,2,2-trimethylcyclopentanecarboxylic acid | +31.54 (THF, 1%) | 543/545/547 |
| 230 | 2S, 4R | Pure | (2S)-2-({[(4R)-3-acetyl-1,1-dioxido-1,3-thiazolidin-4-yl]carbonyl}amino)-3-[2-(2,6-dichlorophenyl)-6-quinolinyl]propanoic acid | +34.67 (CH₃OH, 1%) | 550/552/554 |
| 231 | 2S | Pure | methyl (2S)-3-[2-(2,6-dichlorophenyl)-6-quinolinyl]-2-{[2-(1-piperidinyl)benzoyl]amino}propanoate | +37.73 (CH₃OH, 1%) | 562/564/566 |
| 232 | 2S, 3 | Mixt | methyl (2S)-3-[2-(2,6-dichlorophenyl)-6-quinolinyl]-2-[(4-{[(1,1-dioxidotetrahydro-3-thienyl)amino]methyl}benzoyl)amino]propanoate | | 626/628/630 |
| 233 | 2S | Pure | (2S)-2-{[(2,4-dichloro-6-methyl-3-pyidinyl)carbonyl]amino}-3-[2-(2,6-dichlorophenyl)-6-quinolinyl]propanoic acid | −62.43 (CH₃OH, 1%) | 548/550/552/554 |
| 234 | 2S | Pure | methyl (2S)-2-{[(2-chloro-3-pyridinyl)carbonyl]amino}-3-[2-(2,6-dichlorophenyl)-6-quinolinyl]propanoate | +39.33 (CH₂Cl₂, 1%) | 514/516/518/520 |
| 235 | 2S | Pure | (2S)-3-[2-(2,6-dichlorophenyl)-6-quinolinyl]-2-{[2-(1-piperidinyl)benzoyl]amino}propanoic acid | +30.44 (DMSO, 1%) | 548/550/552 |
| 236 | 2S, 3 | Mixt | (2S)-3-[2-(2,6-dichlorophenyl)-6-quinolinyl]-2-[(4-{[(1,1-dioxidotetrahydro-3-thienyl)amino]methyl}benzoyl)amino]propanoic acid | | 612/614/616 |
| 237 | 2 | Rac | methyl 2-[(2,6-dichlorobenzoyl)amino]-3-[2-(2,6-dimethoxyphenoxy)-6-quinolinyl]propanoate | | 555 |
| 238 | 2 | Rac | 2-[(2,6-dichlorobenzoyl)amino]-3-[2-(2,6-dimethoxyphenoxy)-6-quinolinyl]propanoic acid | | 541/543 |
| 239 | 2 | Rac | methyl 2-[(2,6-dichlorobenzoyl)amino]-3-[2-(2,6-dichlorophenoxy)-6-quinolinyl]propanoate | | 563 |
| 240 | 2S | Pure | (2S)-2-{[(2-chloro-3-pyridinyl)carbonyl]amino}-3-[2-(2,6-dichlorophenyl)-6-quinolinyl]propanoic acid | −39.16 (CH₃OH, 1%) | 500/502/504 |
| 241 | 2S | Pure | methyl (2S)-2-[(2,6-dichlorobenzoyl)amino]-3-[2-(2,6-dimethoxyphenyl)-6-quinolinyl]propanoate | +16.37 (CH₂Cl₂, 1%) | 539/541/543 |
| 242 | 2R | Pure | methyl (2R)-2-[(2,6-dichlorobenzoyl)amino]-3-[2-(2,6-dimethoxyphenyl)-6-quinolinyl]propanoate | −17.04 (CH₂Cl₂, 1%) | 539/541/543 |
| 243 | 2S | Pure | methyl (2S)-2-[(2,6-dichlorobenzoyl)amino]-3-[2-(2,6-dimethylphenyl)-6-quinolinyl]propanoate | +3.00 (CH₂Cl₂, 1%) | 507/509/511 |
| 244 | 2S | Pure | (2S)-2-[(2,6-dichlorobenzoyl)amino]-3-[2-(2,6-dimethoxyphenyl)-6-quinolinyl]propanoic acid | −32.15 (DMSO, 1%) | 525/527/529 |
| 245 | 2R | Pure | (2R)-2-[(2,6-dichlorobenzoyl)amino]-3-[2-(2,6-dimethoxyphenyl)-6-quinolinyl]propanoic acid | +31.40 (DMSO, 1%) | 525/527/529 |
| 246 | 2R, 2S | Pure | methyl (2R)-3-[2-(2,6-dimethoxyphenyl)-6-quinolinyl]-2-({[(2S)-2-methyltetrahydro-2-furanyl]carbonyl}amino)propanoate | −29.51 (CH₂Cl₂, 1%) | 479 |
| 247 | 2S, 2R | Pure | methyl (2S)-3-[2-(2,6-dimethoxyphenyl)-6-quinolinyl]-2-({[(2R)-2-methyltetrahydro-2-furanyl]carbonyl}amino)propanoate | +31.59 (CH₂Cl₂, 1%) | 479 |
| 248 | 2S, 2S | Pure | methyl (2S)-3-[2-(2,6-dimethoxyphenyl)-6-quinolinyl]-2-({[(2S)-2-methyltetrahydro-2-furanyl]carbonyl}amino)propanoate | +32.42 (CH₂Cl₂, 1%) | 479 |
| 249 | 2R, 2R | Pure | methyl (2R)-3-[2-(2,6-dimethoxyphenyl)-6-quinolinyl]-2-({[(2R)-2-methyltetrahydro-2-furanyl]carbonyl}amino)propanoate | −33.11 (CH₂Cl₂, 1%) | 479 |
| 250 | 2R, 2S | Pure | (2R)-3-[2-(2,6-dimethoxyphenyl)-6-quinolinyl]-2-({[(2S)-2-methyltetrahydro-2-furanyl]carbonyl}amino)propanoic acid | −63.77 (CH₂Cl₂, 1%) | 465 |
| 251 | 2S, 2R | Pure | (2S)-3-[2-(2,6-dimethoxyphenyl)-6-quinolinyl]-2-({[(2R)-2-methyltetrahydro-2-furanyl]carbonyl}amino)propanoic acid | +65.72 (CH2Cl2, 1%) | 465 |

TABLE 8-continued

| n° | Configuration data | | IUPAC Name | α_D (25° C.) or ee | LC-MS (MH+) |
|---|---|---|---|---|---|
| 252 | 2S, 2S | Pure | (2S)-3-[2-(2,6-dimethoxyphenyl)-6-quinolinyl]-2-({[(2S)-2-methyltetrahydro-2-furanyl]carbonyl}amino)propanoic acid | +51.10 (CH$_2$Cl$_2$, 1%) | 465 |
| 253 | 2R, 2R | Pure | (2R)-3-[2-(2,6-dimethoxyphenyl)-6-quinolinyl]-2-({[(2R)-2-methyltetrahydro-2-furanyl]carbonyl}amino)propanoic acid | −57.31 (CH$_2$Cl$_2$, 1%) | 465 |
| 254 | 2R, 4R | Pure | methyl (2R)-2-({[(4R)-3-acetyl-1,3-thiazolidin-4-yl]carbonyl}amino)-3-[2-(2,6-dimethoxyphenyl)-6-quinolinyl]propanoate | −20.52 (CH$_2$Cl$_2$, 1%) | 524 |
| 255 | 2R, 4R | Pure | (2R)-2-({[(4R)-3-acetyl-1,3-thiazolidin-4-yl]carbonyl}amino)-3-[2-(2,6-dimethoxyphenyl)-6-quinolinyl]propanoic acid | ee: 100% | 510 |
| 256 | 2 | Rac | 2-[(2,6-dichlorobenzoyl)amino]-3-[2-(2,6-dichlorophenoxy)-6-quinolinyl]propanoic acid | | 549/551/553 |
| 257 | 2 | Rac | methyl 3-[(2,6-dichlorophenyl)amino]-2-{[2-(2,6-dichlorophenyl)-6-quinolinyl]methyl}-3-oxopropanoate | | 547/549/551 |
| 258 | 2 | Rac | methyl 2-[({1-[(tert-butoxycarbonyl)amino]cyclopentyl}carbonyl)amino]-3-[2-(2,6-dichlorophenyl)-6-quinolinyl]propanoate | | 586/588/590 |
| 259 | 2 | Rac | methyl 2-{[(1-aminocyclopentyl)carbonyl]amino}-3-[2-(2,6-dichlorophenyl)-6-quinolinyl]propanoate | | 486/488/490 |
| 260 | 2 | Rac | 2-{[(1-aminocyclopentyl)carbonyl]amino}-3-[2-(2,6-dichlorophenyl)-6-quinolinyl]propanoic acid | | 472/474/476 |
| 261 | 1S | Pure | tert-butyl 4-(4-{[((1S)-1-{[2-(2,6-dichlorophenyl)-6-quinolinyl]methyl}-2-methoxy-2-oxoethyl)amino]carbonyl}benzyl)-1-piperidinecarboxylate | −74 (MeOH, 1%) | 676/678/680 |
| 262 | 2S | Pure | methyl (2S)-3-[2-(2,6-dichlorophenyl)-6-quinolinyl]-2-{[4-(4-piperidinylmethyl)benzoyl]amino}propanoate | | 576/578/580 |
| 263 | 2S | Pure | (2S)-3-[2-(2,6-dichlorophenyl)-6-quinolinyl]-2-{[4-(4-piperidinylmethyl)benzoyl]amino}propanoic acid | −20.46 (DMSO, 1%) | 562/564/566 |
| 264 | 2 | Rac | tert-butyl 2-[(2,6-dichlorobenzoyl)amino]-3-[2-(2,6-dichlorophenyl)-6-quinolinyl]propanoate | | 589/591/593/595/597 |
| 265 | 2S | Pure | methyl (2S)-3-[2-(2,6-dichlorophenyl)-6-quinolinyl]-2-[(4,6-dimethoxy-1,3,5-triazin-2-yl)amino]propanoate | −3.93 (CH$_3$OH, 1%) | 514/516/518 |
| 266 | 2S | Pure | (2S)-3-[2-(2,6-dichlorophenyl)-6-quinolinyl]-2-{[3-(4-piperidinyl)benzoyl]amino}propanoic acid | −7.93 (DMSO, 1%) | 548/550/552 |
| 267 | 2S | Pure | (2S)-3-[2-(2,6-dichlorophenyl)-6-quinolinyl]-2-[(4,6-dimethoxy-1,3,5-triazin-2-yl)amino]propanoic acid | +67.53 (DMSO, 1%) | 500/502 |
| 268 | 2S | Pure | methyl (2S)-2-{[2-(4-chlorophenyl)-2-methylpropanoyl]amino}-3-[2-(2,6-dichlorophenyl)-6-quinolinyl]propanoate | ee: 93% | 555/557/559 |
| 269 | 2S (95%) 2R (5%) | Mixt | (2S)-2-{[2-(4-chlorophenyl)-2-methylpropanoyl]amino}-3-[2-(2,6-dichlorophenyl)-6-quinolinyl]propanoic acid (95%) (2R)-2-{[2-(4-chlorophenyl)-2-methylpropanoyl]amino}-3-[2-(2,6-dichlorophenyl)-6-quinolinyl]propanoic acid (5%) | ee: 90% | 541/543/545 |
| 270 | 2S (95%) 2R (5%) | Pure | (2S)-3-[2-(2,6-dichlorophenyl)-6-quinolinyl]-2-[(2-methyl-2-phenylpropanoyl)amino]propanoic acid (95%) (2R)-3-[2-(2,6-dichlorophenyl)-6-quinolinyl]-2-[(2-methyl-2-phenylpropanoyl)amino]propanoic acid (5%) | ee: 90% | 507/509/511 |
| 271 | 2S | Pure | methyl (2S)-3-[2-(2,6-dichlorophenyl)-6-quinolinyl]-2-[(2-methyl-2-phenylpropanoyl)amino]propanoate | ee: 94% | 521/523/525 |
| 272 | 2S | Pure | (2S)-3-[2-(2,6-dichlorophenyl)-6-quinolinyl]-2-[({1-[2-(diethylamino)ethyl]cyclopentyl}carbonyl)amino]propanoic acid | +26.81 (CH3OH, 1%) | 556/558/560 |
| 273 | 2S | Pure | (2S)-2-[(2,6-dichlorobenzoyl)amino]-3-[2-(3,5-dichloro-4-pyridinyl)-6-quinolinyl]propanoic acid | ee: 100% | 534/536 |
| 274 | 2S, 2R | Pure | (2S)-3-[2-(3,5-dichloro-4-pyridinyl)-6-quinolinyl]-2-({[(2R)-2-methyltetrahydro-2-furanyl]carbonyl}amino)propanoic acid | +17.58 (CH$_3$OH, 1%) | 474/476/478 |
| 275 | 2, 2S | Mixt | methyl 3-[2-(2,6-dichlorophenyl)-6-quinolinyl]-2-({[(2S)-1-(phenylsulfonyl)pyrrolidinyl]carbonyl}amino)propanoate | | 612/614/616 |
| 276 | 2S | Pure | methyl (2S)-2-({[1-(4-chlorophenyl)cyclopentyl]carbonyl}amino)-3-[2-(3,5-dichloro-4-pyridinyl)-6-quinolinyl]propanoate | −49.28 (DMSO, 1%) | 582/584/586 |
| 277 | 2S | Pure | (2S)-2-({[1-(4-chlorophenyl)cyclopentyl]carbonyl}amino)-3-[2-(3,5-dichloro-4-pyridinyl)-6-quinolinyl]propanoic acid | −43 (DMSO, 1%) | 568/570/572 |
| 278 | 2S, 2S | Pure | (2S)-2-({[(2S)-1-benzyl-5-oxopyrrolidinyl]carbonyl}amino)-3-[2-(2,6-dichlorophenyl)-6-quinolinyl]propanoic acid | +5.77 (CH$_3$OH, 1%) | 562/564/566 |
| 279 | 2, 2S | Mixt | 3-[2-(2,6-dichlorophenyl)-6-quinolinyl]-2-({[(2S)-1-(phenylsulfonyl)pyrrolidinyl]carbonyl}amino)propanoic acid | | 598/600/602 |
| 282 | 1 | Rac | 2,6-dichloro-N-{1-{[2-(2,6-dichlorophenyl)-6-quinolinyl]methyl}-2-[(methylsulfonyl)amino]-2-oxoethyl}benzamide | | 610/612/614 |

** compounds synthesised from the corresponding "L" amino acid. The stereochemistry was not determined; the carbon atom to which R$^2$ and R$^3$ are attached could be in the "S" or "R" configuration, with a proportion of 2S isomer comprised between 50% and 100%.

EXAMPLE 6

In Vitro Biological Assay. U937/VCAM-1 Adhesion Assay

Compounds of the invention are tested in a VLA-4 dependent adhesion test

The VLA-4 expressing cell line U937 (ATCC n°: CRL 1593) is cultured in RPMI 1640 medium supplemented with foetal bovine serum 10%. Prior to the assay cells are washed, resuspended in HBSS BSA 0.1% at 5×10$^6$ cells/ml and loaded with the fluorescent dye Calcein-AM at a final concentration of 10 µmol/l for 15 min at 37° C. After washing, cells are resuspended in RPMI at 2×10$^6$ cells/ml.

96 well microtiter plates are coated with 50 µl aliquots of soluble human recombinant VCAM-1 (2.5 µg/ml in DPBS) overnight at 4° C. DPBS alone is added to some wells for non specific adhesion measurement. Wells are washed to remove unbound protein and blocked by incubation with 1% BSA for 1 h at 37° C. to reduce background adherence.

Compounds dissolved in DMSO are diluted in RPMI HEPES (25 mmol/l) and added to the wells in a 50 μl volume. Final DMSO concentration is 1%. Vehicle alone is added to control wells. Calcein loaded cells are then plated in 50 μl volume and the plates are incubated for 45 min at room temperature.

Fluorescence is measured using the Cytofluor plate reader (excitation: 485 nm; emission: 530 nm).

Plates are washed 4 times to remove non-adherent cells and fluorescence was read again.

The percentage of cell adhesion is calculated as: fluorescence of adherent cells/fluorescence of total cells×100 ($F_x$%). Nonspecific adhesion is calculated from DPBS wells ($F_{ns}$%) Specific adhesion is: $F_x$%–$F_{ns}$%.

Adhesion inhibition is calculated as the decrease of the adhesion of treated cells compared to the adhesion of control cells and expressed in percent as: 100–[($F_x$%–$F_{ns}$%)/($F_c$%–$F_{ns}$%)×100].

$IC_{50}$ is evaluated from a dose-response curve using the following equation:

$$Y=A+((B-A)/(1+((C/X)^{\wedge}D)))$$

with A=minimum inhibition, B=maximum inhibition, C=$IC_{50}$ and D=Hill slope.

Preferred compounds of the invention inhibit the U937 adhesion to VCAM with $IC_{50}$ values below 1 μmol/l.

The invention claimed is:

1. A compound of formula I or a pharmaceutically-acceptable salt thereof,

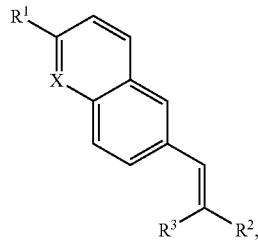

(I)

wherein
X is N;
$R^1$ is cycloalkyl, aryl, heterocycle, aralkyl, heterocycle-alkyl, or an oxy derivative, or a group of the formula:

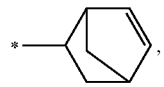

$R^2$ is —$NR^4R^5$, —$OR^4$ or —C(=O)$NR^5R^6$;
$R^3$ is tetrazole, —CN, —$CH_2OH$ or —CO—$R^7$;
$R^4$ is H, —$G^1$—$R^8$, or a group of formula:

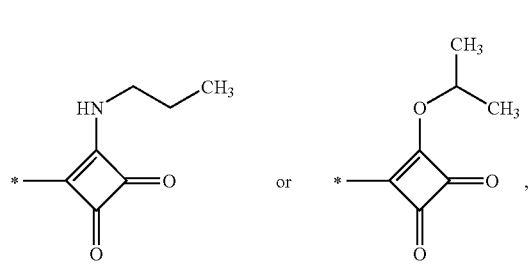

$R^5$ is H, $C_{1-4}$-alkyl; or —$NR^4R^5$ represents a heterocycle or —N=$CR^9R^{10}$;
$R^6$ is aryl, heterocycle, cycloalkyl or aralkyl;
$R^7$ is hydroxy, amino, hydroxylamino, an oxy derivative or an amino derivative;
$G^1$ is CO, $CH_2$, $SO_2$;
$R^8$ is aryl, heterocycle, cycloalkyl, aralkyl or —NH-aryl;
$R^9$ is aryl; and
$R^{10}$ is ether.

2. The compound according to claim 1, wherein
$R^1$ is cycloalkyl, aryl, aromatic heterocycle or aralkyl;
$R^2$ is —$NR^4R^5$;
$R^3$ is —CO—$R^7$;
$R^4$ is —$G^1$—$R^8$;
$R^5$ is H, or $C_{1-4}$-alkyl;
$R^7$ is hydroxy, amino, hydroxylamino or an oxy derivative;
$G^1$ is CO; and
$R^8$ is aryl, heterocycle, cycloalkyl or —NH-aryl.

3. The compound according to claim 2, wherein
$R^1$ is 2,6-dichlorophenyl, 2,4-dichlorophenyl, 2,6-dimethoxyphenyl, 2-nitrophenyl, 2-(trifluoromethyl) phenyl, 2-bromophenyl, 2-(1,3-benzodioxol-5-yl)-1-methylethyl, 2-methoxyphenyl, 4-(methylsulfonyl) phenyl, 5-chloro-1-methyl-3-(trifluoromethyl)-1H-pyrazol-4-yl, 2,6-dimethylphenyl, 2-chloro-6-nitrophenyl, 3,5-dichloro-4-pyridinyl, 2-chloro-6-fluorophenyl, 2-methoxy-1-naphthyl, 2-mesityl;
$R^2$ is —$NHR^4$, wherein $R^4$ is —$G^1$—$R^8$;
$R^7$ is hydroxy, amino or $C_{1-4}$-alkyloxy;
$G^1$ is CO; and
$R^8$ is 2,6-dichlorophenyl, 1-carboxy-1,2,2-trimethyl-3-cyclopentyl, 1-((4-methylphenyl)sulfonyl)-2-piperidinyl, 1-[(4-methylphenyl)sulfonyl]octahydro-1H-indol-2-yl, 1-(4-chlorophenyl)cyclopentyl, 2-chloro-4-(methylsulfonyl)phenyl, 2-chloro-6-methylphenyl, 3-acetyl-1,3-thiazolidin-4-yl, 2,6-dimethoxyphenyl, 2,6-dimethylphenyl, 2,6-difluorophenyl, 2-chloro-4-(methylsulfonyl)phenyl, 1-(methylsulfonyl)-2-piperidinyl, 2-methyltetrahydro-2-furanyl, 1-acetyl-2-pyrrolidinyl, 1-(phenylsulfonyl)-2-pyrrolidinyl, 2,4-dichloro-6-methyl-3-pyridinyl, 1-benzyl-5-oxo-2-pyrrolidinyl, 3-acetyl-1,1-dioxido-1,3thiazolidin-4-yl or 1-[2-(diethylamino)ethyl]cyclopentyl.

4. The compound according to claim 3, wherein
$R^1$ is 2,6-dichlorophenyl, 2,6-dimethoxyphenyl, 3,5-dichloro-4-pyridinyl, 2-nitrophenyl, 2-chloro-6-fluorophenyl, 2-methoxy-1-naphthyl or 2-chloro-6-nitrophenyl;
$R^2$ is —NH—C(=O)—$R^8$;
$R^7$ is hydroxy or $C_{1-4}$-alkyloxy; and
$R^8$ is 2,6-dichlorophenyl, 1-carboxy-1,2,2-trimethyl-3-cyclopentyl, 1-((4-methylphenyl)sulfonyl)-2-piperidinyl, 1-[(4-methylphenyl)sulfonyl]octahydro-1H-indo~2yl, 1-(4-chlorophenyl)cyclopentyl, 2-chloro-4-(methylsulfonyl)phenyl, 2-chloro-6-methylphenyl, 1-(phenylsulfonyl)-2-pyrrolidinyl, 2,4-dichloro-6-methyl-3-pyridinyl or 1-benzyl-5-oxo-2-pyrrolidinyl.

5. The compound according to claim 1, wherein, when the carbon atom to which $R^2$ and $R^3$ are attached is asymmetric, it is in the "S"-configuration.

6. A compound according to claim 1 selected from the group consisting of methyl (2S)-2-[(2,6-dichlorobenzoyl) amino]-3-[2-(2,6-dichlorophenyl)-6-quinolinyl]propanoate; 2-[(2,6-dichlorobenzoyl)amino]-3-[2-(2,6-dichlorophenyl)-6-quinolinyl]propanoic acid; (2S)-2-[(2,6-dichlorobenzoyl) amino]-3-[2-(2,6-dichlorophenyl)-6-quinolinyl]propanoic acid; 2-({[(4R)-3-acetyl-1,3-thiazolidin-4-yl]carbonyl}amino)-3-[2-(2,6-dichlorophenyl)-6-quinolinyl]propanoic acid; 2-[(2,6-dichlorobenzoyl)amino]-3-[2-(2,6-dimethoxyphenyl)-6-quinolinyl]propanoic acid; 3-[2-(2,6-dichlorophenyl)-6-quinolinyl]-2-[(2,6-dimethoxybenzoyl)amino] propanoic acid; 3-[2-(2,6-dichlorophenyl)-6-quinolinyl]-2-[2,6-dimethylbenzoyl)amino]propanoic acid; 2-[(2,6-dichlorobenzoyl)amino]-3-[2-(4-pyridinyl)-6-quinolinyl] propanoic acid; 2-[(2,6-dichlorobenzoyl)amino]-3-[2-(3,5-dichloro-4-pyridinyl)-6-quinolinyl]propanoic acid; methyl 2-[(2,6-dichlorobenzoyl)amino]-3-[2-(3,5-dichloro-4-pyridinyl)-6-quinolinyl]propanoate; 3-[2-(2,6-dichlorophenyl)-6-quinolinyl]-2-[(2,6-difluorobenzoyl)amino]propanoic acid; methyl (2S)-2-{[2-chloro-4-(methylsulfonyl)benzoyl]amino}-3-[2-(2,6-dichlorophenyl)-6-quinolinyl] propanoate; (2S)-2-[(2-chloro-6-methylbenzoyl)amino]-3-[2-(2,6-dichlorophenyl)-6-quinolinyl]propanoic acid; (2S)-2-{[2-chloro-4-(methylsulfonyl)benzoyl]amino}-3-[2-(2,6-dichlorophenyl)-6-quinolinyl]propanoic acid; 2-({[(2,6-dichlorophenyl)amino]carbonyl}amino)-3-[2-(2,6-dichlorophenyl)-6-quinolinyl]propanoic acid; (2S)-2-({[1-(4-chlorophenyl)cyclopentyl]carbonyl}amino)-3-[2-(2,6-dichlorophenyl)-6-quinolinyl]propanoic acid; 3-[2-(2,6-dichlorophenyl)-6-quinolinyl]-2-[({(2S)-1-[(4-methylphenyl)sulfonyl]piperidinyl}carbonyl)amino]propanoic acid; (1R,3S)-3-[({1-carboxy-2-[2-(2,6-dichlorophenyl)-6-quinolinyl]ethyl}amino)carbonyl]-1,2,2-trimethylcyclopentanecarboxylic acid; (2S)-2-[(2,6-difluorobenzoyl)amino]-3-[2-(2-nitrophenyl)-6-quinolinyl] propanoic acid; (2S)-3-[2-(2-chloro-6-fluorophenyl)-6-quinolinyl]-2-[(2,6-difluorobenzoyl)amino]propanoic acid; (2S)-2-[(2,6-difluorobenzoyl)amino]-3-[2-(2-methoxy-1-naphthyl)-6-quinolinyl]propanoic acid; (2S)-2-[(2,6-dichlorobenzoyl)amino]-3-[2-(2-nitrophenyl)-6-quinolinyl]propanoic acid; (2S)-2-[(2,6-dichlorobenzoyl)amino]-3-{2-[2-(trifluoromethyl)phenyl]-6-quinolinyl}propanoic acid; (2S)-3-[2-(2-chloro-6-fluorophenyl)-6-quinolinyl]-2-[(2,6-dichlorobenzoyl)amino]propanoic acid; (2S)-2-[(2,6-dichlorobenzoyl)amino]-3-[2-(2-methoxy-1-naphthyl)-6-quinolinyl]propanoic acid; (2S)-2-[(2-chloro-6-methylbenzoyl)amino]-3-[2-(2-nitrophenyl)-6-quinolinyl] propanoic acid; (2S)-2-[(2-chloro-6-methylbenzoyl)amino]-3-{2-[2-(trifluoromethyl)phenyl]-6-quinolinyl}propanoic acid; (2S)-3-[2-(2-chloro-6-fluorophenyl)-6-quinolinyl]-2-[(2-chloro-6-methylbenzoyl)amino]propanoic acid; (2S)-2-[(2-chloro-6-methylbenzoyl)amino]-3-[2-(2-methoxy-1-naphthyl)-6-quinolinyl]propanoic acid; (2S)-2-{[2-chloro-4-(methylsulfonyl)benzoyl]amino}-3-{2-[2-nitrophenyl)-6-quinolinyl}propanoic acid; (2S)-2-{[2-chloro-4-(methylsulfonyl)benzoyl]amino}-3-{2-[2-(trifluoromethyl)phenyl]-6-quinolinyl}propanoic acid; (2S)-3-[2-(2-chloro-6-fluorophenyl)-6-quinolinyl]-2-{[2-chloro-4-(methylsulfonyl)benzoyl]amino}propanoic acid; (2S)-2-{[2-chloro-4-(methylsulfonyl)benzoyl]amino}-3-[2-(2-methoxy-1-naphthyl)-6-quinolinyl]propanoic acid; (2S)-2-({[(4R)-3-acetyl-1,3-thiazolidin-4-yl]carbonyl}amino)-3-[2-(2,6-dimethoxyphenyl)-6-quinolinyl]propanoic acid; 2-[({(2S 3aS,7aS)-1-[(4-methylphenyl)sulfonyl]octahydro-1H-indol-2-yl}carbonyl)amino]-3-[2-(2,6-dichlorophenyl)-6-quinolinyl]propanoic acid; methyl (2S)-3-[2-(2,6-dichlorophenyl)-6-quinolinyl]-2-({[(2R)-2-methyltetrahydro-2-furanyl]carbonyl}amino)propanoate; (2S)-3-[2-(2,6-dichlorophenyl)-6-quinolinyl]-2-({[(2S)-2-methyltetrahydro-2-furanyl]carbonyl}amino)propanoic acid; (2S)-3-[2-(2,6-dichlorophenyl)-6-quinolinyl]-2-({[(2R)-2-methyltetrahydro-2-furanyl]carbonyl}amino)propanoic acid; 2,6-dichloro-N-[1-{[2-(2,6-dichlorophenyl)-6-quinolinyl]methyl}-2-(hydroxyamino)-2-oxoethyl]benzamide; N-(2-amino-1-{[2-(2,6-dichlorophenyl)-6-quinolinyl]methyl}-2-oxoethyl)-2,6-dichlorobenzamide; methyl (2S)-3-[2-(2,6-dichlorophenyl)-6-quinolinyl]-2-({[(2S)-1-(methylsulfonyl)piperidinyl]carbonyl}amino)propanoate; (2S)-3-[2-(2,6-dichlorophenyl)-6-quinolinyl]-2-({[(2S)-1-(methylsulfonyl)piperidinyl]carbonyl}amino)propanoic acid; ({2-[(2,6-dichlorobenzoyl)amino]-3-[2-(2,6-dichlorophenyl)-6-quinolinyl]propanoyl}oxy)methyl pivalate; 2-[({(2S,3aS,7aS)-1-[(4-methylphenyl)sulfonyl]octahydro-1H-indol-2-yl}carbonyl)amino]-3-[2-(2-chlorophenyl)-6-quinolinyl]propanoic acid; 3-[2-(2-bromophenyl)-6-quinolinyl]-2-[(2,6-dichlorobenzoyl)amino]propanoic acid; 3-[2-(2-bromophenyl)-6-quinolinyl]-2-[({(2S)-1-[(4-methylphenyl)sulfonyl]piperidinyl}carbonyl)amino]propanoic acid; 2-[({(2S,3aS,7aS)-1-[(4-methylphenyl)sulfonyl]octahydro-1H-indol-2-yl}carbonyl)amino]-3-[2-(2-bromophenyl)-6-quinolinyl]propanoic acid; 3-{2-[2-chloro-5-(trifluoromethyl)phenyl]-6-quinolinyl}-2-[(2,6-dichlorobenzoyl)amino]propanoic acid; 2-[(2-chloro-6-methylbenzoyl)amino]-3-{2-[2-chloro-5-(trifluoromethyl)phenyl]-6-quinolinyl}propanoic acid; 2-{[2-chloro-4-(methylsulfonyl)benzoyl]amino}-3-{2-[2-chloro-5-(trifluoromethyl)phenyl]-6-quinolinyl}propanoic acid; 3-{2-[2-chloro-5-(trifluoromethyl)phenyl]-6-quinolinyl}-2-[({(2S)-1-[(4-methylphenyl)sulfonyl]piperidinyl}carbonyl)amino]propanoic acid; 2-[({(2S,3aS,7aS)-1-[(4-methylphenyl)sulfonyl]octahydro-1H-indol-2-yl}carbonyl)amino]-3-{2-[2-chloro-5-(trifluoromethyl)phenyl]-6-quinolinyl}propanoic acid; 2-({[1-(4-chlorophenyl)cyclopentyl]carbonyl}amino)-3-[2-(2-nitrophenyl)-6-quinolinyl]propanoic acid; 2-[(2,6-dimethoxybenzoyl)amino]-3-[2-(2-nitrophenyl)-6-quinolinyl]propanoic acid; 2-[(2-chloro-6-methylbenzoyl)amino]-3-(2-cyclohexyl-6-quinolinyl)propanoic acid; 3-{2-[2-(1,3-benzodioxol-5-yl)-1-methylethyl]-6-quinolinyl}-2-[(2-chloro-6-methylbenzoyl)amino]propanoic acid; 3-{2-[2-(1,3-benzodioxol-5-yl)-1-methylethyl]-6-quinolinyl}-2-{[2-chloro-4-(methylsulfonyl)benzoyl]amino}propanoic acid; 2-({[(1-(4-chlorophenyl)cyclopentyl]carbonyl}amino)-3-[2-(2-methoxyphenyl)-6-quinolinyl]propanoic acid; 2-({[1-(4-chlorophenyl)cyclopentyl]carbonyl}amino)-3-[2-(2,6-dimethoxyphenyl)-6-quinolinyl]propanoic acid; 2-[(2-chloro-6-methylbenzoyl)amino]-3-[2-(2-methoxyphenyl)-6-quinolinyl]propanoic acid; 2-[(2-chloro-6-methylbenzoyl)amino]-3-[2-(2,3-dimethoxyphenyl)-6-quinolinyl]propanoic acid; 2-{[2-chloro-4-(methylsulfonyl)benzoyl]amino}-3-[2-(2-methoxyphenyl)-6-quinolinyl]propanoic acid; 2-{[2-chloro-4-(methylsulfonyl)benzoyl]amino}-3-[2-(2,3-dimethoxyphenyl)-6-quinolinyl]propanoic acid; 2-{[2-chloro-4-(methylsulfonyl)benzoyl]amino}-3-[2-(2,6-dimethoxyphenyl)-6-quinolinyl]propanoic acid; 2-[(2,6-dichlorobenzoyl)amino]-3-[2-(2,4-dichlorophenyl)-6-quinolinyl]propanoic acid; 2-[(2,6-dichlorobenzoyl)amino]-3-{2-[4-(methylsulfonyl)phenyl]-6-quinolinyl}propanoic acid; 3-[2-(2-chloro-6-fluorophenyl)-6-quinolinyl]-2-({[1-(4-chlorophenyl)cyclopentyl]carbonyl}amino)propanoic acid; 2-({[[1-(4-chlorophenyl)cyclopentyl]carbonyl}amino)-3-{2-[2-(trifluoromethyl)phenyl]-6-quinolinyl} propanoic acid; 3-[2-(2,4-dichlorophenyl)-6-quinolinyl]-2-[(2,6-dimethoxybenzoyl)amino]propanoic acid; 2-[(2,6-dimethoxybenzoyl)amino]-3-{2-[2-(trifluoromethyl)phenyl]-6-quinolinyl}propanoic acid; 2-[(2,6-difluorobenzoyl)amino]-3-{2-[4-(methylsulfonyl)phenyl]-6-quinolinyl}propanoic acid; 2-[(2-chloro-6-methylbenzoyl)amino]-3-(2-mesityl-6-quinolinyl)propanoic acid; 2-[(2-chloro-6-methylbenzoyl)amino]-3-[2-(2,4-dichlorophenyl)-

6-quinolinyl]propanoic acid; 2-{[2-chloro-4-(methylsulfonyl)benzoyl]amino}-3-(2-mesityl-6-quinolinyl)propanoic acid; 2-{[2-chloro-4-(methylsulfonyl)benzoyl]amino}-3-[2-(2,4-dichlorophenyl)-6-quinolinyl]propanoic acid; 2-{[(1-acetyl-2-pyrrolidinyl)carbonyl]amino}-3-[2-(2,4-dichlorophenyl)-6-quinolinyl]propanoic acid; (2S)-2-[(2,6-dichlorobenzoyl)amino]-3-[2-(2,6-dimethylphenyl)-6-quinolinyl]propanoic acid; 2-({[1-(4-chlorophenyl)cyclopentyl]carbonyl}amino)-3-[2-(2,3-difluorophenyl)-6-quinolinyl]propanoic acid; 2-[(2,6-dimethoxybenzoyl)amino]-3-[2-(2-methoxy-1-naphthyl)-6-quinolinyl]propanoic acid; 2-[(2-chloro-6-methylbenzoyl)amino]-3-{2-[5-chloro-1-methyl-3-(trifluoromethyl)-1H-pyrazol-4-yl]-6-quinolinyl}propanoic acid; 2-{[2-chloro-4-(methylsulfonyl)benzoyl]amino}-3-{2-[5-chloro-1-methyl-3-(trifluoromethyl)-1H-pyrazol-4-yl]-6-quinolinyl}propanoic acid; (2S)-2-{[2-chloro-4-(methylsulfonyl)benzoyl]amino}-3-[2-(2,6-dimethylphenyl)-6-quinolinyl]propanoic acid; 2-[(2,6-dichlorobenzoyl)amino]-3-[2-(2,6-difluorophenyl)-6-quinolinyl]propanoic acid; 3-[2-(2-chloro-6-nitrophenyl)-6-quinolinyl]-2-[(2,6-dichlorobenzoyl)amino]propanoic acid; 3-[2-(2-chloro-6-nitrophenyl)-6-quinolinyl]-2-[(2,6-dimethoxybenzoyl)amino]propanoic acid; 2-[(2-chloro-6-methylbenzoyl)amino]-3-[2-(2,6-difluorophenyl)-6-quinolinyl]propanoic acid; 2-[(2-chloro-6-methylbenzoyl)amino]-3-[2-(2-chloro-6-nitrophenyl)-6-quinolinyl]propanoic acid; methyl (2S)-2-{[(2,4-dichloro-6-methyl-3-pyridinyl)carbonyl]amino}-3-[2-(2,6-dichlorophenyl)-6-quinolinyl]propanoate; (1R,3S)-3-{[((1S)-1-{[2-(2,6-dichlorophenyl)-6-quinolinyl]methyl}-2-methoxy-2-oxoethyl)amino]carbonyl}-1,2,2-trimethylcyclopentanecarboxylic acid; methyl 2-[(2,6-dichlorobenzoyl)amino]-3-[2-(2,6-dimethoxyphenyl)-6-quinolinyl]propanoate; (1R,3S)-3-[({(1S)-1-carboxy-2-[2-(2,6-dichlorophenyl)-6-quinolinyl]ethyl}amino)carbonyl]-1,2,2-trimethylcyclopentanecarboxylic acid; (2S)-2-({[(4R)-3-acetyl-1,1-dioxido-1,3-thiazolidin-4-yl]carbonyl}amino)-3-[2-(2,6-dichlorophenyl)-6-quinolinyl]propanoic acid; (2S)-2-{[(2,4-dichloro-6-methyl-3-pyridinyl)carbonyl]amino}-3-[2-(2,6-dichlorophenyl)-6-quinolinyl]propanoic acid; methyl (2S)-2-[(2,6-dichlorobenzoyl)amino]-3-[2-(2,6-dimethoxyphenyl)-6-quinolinyl]propanoate; methyl (2S)-2-[(2,6-dichlorobenzoyl)amino]-3-[2-(2,6-dimethylphenyl)-6-quinolinyl]propanoate; (2S)-2-[(2,6-dichlorobenzoyl)amino]-3-[2-(2,6-dimethoxyphenyl)-6-quinolinyl]propanoic acid; (2R)-2-[(2,6-dichlorobenzoyl)amino]-3-[2-(2,6-dimethoxyphenyl)-6-quinolinyl]propanoic acid; (2S)-3-[2-(2,6-dimethoxyphenyl)-6-quinolinyl]-2-({[(2R)-2-methyltetrahydro-2-furanyl]carbonyl}amino)propanoic acid; 2-{[(1-aminocyclopentyl)carbonyl]amino}-3-[2-(2,6-dichlorophenyl)-6-quinolinyl]propanoic acid; (2S)-3-[2-(2,6-dichlorophenyl)-6-quinolinyl]-2-[({1-[2-(diethylamino)ethyl]cyclopentyl}carbonyl)amino]propanoic acid; (2S)-2-[(2,6-dichlorobenzoyl)amino]-3-[2-(3,5-dichloro-4-pyridinyl)-6-quinolinyl]propanoic acid; (2S)-3-[2-(3,5-dichloro-4-pyridinyl)-6-quinolinyl]-2-({[(2R)-2-methyltetrahydro-2-furanyl]carbonyl}amino)propanoic acid; methyl 3-[2-(2,6-dichlorophenyl)-6-quinolinyl]-2-({[(2S)-1-(phenylsulfonyl)pyrrolidinyl]carbonyl}amino)propanoate; methyl (2S)-2-({[1-(4-chlorophenyl)cyclopentyl]carbonyl}amino)-3-[2-(3,5-dichloro-4-pyridinyl)-6-quinolinyl]propanoate; (2S)-2-({[1-(4-chlorophenyl)cyclopentyl]carbonyl}amino)-3-[2-(3,5-dichloro-4-pyridinyl)-6-quinolinyl]propanoic acid; (2S)-2-({[(2S)-1-benzyl-5-oxopyrrolidinyl]carbonyl}amino)-3-[2-(2,6-dichlorophenyl)-6-quinolinyl]propanoic acid and 3-[2-(2,6-dichlorophenyl)-6-quinolinyl]-2-({[(2S)-1-(phenylsulfonyl)pyrrolidinyl]carbonyl}amino)propanoic acid.

7. A compound selected from the group consisting of (2S)-2-[(2,6-dichlorobenzoyl)amino]-3-[2-(2,6-dichlorophenyl)-6-quinolinyl]propanoic acid; A (2S)-2-({[(2S)-1-benzyl-5-oxopyrrolidinyl]carbonyl}amino)-3-[2-(2,6-dichlorophenyl)-6-quinolinyl]propanoic acid.

8. A composition comprising as active ingredient a therapeutically effective amount of a compound according to claim 1 and a pharmaceutically acceptable adjuvant, diluent or carrier.

9. A compound of formula II,

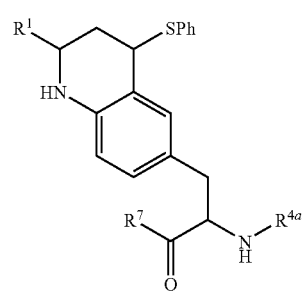

wherein

R¹ is cycloalkyl, aryl, heterocycle, aralkyl, heterocyclealkyl, or a group of formula:

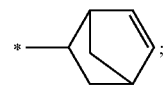

R$^{4a}$ is R⁴ or P;
R⁴ is H, —G¹—R⁸ or a group of formula:

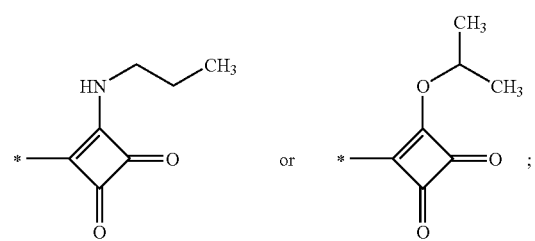

R⁷ is hydroxy or an oxy derivative;
G¹ is CO, CH₂, SO₂;
R⁸ is aryl, heterocycle, cycloalkyl, aralkyl or —NH-aryl; and P is an amine protecting group.

10. A compound of formula III wherein
X is N;
R¹ is cycloalkyl, aryl, heterocycle, aralkyl, heterocycle-alkyl, or an oxy derivative, or a group of formula:

and

R⁷ is hydroxy or an oxy derivative;
with the proviso that when X is CH, then R¹ is cycloalkyl, aryl, heterocycle, aralkyl, heterocycle-alkyl or a group of formula:

11. A compound of formula IV wherein
X is N;
R¹ is cycloalkyl, aryl, heterocycle, aralkyl, heterocycle-alkyl, or an oxy derivative, or a group of formula:

R³ is —CO—R⁷;
R⁷ is hydroxy or an oxy derivative; and
P is an amine protecting group,
with the proviso that when X is CH, then R¹ is cycloalkyl, aryl, heterocycle, aralkyl, heterocycle-alkyl or a group of formula:

12. A compound of formula VI wherein
X is N;
R¹ is cycloalkyl, aryl, heterocycle, aralkyl, heterocycle-alkyl, or an oxy derivative, or a group of formula:

R³ is —CO—R⁷;
R⁷ is hydroxy or an oxy derivative; and
P is an amine protecting group
with the proviso that when X is OH then R¹ is cycloalkyl, aryl, heterocycle, aralkyl, heterocycle-alkyl, or a group of formula:

13. A compound selected from the group consisting of methyl 2-[(tert-butoxycarbonyl)amino]-3-[2-(2,6-dichlorophenyl)-4-(phenylsulfanyl)-1,2,3,4-tetrahydro-6-quinolinyl]propanoate; methyl 2-[(tert-butoxycarbonyl)amino]-3-[2-phenyl-4-(phenylsulfanyl)-1,2,3,4-tetrahydro-6-quinolinyl]propanoate; methyl 2-[(tert-butoxycarbonyl)amino]-3-[2-(2,6-dimethoxyphenyl)-4-(phenylsulfanyl)-1,2,3,4-tetrahydro-6-quinolinyl]propanoate; methyl 2-[(2,6-dichlorobenzoyl)amino]-3-[2-(2,6-dichlorophenyl)-4-(phenylsulfanyl)-1,2,3,4-tetrahydro-6-quinolinyl]propanoate; methyl 2-(benzoylamino)-3-[2-(2,6-dichlorophenyl)-4-(phenylsulfanyl)-1,2,3,4-tetrahydro-6-quinolinyl]propanoate; methyl 2-[(2,6-dichlorobenzyl)amino]-3-[2-(2,6-dichlorophenyl)-4-(phenylsulfanyl)-1,2,3,4-tetrahydro-6-quinolinyl]propanoate; methyl 2-[(2,6-dichlorobenzoyl)amino]-3-[2-(2,6-dimethoxyphenyl)-4-(phenylsulfanyl)-1,2,3,4-tetrahydro-6-quinolinyl]propanoate; methyl 2-[(2,6-dichlorobenzoyl)amino]-3-[4-(phenylsulfanyl)-2-(1,3-thiazol-2-yl)-1,2,3,4-tetrahydro-6-quinolinyl]propanoate; methyl 2-[(2,6-dichlorobenzoyl)

amino]-3-[2-(3,5-dichloro-4-pyridinyl)-4-(phenylsulfanyl)-1,2,3,4-tetrahydro-6-quinolinyl]propanoate; methyl 2-[(2,6-dichlorobenzoyl)amino]-3-[4-(phenylsulfanyl)-2-(4-pyridinyl)-1,2,3,4-tetrahydro-6-quinolinyl]propanoate; methyl (2S)-2-[(2,6-dichlorobenzoyl)amino]-3-[2-(2,6-dichlorophenyl)-4-(phenylsulfanyl)-1,2,3,4-tetrahydro-6-quinolinyl]propanoate; methyl (2R)-2-[(2,6-dichlorobenzoyl)amino]-3-[2-(2,6-dichlorophenyl)-4-(phenylsulfanyl)-1,2,3,4-tetrahydro-6-quinolinyl]propanoate; methyl (2S)-2-[(tert-butoxycarbonyl)amino]-3-[2-(2,6-dichlorophenyl)-4-(phenylsulfanyl)-1,2,3,4-tetrahydro-6-quinolinyl]propanoate; methyl (2R)-2-[(tert-butoxycarbonyl)amino]-3-[2-(2,6-dichlorophenyl)-4-(phenylsulfanyl)-1,2,3,4-tetrahydro-6-quinolinyl]propanoate; methyl (2S)-2-[(tert-butoxycarbonyl)amino]-3-[2-(2,6-dimethoxyphenyl)-4-(phenylsulfanyl)-1,2,3,4-tetrahydro-6-quinolinyl]propanoate; methyl (2R)-2-[(tert-butoxycarbonyl)amino]-3-[2-(2,6-dimethoxyphenyl)-4-(phenylsulfanyl)-1,2,3,4-tetrahydro-6-quinolinyl]propanoate; methyl (2S)-2-[(tert-butoxycarbonyl)amino]-3-[2-(2,6-dimethylphenyl)-4-(phenylsulfanyl)-1,2,3,4-tetrahydro-6-quinolinyl]propanoate; methyl (2S)-2-[(tert-butoxycarbonyl)amino]-3-[2-(3,5-dichloro-4-pyridinyl)-4-(phenylsulfanyl)-1,2,3,4-tetrahydro-6-quinolinyl]propanoate; methyl 3-[2-(2,6-dichlorophenyl)-6-quinolinyl]-2-hydroxy-2-propenoate; methyl 2-[(tert-butoxycarbonyl)amino]-3-[2-(2,6-dichlorophenyl)-6-quinolinyl]propanoate; methyl 2-[(tert-butoxycarbonyl)amino]-3-(2-phenyl-6-quinolinyl)propanoate; methyl 2-[(tert-butoxycarbonyl)amino]-3-[2-(2,6-dimethoxyphenyl)-6-quinolinyl]propanoate; methyl 2-[(tert-butoxycarbonyl)amino]-3-(2-phenoxy-6-quinolinyl)propanoate; methyl 2-[(tert-butoxycarbonyl)amino]-3-[2-(4-chlorophenoxy)-6-quinolinyl]propanoate; methyl 2-[(tert-butoxycarbonyl)amino]-3-(2-methoxy-6-quinolinyl)propanoate; methyl 2-[(tert-butoxycarbonyl)amino]-3-[2-(2-methoxyphenoxy)-6-quinolinyl]propanoate; methyl 2-[(tert-butoxycarbonyl)amino]-3-[2-(2,6-dimethoxyphenoxy)-6-quinolinyl]propanoate; methyl 2-[(tert-butoxycarbonyl)amino]-3-[2-(2,6-dichlorophenoxy)-6-quinolinyl]propanoate; methyl (2S)-2-[(tert-butoxycarbonyl)amino]-3-[2-(2,6-dichlorophenyl)-6-quinolinyl]propanoate; methyl (2R)-2-[(tert-butoxycarbonyl)amino]-3-[2-(2,6-dichlorophenyl)-6-quinolinyl]propanoate; methyl (2S)-2-[(tert-butoxycarbonyl)amino]-3-[2-(2,6-dimethoxyphenyl)-6-quinolinyl]propanoate; methyl (2R)-2-[(tert-butoxycarbonyl)amino]-3-[2-(2,6-dimethoxyphenyl)-6-quinolinyl]propanoate; methyl (2S)-2-[(tert-butoxycarbonyl)amino]-3-[2-(2,6-dimethylphenyl)-6-quinolinyl]propanoate; methyl (2S)-2-[(tert-butoxycarbonyl)amino]-3-[2-(3,5-dichloro-4-pyridinyl)-6-quinolinyl]propanoate; methyl 2-(acetylamino)-3-[6-(2,6-dimethoxyphenyl)-2-naphthyl]propanoate; ethyl 2-(acetylamino)-3-[6-(2,6-dichlorophenyl)-2-naphthyl]propanoate; methyl 2-[(tert-butoxycarbonyl)amino]-3-(2-phenoxy-6-quinolinyl)-2-propenoate; methyl 2-[(tert-butoxycarbonyl)amino]-3-[2-(4-chlorophenoxy)-6-quinolinyl]-2-propenoate; methyl 2-[(tert-butoxycarbonyl)amino]-3-(2-methoxy-6-quinolinyl)-2-propenoate; methyl 2-[(tert-butoxycarbonyl)amino]-3-[2-(2-methoxyphenoxy)-6-quinolinyl]-2-propenoate: methyl 2-[(tert-butoxycarbonyl)amino]-3-[2-(2,6-dimethoxyphenoxy)-6-quinolinyl]-2-propenoate; methyl 2-[(tert-butoxycarbonyl)amino]-3-[2-(2,6-dichlorophenoxy)-6-quinolinyl]-2-propenoate; methyl 2-[(tert-butoxycarbonyl)amino]-3-[2-(2,6-dichlorophenyl)-6-quinolinyl]-2-propenoate; methyl 2-[(2,6-dichlorobenzoyl)amino]-3-(4-nitrophenyl)propanoate; methyl 2-[(2,6-dichlorobenzyl)amino]-3-(4-nitrophenyl)propanoate; methyl 3-(4-aminophenyl)-2-[(2,6-dichlorobenzoyl)amino]propanoate; methyl 3-(4-aminophenyl)-2-[(2,6-dichlorobenzyl)amino]propanoate; 6-(benzyloxy)-2-chloroquinoline; 6-(benzyloxy)-2-phenoxyquinoline; 6-(benzyloxy)-2-(4-chlorophenoxy)quinoline; 6-(benzyloxy)-2-methoxyquinoline; 6-(benzyloxy)-2-(2-methoxyphenoxy)quinoline; 6-(benzyloxy)-2-(2,6-dimethoxyphenoxy)quinoline; 6-(benzyloxy)-2-(2,6-dichlorophenoxy)quinoline; 2-phenoxy-6-quinolinol; 2-(4-chlorophenoxy)-6-quinolinol; 2-methoxy-6-quinolinol; 2-(2-methoxyphenoxy)-6-quinolinol; 2-(2,6-dimethoxyphenoxy)-6-quinolinol; 2-(2,6-dichlorophenoxy)-6-quinolinol; 2-phenoxy-6-quinolinyl trifluoromethanesulfonate; 2-(4-chlorophenoxy)-6-quinolinyl trifluoromethanesulfonate; 2-methoxy-6-quinolinyl trifluoromethanesulfonate; 2-(2-methoxyphenoxy)-6-quinolinyl trifluoromethanesulfonate; 2-(2,6-dimethoxyphenoxy)-6-quinolinyl trifluoromethanesulfonate; 2-(2,6-dichlorophenoxy)-6-quinolinyl trifluoromethanesulfonate; 6-(benzyloxy)-2-(2,6-dichlorophenyl)quinoline; 2-(2,6-dichlorophenyl)-6-quinolinol; 2-(2,6-dichlorophenyl)-6-quinolinyl trifluoromethanesulfonate.

14. A composition comprising as active ingredient a therapeutically effective amount of a compound according to claim 7 and a pharmaceutically acceptable adjuvant, diluent or carrier.

* * * * *

UNITED STATES PATENT AND TRADEMARK OFFICE
CERTIFICATE OF CORRECTION

PATENT NO. : 7,638,630 B2  Page 1 of 1
APPLICATION NO. : 10/513347
DATED : December 29, 2009
INVENTOR(S) : Lassoie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 981 days.

Signed and Sealed this

Ninth Day of November, 2010

David J. Kappos
*Director of the United States Patent and Trademark Office*